(12) United States Patent
Murakami et al.

(10) Patent No.: US 7,776,897 B2
(45) Date of Patent: Aug. 17, 2010

(54) TRIAZOLE DERIVATIVE OR SALT THEREOF

(75) Inventors: Takeshi Murakami, Chuo-ku (JP); Tomoaki Kawano, Chuo-ku (JP); Ryota Shiraki, Chuo-ku (JP); Hirofumi Ishii, Chuo-ku (JP); Seiji Yoshimura, Chuo-ku (JP); Takehiko Ohkawa, Chuo-ku (JP); Mitsuru Hosaka, Chuo-ku (JP); Hiroki Fukudome, Chuo-ku (JP); Yutaka Inoki, Chuo-ku (JP)

(73) Assignee: Astellas Pharma Inc., Tokyo (JP)

( * ) Notice: Subject to any disclaimer, the term of this patent is extended or adjusted under 35 U.S.C. 154(b) by 208 days.

(21) Appl. No.: 11/663,089

(22) PCT Filed: Sep. 14, 2005

(86) PCT No.: PCT/JP2005/016896

§ 371 (c)(1),
(2), (4) Date: Mar. 16, 2007

(87) PCT Pub. No.: WO2006/030805

PCT Pub. Date: Mar. 23, 2006

(65) Prior Publication Data

US 2007/0259854 A1 Nov. 8, 2007

(30) Foreign Application Priority Data

Sep. 16, 2004 (JP) .............................. 2004-269390

(51) Int. Cl.
*A61K 31/41* (2006.01)
*C07D 249/08* (2006.01)
(52) U.S. Cl. .................................. 514/383; 548/262.2
(58) Field of Classification Search ................. 514/383; 548/262.2
See application file for complete search history.

(56) References Cited

U.S. PATENT DOCUMENTS

| | | | |
|---|---|---|---|
| 3,907,821 A | 9/1975 | Gall | |
| 4,577,020 A | 3/1986 | Gall | |
| 5,045,556 A * | 9/1991 | Allgeier | 514/383 |
| 5,098,922 A * | 3/1992 | Allgeier | 514/383 |
| 2004/0133011 A1 | 7/2004 | Waddell et al. | |
| 2009/0082367 A1* | 3/2009 | Yoshimura et al. | 514/255.05 |

FOREIGN PATENT DOCUMENTS

| | | |
|---|---|---|
| EP | 1 798 226 A1 | 6/2007 |
| WO | WO 03/065983 A2 | 8/2003 |
| WO | WO 03/104207 A2 | 12/2003 |
| WO | WO 03/104208 A1 | 12/2003 |
| WO | 2004/014881 A2 | 2/2004 |
| WO | 2004/089367 A1 | 10/2004 |
| WO | 2004/089470 A2 | 10/2004 |
| WO | WO 2004/089367 A1 | 10/2004 |
| WO | WO 2004/089380 A2 | 10/2004 |
| WO | WO 2005/044192 A2 | 5/2005 |
| WO | 2005-170939 A | 6/2005 |
| WO | 2005/065683 | 7/2005 |

OTHER PUBLICATIONS

Patani, et al, Chem. Rev., 1996, 96, 3147-3176, especially p. 3170.*
Rask et al., Tissue-specific dysregulation of cortisol metabolism in human obesity, The Founal of Clinical Endorinology & Metabolism, 2001, 1418-1421, 86, The Endocrine Society, U.S.A.
Lindsay et al.,. Subcutaneous adipose 11b-hydroxysteroid dehydrogenase type 1 activity and messenger ribonucleic acid levels are associated with adiposity and insulinemia in Pima Indians and Caucasians, The Journal of Clinical Endorinology & Metabolism, Jun. 2003, 2738-2744, 88, U.S.A.
Masuzaki et al., A transgenic model of visceral obesity and the metabolic syndrome, Science, Dec. 2001, 2166-2170, vol. 294, U.S.A.
Masuzaki et al, Transgenic amplification of glucocorticoid action in adipose tissue cause high blood pressure in mice, The Journal of Clinical Investigation, Jul. 2003, 83-90, vol. 112, U.S.A.
Morton et al., Improved lipid and lipoprotein profile, hepatic insulin sensivity, and glucose tolerance in llb-hydroxysteroid dehydrogenase type, The Jounral of Biological Chemistry, Nov. 2001, 41293-41300, vol. 44, The American Society for Biochemistry and Molecular Biology Inc., U.S.A.
Davani et al, Type 1 11b-hydroxysteroid dehydrogenase mediates glucocorticoid activation and insulin release in pancreatic islets, The Journal of Biological Chemistry, Nov. 2000, 34841-34844, vol, 275, The American Society for Biochemistry and Molecular Biology Inc., U.S.A.
Cooper et al., Expression and functional consequesces of 11b-hydroxysteroid dehydrogenase activity in human bone, Bone, Sep. 2000, 375-381, vol. 27, Elsevier Science Inc., U.S.A.
Rauz et al., Expression and putative role of 11b-hydroxysteroid dehydrogenase isozymes within the human eye, Investigative Ophthalmology & Visual Science, Aug. 2001, 2037-2042, vol. 42, Association for Research in Vision Ophthalmology, U.S.A.
Sandeep et al., 11b-hydroxysteroid dehydrogenase inhibition improves cognitive function in healthy elderly men and type 2 diabetics, Apr. 2004, 6734-6739, vol. 101, The National Academy of Sciences of the U.S.A., U.S.A.

(Continued)

*Primary Examiner*—Susannah Chung
(74) *Attorney, Agent, or Firm*—Sughrue Mion, PLLC

(57) ABSTRACT

There is provided a compound which can be used for therapy of diseases in which 11β-hydroxysteroid dehydrogenase type 1 (11β-HSD1) participates, in particular diabetes, insulin resistance.

It has been found that a triazole derivative wherein the triazole ring is substituted with a trisubstituted methyl group in the 2-position or a pharmaceutically acceptable salt thereof has a strong 11β-HSD1 inhibitory activity. Moreover, the triazole derivative of the invention exhibits an excellent blood-glucose level-lowering action and hence can be used for therapy of diabetes, insulin resistance.

14 Claims, No Drawings

OTHER PUBLICATIONS

Extended European Search Report dated Jul. 24, 2009 in EP Application No. 05783391.5.
Office Action issued on Sep. 18, 2009 in the corresponding Chinese Application No. 200580030457.6 and an English language translation thereof.

STN search result, CAS Registry No. 339009-40-4.
Katritzky et al., "Ring and side chain reactivities of 1-([1,3,4]oxadiazol-2-ylmethyl)-1H-benzotriazole", ARKIVOC 2001 (ii), pp. 101-108.

* cited by examiner

TRIAZOLE DERIVATIVE OR SALT THEREOF

TECHNICAL FIELD

The present invention relates to a novel triazole derivative or a pharmaceutically acceptable salt thereof, which is useful as a medicament, in particular, a therapeutic or preventive agent for diseases in which 11β-hydroxysteroid dehydrogenase type 1 participates, such as diabetes, insulin resistance.

BACKGROUND ART

Glucocorticoid is a hormone inducing metabolic disorders such as hyperglycemia, insulin resistance, obesity, hyperlipemia and hypertension and is not only produced from the adrenal gland but also converted from an inactive form into an active form at a tissue level to act via its receptor.

11β-Hydroxysteroid dehydrogenase (11β-HSD) is an enzyme catalyzing the conversion and the presence of two sub-types is known. 11β-Hydroxysteroid dehydrogenase type 1 (11β-HSD1) is an enzyme catalyzing the conversion of the inactive form into the active form and is highly expressed in liver and 11β-Hydroxysteroid dehydrogenase type 2 (11β-HSD2) is an enzyme catalyzing the conversion of the active form into the inactive form and is highly expressed in kidney. As a relation between 11β-HSD1 and metabolic diseases, it has been known that activity of 11β-HSD1 is increased in the adipose tissue of a corpulent person (Non-Patent Document 1) and it has been reported that 11β-HSD1 activity shows high correlation with BMI that is an index of the degree of obesity, HOMA-IR that is an index of insulin resistance, and a fasting blood-glucose level (Non-Patent Document 2). Moreover, in a transgenic mouse wherein 11β-HSD1 is overexpressed in an adipose tissue-selective manner, it has been reported that glucocorticoid in the adipose tissue increases and the mouse exhibits insulin resistance, visceral fat-type obesity, hyperlipemia, and hypertension (Non-Patent Documents 3 and 4). In addition, it has been reported that 11β-HSD1 knockout mouse shows improvement in glucose tolerance, decrease in blood triglyceride level and increase in HDL-cholesterol (Non-Patent Document 5).

From the above, it is expected that 11β-HSD1-selective inhibitor suppresses the glucocorticoid action in tissue through inhibition of the conversion into active-form glucocorticoid and, as a result, remedies the metabolic disorders such as hyperglycemia, insulin resistance, obesity, hyperlipidemia and hypertension which are induced by glucocorticoid.

Furthermore, it has been reported that a non-selective 11β-HSD inhibiting agent, carbenoxolone improves decrease in insulin secretion induced by addition of inactive glucocorticoid in murine pancreatic β-cell (Non-Patent Document 6) and thus there is a possibility that a 11β-HSD1 inhibiting agent may not only improve insulin resistance but also remedy hyperglycemia though promotion of insulin secretion.

As the other diseases in which 11β-HSD1 participates, osteoporosis (Non-Patent Document 7), glaucoma (Non-Patent Document 8), and decrease in cognitive function (Non-Patent Document 9) are known, and hence effects of improvement thereof are also expected.

With regard to compounds having an 11β-HSD1 inhibitory action, the following Patent Documents 1 to 8 are known.

Patent Document 1 has reported a triazole derivative represented by the formula (A). However, the derivative is different from the compound of the current invention in a point that the derivative does not contain parts corresponding to A and B of the compound of the invention:

[Chem 1]

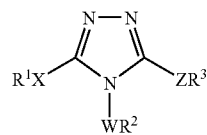

(A)

wherein $R^1$ represents optionally substituted adamantyl, X represents $CH_2$ or a single bond, Z represents S or a single bond (see the document for the other symbols).

Patent Document 2 has reported a triazole derivative represented by the formula (B). However, the derivative is different from the compound of the current invention in a point that the ring attached to the triazole ring is bicyclo[2.2.2]octane:

[Chem 2]

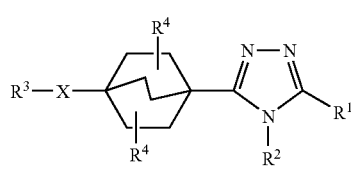

(B)

(see the document for the symbols in the formula).

Patent Documents 3 and 4 have reported a triazole derivative represented by the formula (C). However, the derivative is different from the compound of the current invention in a point that the optionally substituted phenyl ring is attached to the triazole ring through one carbon atom:

[Chem 3]

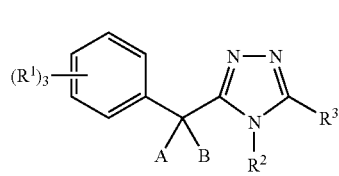

(C)

wherein $R^3$ represents a group selected from each optionally substituted $C_{1-14}$ alkyl, $C_{2-10}$ alkenyl, $SC_{1-6}$ alkyl, $C_{6-10}$ aryl, heterocycle and heteroaryl in the case that $R^2$ and $R^3$ are separated from each other; A represents halo or each optionally substituted $C_{1-6}$ alkyl, $OC_{1-6}$ alkyl or phenyl and B represents H, halo or each optionally substituted $C_{1-6}$ alkyl, $OC_{1-6}$ alkyl, $SC_{1-6}$ alkyl, $C_{2-6}$ alkenyl, phenyl or naphthyl in the case that A and B are separated from each other (see the document for the other symbols).

Patent Document 5 has reported a triazole derivative represented by the formula (D). However, any compounds having substituents at the parts corresponding to A and B of the compound of the current invention are not disclosed as Examples:

[Chem 4]

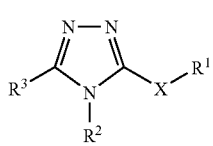

(D)

wherein X represents O or S, $R^1$ represents each optionally substituted $C_3$-$C_{10}$ cycloalkyl, $C_3$-$C_{10}$ heterocycloalkyl, aryl, heteroaryl, aryl$C_1$-$C_6$ alkyl, heteroaryl$C_1$-$C_6$ alkyl, or the like, $R^3$ represents each optionally substituted $C_3$-$C_{10}$ cycloalkyl, $C_3$-$C_{10}$ heterocycloalkyl, aryl, heteroaryl, aryl$C_1$-$C_6$ alkyl, heteroaryl$C_1$-$C_6$ alkyl, aryl$R^8C_1$-$C_6$ alkyl, or heteroaryl$R^8C_1$-$C_6$ alkyl; $R^8$ represents $NR^{10}$, $C(=O)R^{10}$ or $SO_nR^{10}$ (see the document for the other symbols).

Patent Document 6 published after the priority date of the present application has reported a triazole derivative represented by the formula (E). However, compounds wherein a ring is directly attached to the triazole ring are only disclosed as Examples:

[Chem 5]

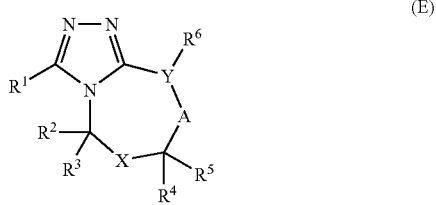

(E)

wherein $R^1$ represents $C_5$-$C_{10}$ cycloalkyl, $C_5$-$C_{10}$ heterocycloalkyl, aryl, heteroaryl, aryl$C_1$-$C_6$ alkyl, or heteroaryl$C_1$-$C_6$ alkyl, or the like (see the document for the other symbols).

Patent Document 7 published after the priority date of the present application has reported a triazole derivative represented by the formula (F). However, Y corresponding to A and B of the compound of the current invention is limited to a ring structure:

[Chem 6]

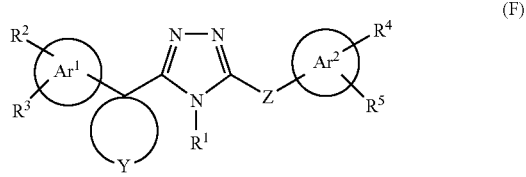

(F)

(see the document for the other symbols in the formula).

Patent Document 8 published after the priority date of the present application has reported a wide variety of compounds represented by the formula (G). However, as compounds having substituents corresponding to A and B of the compound of the invention, compounds wherein the part corresponding to $R^1$ of the compound of the invention is aryl are only disclosed as Examples:

[Chem 7]

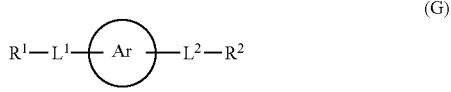

(G)

wherein $R^1$ represents a hydrogen atom or an optionally substituted cyclic group, $R^2$ represents an optionally substituted cyclic group, Ar represents an optionally substituted 5- or 6-membered aromatic heterocycle, and $L^1$ and $L^2$ are the same or different and each represents (1) a bonding hand, (2) an optionally substituted hydrocarbon group, or the like.

Non-Patent Document 1: Rask E., et al., "The Journal of Clinical Endocrinology & Metabolism", (USA), 2001, Vol. 86, pp. 1418-1421

Non-Patent Document 2: Lindsay R. S., et al., "The Journal of Clinical Endocrinology & Metabolism", 2003, Vol. 88, pp. 2738-2744

Non-Patent Document 3: Masuzaki H., et al., "Science", (USA), 2001, Vol. 294, pp. 2166-2170

Non-Patent Document 4: Masuzaki H., et al., "The Journal of Clinical Investigation", (USA), 2003, Vol. 112, pp. 83-90

Non-Patent Document 5: Morton N. M., et al., "The Journal of Biological Chemistry", (USA), 2001, Vol. 276, pp. 41293-41300

Non-Patent Document 6: Davani B., et al., "The Journal of Biological Chemistry", (USA), 2000, Vol. 275, pp. 34841-34844

Non-Patent Document 7: Cooper M. S., et al., "Bone", (USA), 2000, Vol. 27, pp. 375-381

Non-Patent Document 8: Rauz S., et al., "Investigative Opthalmology & Visual Science", (USA), 2001, Vol. 42, pp. 2037-2042

Non-Patent Document 9: Sandeep T. C., et al., "Proceedings of the National Academy of Science", (USA), 2004, Vol. 101, pp. 6734-6739

Patent Document 1: WO03/65983 pamphlet
Patent Document 2: US-A-2004/133011 specification
Patent Document 3: WO03/104207 pamphlet
Patent Document 4: WO03/104208 pamphlet
Patent Document 5: WO04/089367 pamphlet
Patent Document 6: WO04/089380 pamphlet
Patent Document 7: WO05/044192 pamphlet
Patent Document 8: JP-A-2005/170939 publication

DISCLOSURE OF THE INVENTION

Problems that the Invention is to Solve

However, the 11β-HSD1 inhibitors as described in the above documents are not satisfactory in view of any of efficacy, selectivity, safety, and economical efficiency and thus it is highly desired to provide an excellent selective 11β-HSD1 inhibitor.

Means for Solving the Problems

Under such circumstances, as a result of the extensive studies on compounds having 11β-HSD1 inhibitory activity which may expectedly improve diabetes, insulin resistance, the present inventors have found that a novel triazole derivative or a salt thereof according to the invention has an excellent selective inhibitory action on 11β-HSD1 and thus they have accomplished the invention.

Namely, the invention relates to a triazole derivative represented by the formula (I) or a salt thereof:

[Chem 8]

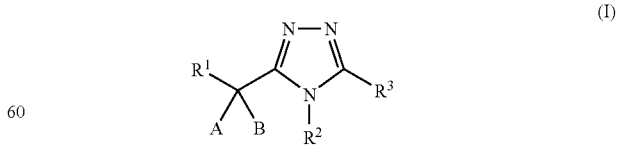

(I)

wherein the symbols have the following meanings:
$R^1$: —N(R)S(O)$_2$-lower alkyl, —N(R$^0$)-optionally substituted lower alkyl, —X—R$^4$, or each optionally substituted cycloalkyl or heterocyclic group;

$R^4$: each optionally substituted aryl, cycloalkyl or heterocyclic group;

X: —O—, —N($R^5$)—, —C(O)—, —S—, —S(O)—, —S(O)$_2$—, —C(O)N($R^0$)—, —N(R)C(O)—, —N($R^0$)C(O)N($R^0$)—, —N($R^6$)S(O)$_2$—, —S(O)$_2$N($R^6$)—, —C(O)-lower alkylene, lower alkylene-C(O)—, —N($R^5$)-lower alkylene, lower alkylene-N($R^5$)—, or each optionally substituted lower alkylene, lower alkenylene or lower alkynylene;

$R^5$: —H, lower alkyl, lower alkylene-CO$_2R^0$, lower alkylene-O$R^0$, —C(O)$R^0$ or —C(O)-aryl, —S(O)$_2R^0$, —S(O)$_2$-aryl or aryl;

$R^6$: —H, lower alkyl, —C(O)$R^0$ or —C(O)-aryl;

$R^0$: the same or different from each other, —H or lower alkyl;

$R^2$: —$R^7$;

$R^3$: —$R^7$, —O$R^7$, —NH$R^7$, —N($R^7$)—C(O)$R^0$, —N($R^7$)S(O)$_2$-lower alkyl, —N($R^7$)$_2$ or —S-lower alkylene-(optionally substituted aryl);

or $R^2$ and $R^3$ are combined together with the nitrogen atom and the carbon atom to which they are attached to form a nitrogen-containing heterocycle;

provided that a ring formed by condensing the triazole ring with the nitrogen-containing heterocycle, which is formed by combining $R^2$ and $R^3$ together with the nitrogen atom and the carbon atom to which they are attached, is not pyrazolo[5,1-c][1,2,4]triazole nor[1,2,4]triazolo[3,4-b][1,3,4]thiadiazine;

$R^7$: the same or different from each other, each optionally substituted lower alkyl, lower alkenyl, lower alkynyl, cycloalkyl, aryl or heterocyclic group;

A and B: the same or different from each other, halogen, —$R^7$, —OH, —O$R^7$, —NH$_2$, —NH$R^7$, —N($R^7$)$_2$, —S$R^7$, —S(O)$R^7$ or —S(O)$_2R^7$; or A and B may be combined together with the carbon atom to which they are attached to form each optionally substituted cycloalkyl ring or non-aromatic heterocycle;

provided that:
1-(1-{5-[(4-chlorobenzyl)sulfanyl]-4-methyl-4H-1,2,4-triazol-3-yl}-1-methylethyl)-1H-1,2,4-triazole,
1-{1-methyl-1-[5-(4-methylphenyl)-4-phenyl-4H-1,2,4-triazol-3-yl]ethyl}-1H-1,2,3-benzotriazole,
N-[2-(4-chlorophenyl)ethyl]-N-methyl-1-(5-methyl-4-phenyl-4H-1,2,4-triazol-3-yl)cyclohex-2-en-1-amine,
3-(2,4-dichlorophenyl)-4-methyl-5-[1-(2-thienyl)cyclopropyl]-4H-1,2,4-triazole,
3-chloro-4-{4-methyl-5-[1-(2-thienyl)cyclopropyl]-4H-1,2,4-triazol-3-yl}benzamide, and
N-(3-chloro-4-{4-methyl-5-[1-(2-thienyl)cyclopropyl]-4H-1,2,4-triazol-3-yl}phenyl)acetamide are excluded. The same shall apply hereinafter.

Moreover, the invention also relates to a pharmaceutical composition comprising a compound represented by the above general formula (I) or a pharmaceutically acceptable salt thereof and a pharmaceutically acceptable carrier, in particular, the pharmaceutical composition, which is an 11β-hydroxysteroid dehydrogenase inhibitor, an insulin resistance-improving agent, or a preventive or therapeutic agent for diabetes.

Namely, it relates to:

(1) the pharmaceutical composition comprising a compound according to the formula (I) or a pharmaceutically acceptable salt thereof and a pharmaceutically acceptable carrier;

(2) the pharmaceutical composition according to the above (1), which is an 11β-hydroxysteroid dehydrogenase inhibitor;

(3) the pharmaceutical composition according to the above (1), which is an insulin resistance-improving agent;

(4) the pharmaceutical composition according to the above (1), which is a preventive or therapeutic agent for diabetes;

(5) use of a compound according to the formula (I) or a pharmaceutically acceptable salt thereof for manufacturing an 11β-hydroxysteroid dehydrogenase inhibitor, an insulin resistance-improving agent or a preventive or therapeutic agent for diabetes;

(6) a method for preventing or treating diabetes comprising administering an effective amount of a compound according to the formula (I) or a salt thereof.

Advantage Of The Invention

An excellent 11β-HSD1-selective inhibitory activity of the compound of the invention was confirmed by the test method shown below.

(1) Test for Measuring Human 11β-HSD1/11β-HSD2 Inhibitory Activity

The procedure for measuring human 11β-HSD1/11β-HSD2 inhibitory activity is as follows. The enzymatic reaction and measurement were performed using a 384-well plate. The reaction was carried out by adding a test compound in various concentrations to a reaction solution containing a 10 mM phosphate buffer solution (pH 6.6), 200 nM cortisone, 40 μM reduced nicotinamide adenine dinucleotide phosphate (NADPH), and human recombinant 11β-HSD1 and then incubating the mixture at room temperature for 1 hour (10 μl/well). The test compound was dissolved in dimethyl sulfoxide (DMSO) to prepare a sample so that the DMSO concentration in the reaction solution became 1%. After the enzymatic reaction, an enzymatic inhibitory activity was measured by detecting cortisol using homogeneous time-resolved fluorescence (HTRF). XL-665-labeled cortisol containing 400 μM carbenoxolone and cryptate-labeled cortisol antibody (CIS Bio International) were added in each amount of 5 μl/well, followed by incubation at room temperature for 2 hours. Then, fluorescence intensity was measured using a fluorophotometer (product name: Discovery, PerkinElmer) and an enzymatic inhibitory activity was calculated based on two-wavelength fluorescence intensity ratio (665 nm/620 nm).

The measurement of 11β-HSD2 inhibitory activity was performed in the same manner as in the measurement of 11β-HSD1 inhibitory activity except for enzymatic reaction conditions. The enzymatic reaction was carried out by adding a test compound in various concentrations to a reaction solution containing a 40 mM tris-hydrochloride buffer solution (Tris-HCl) (pH 8.0), 200 nM cortisol, 200 μM nicotinamide adenine dinucleotide (NAD), and human recombinant 11β-HSD2 and then incubating the mixture at 37° C. for 2 hours (10 μl/well).

The results of the measurement were calculated as an average of the values for 3 wells obtained under the same conditions. The concentration at which the test compound inhibited 50% of the activity was calculated as IC$_{50}$ of the compound in inhibitory activity, the ratio in the case of adding DMSO instead of the test compound being 0% and the ratio in the case of adding no 11β-HSD1 nor 11β-HSD2 being 100%.

IC$_{50}$ values of representative compounds of the invention are shown in the following Table 1. In this connection, Ex indicates Example No. and NT indicates "not performed".

TABLE 1

| Ex | Human 11β-HSD1 (IC$_{50}$/μM) | Human 11β-HSD2 (IC$_{50}$/μM) |
|---|---|---|
| 60 | 0.013 | >3 |
| 62 | 0.0053 | >3 |
| 68 | 0.0044 | >1 |
| 95 | 0.0052 | >1 |
| 100 | 0.0066 | >1 |
| 115 | 0.015 | NT |
| 158 | 0.018 | >3 |
| 174 | 0.060 | NT |

From the above results, it was confirmed that the compound of the invention strongly inhibited 11β-HSD1 and the 11β-HSD1 inhibitory activity of the compound of the invention was selective relative to 11β-HSD2.

(2) ob/ob Mouse Blood-Glucose Lowering Test

A compound solution was prepared using 6% 2-hydroxypropyl-p-cyclodextrin as a solvent. Using 8 weeks-old male ob/ob mice (blood-glucose level of 300 mg or more), blood-glucose levels were measured under non-fasting conditions and then the mice were divided into groups so that the blood-glucose levels became even among the groups. The test compound was orally administered twice per day repeatedly for 9 days (30 mg/kg, bid) and a blood-sugar level was measured 12 hours after final administration (n=6). The blood-glucose level was measured by subjecting a collected blood to protein-removing treatment and then conducting colorimetric quantitative determination of a glucose level (mg/dL) in the supernatant.

As a result, the compound of Example 68 having a strong 11β-HSD1 inhibitory activity showed a blood-glucose lowering action of 32% and thus it was confirmed that the compound of the invention has an excellent blood-glucose lowering action.

BEST MODE FOR CARRYING OUT THE INVENTION

The following will explain the present invention in detail.

The term "lower" herein means a carbon chain having 1 to 6 carbon atoms unless otherwise noted. The term "alkyl", "alkenyl", "alkynyl", "alkylene", "alkenylene" and "alkynylene" each means a straight or branched one.

Therefore, "lower alkyl" is $C_{1-6}$ alkyl, specifically methyl, ethyl, propyl, butyl, pentyl or hexyl, or structural isomers thereof such as isopropyl or tert-butyl, preferably $C_{1-5}$ alkyl, and more preferably methyl, ethyl, propyl, isopropyl, butyl, isobutyl or 3-pentyl.

The "lower alkenyl" means $C_{2-6}$ alkenyl, which may have plurality of double bonds. Specifically, there may be, for example, mentioned ethenyl, propenyl, butenyl, pentenyl, hexenyl, butadienyl or the like. It is preferably $C_{2-3}$ alkenyl, more preferably ethenyl, 1-propenyl, 2-propenyl or 3-propenyl.

The "lower alkynyl" means $C_{2-6}$ alkynyl, which may have plurality of triple bonds. Specifically, there may be, for example, mentioned ethynyl, propynyl, butynyl, pentynyl, hexynyl or the like. It is preferably $C_{2-3}$ alkynyl, more preferably ethynyl, 1-propynyl or 2-propynyl.

The "alkylene" means a divalent group formed by removing one hydrogen atom at any position of alkyl. The "lower alkylene" means $C_{1-6}$ alkylene. Specifically, it is methylene, ethylene, methylmethylene, dimethylmethylene, propylene, butylene, pentylene, hexylene or the like. It is preferably $C_{1-3}$ alkylene, more preferably methylene, ethylene, methylmethylene, dimethylmethylene, 1-propylene or 2-propylene.

The "lower alkenylene" means a divalent group formed by removing one hydrogen atom at any position of $C_{2-6}$ alkenyl. Specifically, it is vinylene, propenylene, butenylene, pentenylene, hexenylene or the like. It is preferably $C_{2-3}$ alkenylene, more preferably vinylene, 1-propenylene or 2-propenylene.

The "lower alkynylene" means a divalent group formed by removing one hydrogen atom at any position of $C_{2-6}$ alkynyl. Specifically, it is ethynylene, propynylene, butynylene, pentynylene, hexynylene or the like. It is preferably $C_{2-3}$ alkynylene, more preferably ethynylene, 1-propynylene or 2-propynylene.

The "cycloalkyl" means a $C_{3-10}$ non-aromatic hydrocarbon ring and may form a bridged ring or a spiro ring. Moreover, it may partially have an unsaturated bond and may be condensed with a benzene ring. However, in the case that a benzene ring is condensed, the bonding hand is present on a non-aromatic ring. Specifically, there may be, for example, mentioned cyclopropyl, cyclobutyl, cyclopentyl, cyclohexyl, cyclooctyl, cyclohexenyl, cyclooctanedienyl, adamantyl, norbonyl, indanyl having a bonding hand at 1- to 3-position, or the like. It is preferably cyclopropyl, cyclobutyl, cyclopentyl or cyclohexyl.

The "halogen" means a halogen atom. Specifically, there may be, for example, mentioned fluoro, chloro, bromo, iodo or the like and it is preferably fluoro or chloro.

The "halogeno-lower alkyl" means a group wherein one or more any hydrogen atoms of the above "lower alkyl" is substituted with the above "halogen" which may be the same or different from each other. Specifically, there may be mentioned trifluoromethyl, pentafluoroethyl or the like. It is preferably trifluoromethyl.

The "aryl" means a monocyclic to tricyclic $C_{6-14}$ aromatic hydrocarbon ring. Specifically, there may be, for example, mentioned phenyl, naphthyl or the like and it is preferably phenyl. Moreover, it may be condensed with a $C_{5-8}$ cycloalkyl ring. However, in the case that a cycloalkyl ring is condensed, the bonding hand is present on the aromatic ring. For example, it may form indanyl having a bonding hand at 4- to 7-position or tetrahydronaphthyl having a bonding hand at 5- to 8-position.

The "aromatic heterocycle" means a monocyclic aromatic heterocycle which is a monocyclic 3- to 8-membered unsaturated ring having 1 to 4 heteroatoms selected from O, S, and N and a bicyclic or tricyclic heterocycle wherein the aromatic heterocycle themselves or the aromatic heterocycle and benzen ring are condensed. The ring atom, S or N, may be oxidized to form an oxide or a dioxide. For example, there may be mentioned pyridyl, pyridazinyl, pyrimidinyl, pyrazinyl, furyl, thienyl, pyrrolyl, oxazolyl, isoxazolyl, oxadiazolyl, thiazolyl, thiadiazolyl, imidazolyl, triazolyl, tetrazolyl, benzofuranyl, benzothienyl, benzoxazolyl, benzimidazolyl, benzothiazolyl, quinolinyl, quinazolinyl, quinoxalinyl, cinnolinyl or the like. It is preferably pyridyl, pyridazinyl, pyrimidinyl, pyrazinyl, furyl, thienyl, pyrrolyl, oxazolyl, isoxazolyl, thiazolyl, imidazolyl, triazolyl, benzofuranyl or benzothienyl. It is particularly preferably pyridyl, thienyl or benzothienyl.

The "heterocycle" is a generic term of the above "aromatic heterocycle" and an additional "non-aromatic heterocycle". The "non-aromatic heterocycle" means a monocyclic non-aromatic heterocycle which is a monocyclic 3- to 12-membered saturated or partially unsaturated monocyclic non-aromatic heterocycle having 1 to 4 heteroatoms selected from O, S, and N and a bicyclic or tricyclic heterocycle wherein the non-aromatic heterocycles themselves or the non-aromatic heterocycle and a cycloalkyl ring, a benzene ring or an aromatic heterocycle are condensed. The ring atom, S or N, may be oxidized to form an oxide or a dioxide or the heterocycle may form a bridged ring or a spiro ring. As the non-aromatic heterocycle, for example, there may be mentioned oxetanyl, dihydropyridyl, dihydropyrrolyl, dihydrooxazolyl, dihydrothiazolyl, dihydroimidazolyl, piperidyl, morpholinyl, thiomorpholinyl, piperazinyl, pyrazolidinyl, imidazolidinyl, pyrrolidinyl, oxazolidinyl, thiazolidinyl, azepanyl, homopiperadinyl, tetrahydrofuranyl, tetrahydropyranyl, tetrahydropyrimidinyl, chromanyl, dioxolanyl, homomorpholinyl or the like. It is preferably pyrrolidinyl, piperidyl, morpholinyl, thiomorpholinyl, piperazinyl, azepanyl or homopiperadinyl.

The "nitrogen-containing heterocycle" which is formed by combining $R^2$ and $R^3$ together with the nitrogen atom and the carbon atom to which they are attached means a heterocycle having one or more nitrogen atoms among the above heterocycles. For example, there may be mentioned a heteroaryl such as pyridyl, pyridazinyl, pyrimidinyl, pyrazinyl, pyrrolyl, oxazolyl, isoxazolyl, oxadiazolyl, thiazolyl, thiadiazolyl, imidazolyl, triazolyl, tetrazolyl, benzoxazolyl, benzimidazolyl, benzothiazolyl, quinolinyl, quinazolyl, quinoxalinyl, cinnolinyl, or pyrrolidinyl; dihydropyridyl, dihydropyrrolyl, dihydrooxazolyl, dihydrothiazolyl, dihydroimidazolyl, piperidyl, morpholinyl, thiomorpholinyl, piperadinyl, pyrazolidinyl, imidazolidinyl, pyrrolidinyl, oxazolidinyl, thiazolidinyl, homopiperadinyl, tetrahydropyrimidinyl, homomorpholinyl, azepanyl, azocanyl, azonanyl or the like. It is preferably piperidyl, azepanyl, azocanyl or azonanyl.

The term "optionally substituted" means "unsubstituted" or "having from 1 to 5 substituents which may be the same or different from one another".

The substituent allowable in the term "optionally substituted" herein may be any substituent which is usually used in the art as a substituent for each group. Moreover, when two or more groups are present as the case of —C(O)N($R^0$)$_2$, each $R^0$ may be the same or different from the other.

As the substituent allowable in each optionally substituted "cycloalkyl" and "heterocyclic group" in $R^1$, each optionally substituted "aryl", "cycloalkyl" and "heterocyclic group" in $R^4$, each optionally substituted "cycloalkyl ring" or "non-aromatic heterocycle" which is formed by combining A and B or $A^a$ and $B^a$ together with the carbon atom to which they are attached, "nitrogen-containing heterocycle" which is formed by combining $R^2$ and $R^3$ together with the nitrogen atom and the carbon atom to which they are attached, and each optionally substituted "aryl", "cycloalkyl" or "heterocyclic group" in $R^7$, a group selected from the following $G^1$ group may preferably be mentioned.

$G^1$ group: lower alkyl, lower alkenyl, halogeno-lower alkyl, halogen, —CN, —NO$_2$, oxo, —OR$^0$, —O-halogeno-lower alkyl, —OC(O)R$^0$, —OC(O)-aryl, —OC(O)N(R$^0$)$_2$, —O-lower alkylene-aryl, —N(R)$_2$, —C(O)R$^0$, —CO$_2$R$^0$, —CO$_2$-lower alkylene-aryl, —C(O)N(R$^0$)$_2$, —NR$^0$C(O)R$^0$, —S(O)$_2$-lower alkyl, —S(O)$_2$-aryl, —N(R)S(O)$_2$-lower alkyl, —N(R$^0$)S(O)$_2$-aryl, lower alkylene-OR$^0$, lower alkylene-N(R$^0$)$_2$, lower alkylene-CO$_2$R$^0$, lower alkylene-C(O)N (R$^0$)$_2$, —O-lower alkylene-OR$^0$, —O-lower alkylene-N(R$^0$)$_2$, —O-lower alkylene-CO$_2$R$^0$, —O-lower alkylene-C(O)N(R)$_2$, cycloalkyl, aryl, heterocyclic group, lower alkylene-aryl, and —O-lower alkylene-O— formed by combining two substituents. The aryl and heterocyclic group in the $G^1$ group may be each substituted with a group selected from $G^2$ group.

$G^2$ group: halogen, lower alkyl, halogeno-lower alkyl, —OR$^0$, —O-halogeno-lower alkyl-N(R)$_2$, oxo, and —O-lower alkylene-O— formed by combining two substituents.

As the substituent allowable in the substituent allowable in "—S-lower alkylene- (optionally substituted aryl)" in $R^3$, a group selected from the above $G^2$ group may be mentioned.

As the substituent allowable in each optionally substituted "lower alkyl", "lower alkenyl" and "lower alkynyl" in $R^7$ and in each optionally substituted "lower alkylene", "lower alkenylene" and "lower alkynylene" in X, a group selected from the following $G^3$ group may be mentioned.

$G^3$ group: halogen, —CN, —OR$^0$, —O-halogeno-lower alkyl, —O-lower alkylene-OR$^0$, oxo, —SR$^0$, —S(O)R$^0$, —S(O)$_2$R$^0$, —N(R)$_2$, —CO$_2$R$^0$, —C(O)N(R$^0$)$_2$, —NR$^0$C(O) R$^0$, —N(R$^0$)S(O)$_2$-lower alkyl, cycloalkyl, aryl and heterocyclic group. The cycloalkyl, aryl and heterocyclic group may be each substituted with a group selected from the above $G^2$ group.

As the substituent allowable in "—N(R$^0$)-optionally substituted lower alkyl" in $R^1$, a group selected from the following $G^4$ group may be mentioned.

$G^4$ group: halogen, —CN, —OR$^0$, —O-halogeno-lower alkyl, oxo, —SR$^0$, —S(O)R$^0$, —S(O)$_2$R$^0$, —N(R$^0$)$_2$, —CO$_2$R$^0$, —C(O)N(R$^0$)$_2$, —NR$^0$C(O)R$^0$ and —N(R$^0$) S(O)$_2$-lower alkyl.

The following show preferable embodiments in the compound of the invention represented by the general formula (I).

$R^1$ is preferably —N(R)-(optionally substituted lower alkyl), optionally substituted heterocyclic group, or a group represented by —X—R$^4$, particularly preferably —N(lower alkyl)$_2$; thiophene, pyridine, benzothiophene or furan which is each optionally substituted with halogen, lower alkyl or —O—R$^0$; or a group represented by —X—R$^4$.

X is preferably —O—, —N(R$^0$)—, —C(O)N(R$^0$)—, —N(R$^0$)C(O)—, —N(R$^0$)S(O)$_2$—, or —S(O)$_2$N(R$^6$)—, particularly preferably —O—, —N(R$^0$)—, *—N(R$^0$)S(O)$_2$— or *—N(R$^0$)C(O)—, wherein * represents a bond to R$^4$.

$R^4$ is preferably each optionally substituted aryl or heterocyclic group, particularly preferably phenyl which is optionally substituted with halogen, lower alkyl or —O—R$^0$.

A and B are preferably the same or different from each other and each is each optionally substituted lower alkyl or lower alkenyl, more preferably lower alkyl, particularly preferably methyl.

The ring which is formed by combining A and B together with the carbon atom to which they are attached is preferably a cycloalkyl ring, particularly preferably a cyclobutyl ring or a cyclopentyl ring.

$R^2$ is preferably lower alkyl or cycloalkyl, more preferably methyl or cyclopropyl.

$R^3$ is preferably optionally substituted aryl, more preferably optionally substituted phenyl, particularly preferably phenyl which is optionally substituted with halogen, lower alkyl or —O—R$^0$.

The nitrogen-containing heterocycle which is formed by combining $R^2$ and $R^3$ together with the nitrogen atom and the carbon atom to which they are attached is preferably a nitrogen-containing heterocycle which is formed by combining $R^2$ and $R^3$ to form $C_{5-10}$ lower alkylene, more preferably a nitrogen-containing heterocycle which is formed by combining $R^2$ and $R^3$ to form $C_{5-6}$ lower alkylene, particularly preferably a nitrogen-containing heterocycle which is formed by combining $R^2$ and $R^3$ to form $C_6$ lower alkylene. The other preferable embodiment is a nitrogen-containing heterocycle which is formed by constituting $C_{5-10}$ lower alkylene.

Furthermore, a compound formed by the combination of the above preferable groups is more preferred.

Moreover, the following show the other preferable compounds among the compounds of the invention represented by the general formula (I).

(1) The compound represented by the formula (I-a):

[Chem 9]

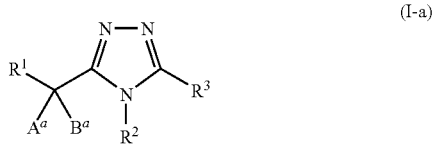

(I-a)

wherein the symbols have the following meanings:
$A^a$ and $B^a$: the same or different from each other, halogen, —$R^7$, —OH, —$OR^7$, —$NH_2$, —$NHR^7$, —$N(R^7)_2$, —$SR^7$, —$S(O)R^7$ or —$S(O)_2R^7$; or (i) in the case that $R^1$ is other than an aromatic heterocyclic group or (ii) in the case that $R^2$ and $R^3$ are combined together with the nitrogen atom and the carbon atom to which they are attached to form a nitrogen-containing heterocycle, $A^a$ and $B^a$ may be combined together with the carbon atom to which they are attached to form each optionally substituted cycloalkyl ring or non-aromatic heterocycle; the same shall apply hereinafter.

(2) The compound according to (1), wherein $R^2$ is lower alkyl or cycloalkyl.

(3) The compound according to (2), wherein $R^3$ is optionally substituted phenyl.

(4) The compound according to (3), wherein $A^a$ and $B^a$ are the same or different from each other and each is optionally substituted lower alkyl.

(5) The compound according to (4), wherein $R^1$ is an optionally substituted aromatic heterocyclic group, —N(lower alkyl)$_2$, —NH-(optionally substituted phenyl), —N(lower alkyl)-(optionally substituted phenyl), —N(—C (CO)-lower alkyl)-(optionally substituted phenyl), —NH—S(O)$_2$-(optionally substituted phenyl) or —N(lower alkyl)-S(O)$_2$-(optionally substituted phenyl).

(6) The compound according to (3), wherein $A^a$ and $B^a$ are combined together with the carbon atom to which they are attached to form optionally substituted cycloalkyl ring.

(7) The compound according to (6), wherein $R^1$ is —C(O) NH-(optionally substituted phenyl) or —C(O)N(lower alkyl)-(optionally substituted phenyl).

(8) The compound according to (1), wherein $R^2$ and $R^3$ are combined together with the nitrogen atom and carbon atom to which they are attached to form an optionally substituted nitrogen-containing heterocycle.

(9) The compound according to (8), wherein $R^2$ and $R^3$ are combined to form $C_{6-10}$ alkylene and it forms an optionally substituted 8-membered to 12-membered ring together with the nitrogen atom and carbon atom to which they are attached.

(10) The compound according to (9), wherein $A^a$ and $B^a$ are combined together with the carbon atom to which they are attached to form optionally substituted cycloalkyl ring.

(11) The compound according to (10), wherein $R^1$ is an optionally substituted aromatic heterocyclic group.

(12) The compound selected from the group consisting of:
3-[1-(5-chloro-2-thienyl)cyclopentyl]-5,6,7,8,9,10-hexahydro[1,2,4]triazolo[4,3-a]azocine,
N-methyl-N-{1-methyl-1-[4-methyl-5-(2-methylphenyl)-4H-1,2,4-triazol-3-yl]ethyl}benzenesulfonamide,
N-methyl-N-{1-methyl-1-[4-methyl-5-(2-methylphenyl)-4H-1,2,4-triazol-3-yl]ethyl}aniline,
N-{1-methyl-1-[4-methyl-5-(2-methylphenyl)-4H-1,2,4-triazol-3-yl]ethyl}-N-phenylacetamide,
3-(2-chlorophenyl)-4-methyl-5-[1-methyl-1-(2-thienyl)ethyl]-4H-1,2,4-triazole,
cis-3-(5,6,7,8,9,10-hexahydro[1,2,4]triazolo[4,3-a]azocin-3-yl)-3-(2-thienyl)cyclobutanol,
2-{1-[5-(2-chlorophenyl)-4-methyl-4H-1,2,4-triazol-3-yl]-1-methylethyl}pyridine,
N-(4-chlorophenyl)-1-[5-(2-chlorophenyl)-4-methyl-4H-1,2,4-triazol-3-yl]cyclobutanecarboxamide,
2-[5-(2-chlorophenyl)-4-methyl-4H-1,2,4-triazol-3-yl]-N-isopropyl-N-methyl-2-propanamine,
2-{1-[5-(2-bromophenyl)-4-methyl-4H-1,2,4-triazol-3-yl]-1-methylethyl}pyridine,
2-chloro-6-{1-[5-(2-chlorophenyl)-4-methyl-4H-1,2,4-triazol-3-yl]-1-methylethyl}pyridine, and
2-{1-[5-(2-bromophenyl)-4-methyl-4H-1,2,4-triazol-3-yl]-1-methylethyl}-6-chloropyridine;
or a pharmaceutically acceptable salt thereof.

The triazole derivatives represented by the formula (I) may form salts and such salts are included in the compounds of the invention as far as they are pharmaceutically acceptable salts. Specifically, there may be mentioned acid addition salts with inorganic acids such as hydrochloric acid, hydrobromic acid, hydroiodic acid, sulfuric acid, nitric acid, and phosphoric acid and organic acids such as formic acid, acetic acid, propionic acid, oxalic acid, malonic acid, succinic acid, fulmaric acid, maleic acid, lactic acid, malic acid, tartaric acid, citric acid, methanesulfonic acid, ethanesulfonic acid, p-toluenesulfonic acid, aspartic acid, and glutamic acid; addition salts with inorganic bases including metals such as sodium, potassium, calcium, and magnesium and organic bases such as methylamine, ethylamine, ethanolamine, lysine, and ornithine; and ammonium salts.

Depending on the kinds of substituents, the compounds of the invention may contain an asymmetric carbon atom and optical isomers may be present. The invention includes all of mixtures of these optical isomers and isolated forms thereof. In addition, the compounds of the invention may exist in the form of tautomers, and the invention includes isolated forms of these isomers and mixtures. Moreover, labeled forms, i.e., compounds obtained by substituting one or more atoms of the compounds of the invention with a radioactive isotope or a nonradioactive isotope are also included in the invention.

Furthermore, the invention include various hydrates, solvates, and polymorphic substances of the compounds of the invention. As a matter of course, the compounds of the invention are not limited to the compound described in Examples below and include all of the derivatives represented by the formula (I) and pharmaceutically acceptable salts thereof.

Furthermore, the compounds of the invention include all compounds which are converted into the compounds of the invention in vivo through metabolism, so-called prodrugs. As the groups which form the prodrugs of the compounds of the invention, there may be mentioned the groups which are described in "Progress in Medicine", Life Science Medica, 1985, Vol. 5, p. 2157-2161 and "Iyakuhin no Kaihatsu" published by Hirokawa Publishing Co., 1990, Vol. 7, Bunshi Sekkei p. 163-198.

(Production Method)

The compound of the invention can be produced by applying various known synthetic methods making use of the characteristics based on its fundamental skeleton or the kind of substituent. The following will exemplify representative production methods. In that case, depending on the kind of functional group, it is sometimes effective from the production technical point of view to replace the functional group by an appropriate protective group, i.e., a group that can be easily converted into the functional group, at the starting material or intermediate stage. Thereafter, the protective group can be removed according to needs to obtain a desired compound. Such functional groups may be, for example, a hydroxyl group, a carboxyl group, an amino group and the like, and examples of protective groups thereof include protective groups described in "Protective Groups in Organic Synthesis", USA, 3rd Ed., written by Greene and Wuts (John Wiley & Sons), 1999, which may be suitably used in response to the reaction conditions.

First Production Method

[Chem 10]

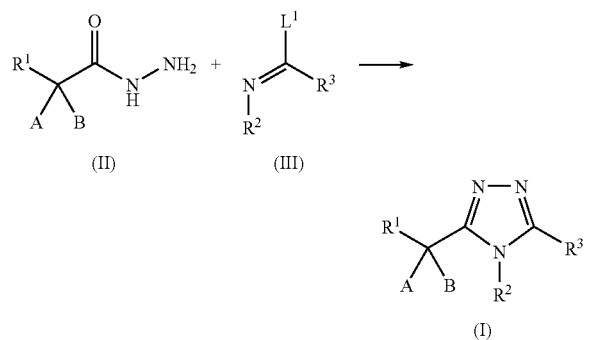

wherein $L^1$ represents a leaving group.

The present production method is a method of producing the compound (I) of the invention by a cyclization reaction of a compound (II) with a compound (III). As the leaving group as $L^1$, there may be, for example, mentioned chloro, bromo, methoxy, methylsulfanyl or the like. The reaction may be carried out in a solvent, e.g., an ether such as tetrahydrofuran (THF), 1,4-dioxane or diglyme; an alcohol such as methanol, ethanol, propanol or butanol; or an aprotic polar solvent such as N,N-dimethylformamide (DMF), dimethylimidazolidinone, dimethylacetamide or DMSO; or the like at room temperature or under heating conditions. Depending on the compound, it may be sometimes advantageous to carry out the reaction in the presence of an acid, e.g., an organic acid such as acetic acid or p-toluenesulfonic acid, a mineral acid such as sulfuric acid or hydrochloric acid, or the like.

Second Production Method

[Chem 11]

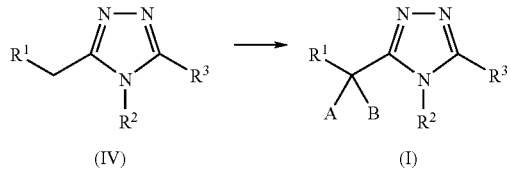

The present production method is a method of producing the compound (I) of the invention by an alkylation reaction of a compound (IV). In the alkylation reaction in this step, sodium hydride, potassium hydride, butyllithium, lithium diisopropylamide or the like may be used as a base and a corresponding alkyl halide, dihalogenated alkane or the like may be used as an electrophilic reagent. The reaction may be carried out in a solvent such as an ether or an aprotic polar solvent under cooling, at room temperature, or under heating conditions.

Depending on the compound, it may be sometimes advantageous to carry out the reaction in the presence of a phase transfer catalyst such as tetra-n-butylammonium iodide.

Third Production Method

[Chem 12]

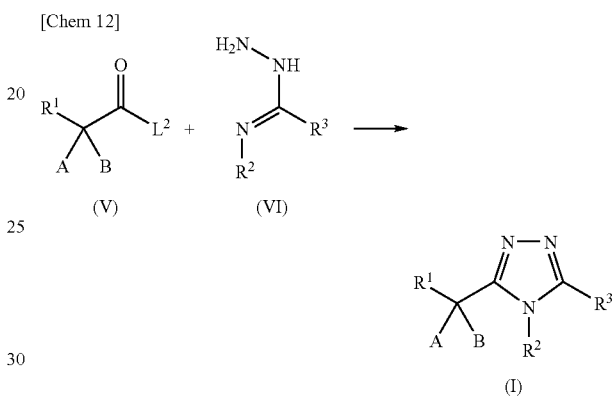

wherein $L^2$ represents a leaving group.

The present production method is a method of producing the compound (I) of the invention by a cyclization reaction of a compound (V) that is an activated carboxylic acid derivative with a compound (VI). As the leaving group as $L^2$, there may be, for example, mentioned chloro, bromo, fluoro, acyloxy or the like. The reaction may be carried out in a solvent such as an ether, an alcohol, or an aprotic polar solvent at room temperature or under heating conditions. Depending on the compound, it may be sometimes advantageous to carry out the reaction in the presence of an acid, e.g., an organic acid such as acetic acid or p-toluenesulfonic acid, a mineral acid such as sulfuric acid or hydrochloric acid, or the like.

Fourth Production Method

[Chem 13]

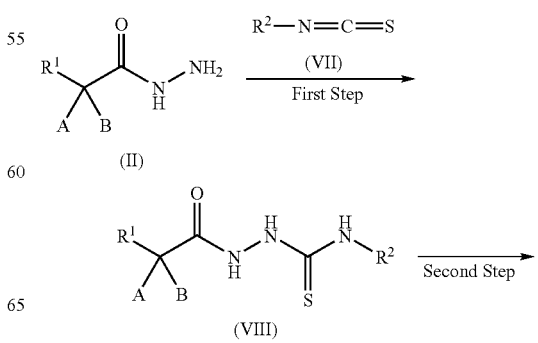

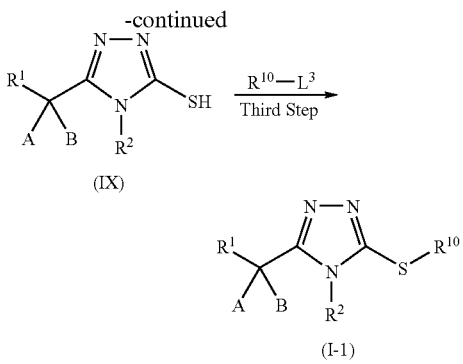

wherein $R^{10}$ represents lower alkylene-(optionally substituted aryl) and $L^3$ represents a leaving group.

The present production method is a method of producing the compound (I-1) of the invention wherein $R^3$ is —S-lower alkylene-(optionally substituted aryl).

First Step

The present step is a step of producing a compound (VIII) by an addition reaction of the compound (II) to a compound (VII). The reaction may be carried out in a solvent such as an alcohol or an ether at room temperature or under heating conditions.

Second Step

The present step is a step of producing a compound (IX) by a cyclization reaction of the compound (VIII). The reaction may be carried out in an aqueous solution of sodium hydroxide, potassium hydroxide or the like under heating conditions.

Third Step

The present invention is a step of producing the compound (I-1) of the invention by a substitution reaction of the compound (IX). As the leaving group as $L^3$, there may be, for example, mentioned chloro, bromo, iodo, methanesulfonyloxy, p-toluenesulfonyloxy or the like. The reaction may be carried out in a solvent such as an ether, an aprotic polar solvent or an alcohol in the presence of a base such as sodium methoxide, sodium ethoxide, sodium carbonate, potassium carbonate, cesium carbonate, sodium hydride or potassium hydride under cooling, at room temperature or under heating conditions.

Furthermore, some of the compounds represented by the formula (I) can be also produced from the compounds of the invention obtained as above by optionally combining the steps usually adoptable by those skilled in the art, such as known alkylation, acylation, substitution reaction, oxidation, reduction, and hydrolysis.

The starting materials for use in the production of the compounds of the invention can be produced by applying the methods described in Referential Examples to be mentioned below, known methods or methods obvious for those skilled in the art, or modified methods thereof, for example.

The compound of the invention thus produced is isolated and purified as its free form or a salt thereof, the salt being produced by carrying out a usual salt formation treatment. The isolation and purification are performed by employing usually used chemical operations such as extraction, concentration, evaporation, crystallization, filtration, recrystallization, and various types of chromatography.

Various isomers can be isolated in the usual way making use of the difference in physicochemical properties between corresponding isomers. For example, a racemic mixture can be separated into an optically pure isomer by a general resolution method of racemic mixture wherein the racemic mixture is converted into diastereomer salts with an optically active organic acid such as tartaric acid and then the salts are subjected to optical resolution. Moreover, a diastereomer mixture can be separated by fractional crystallization or various kinds of chromatography, for example. Also, an optical isomer can be produced starting from an appropriate optically active starting material.

The pharmaceutical composition containing one or more of the compounds of the invention or pharmaceutically acceptable salts thereof as an active ingredient may be prepared in the form of tablets, powders, subtle granules, granules, capsules, pills, liquids, injections, suppositories, ointments, patches and the like using a carrier, an excipient and other additives generally used in formulation, which are administered orally or parenterally.

The clinical dose of the compound of the invention to human may be suitably determined in consideration of the symptom, the body weight, the age, and the sex of the patients to be administered, but suitably, the dose per day is generally from about 0.0001 to 50 mg/kg, preferably from about 0.001 to 10 mg/kg, more preferably from about 0.01 to 1 mg/kg in terms of body weight in the case of oral administration and this may be administered all at a time or may be divided into 2 to 4 portions for administration. In the case of intravenous administration, the dose per day is suitably from about 0.0001 to 1 mg/kg, preferably from about 0.0001 to 0.1 mg/kg in terms of body weight and administration was performed once a day or plurality of times per day. Since the dose varies depending on various conditions, an amount smaller than the above dose range may afford a sufficient effect in some cases.

As the solid composition for oral administration in accordance with the invention, tablets, powders, granules, and the like are used. In such a solid composition, one or more active substances are mixed with at least one inactive diluents, for example, lactose, mannitol, glucose, hydroxypropyl cellulose, microcrystalline cellulose, starch, polyvinylpyrrolidone, magnesium metasilicate aluminate, or the like. According to usual methods, the composition may contain inactive additives other than the diluents, for example, a lubricant such as magnesium stearate, a disintegrator such as calcium cellulose glycolate, a stabilizing agent, and a solubilizing agent. If necessary, the tablets or pills may be coated with sugar coating agents or stomach-soluble or intestine-soluble films, such as sucrose, gelatin, hydroxypropyl cellulose, or hydroxypropylmethyl cellulose phthalate.

The liquid composition for oral administration includes pharmaceutically acceptable emulsions, solutions, suspensions, syrups, and elixirs, and the like and contains inactive diluents generally used, for example, purified water and ethanol (EtOH). The composition may contain an auxiliary agent such as a wetting agent and a suspending agent, a sweetener, a flavoring agent, an aromatic agent, and a preservative in addition to the inactive diluents.

The injections for parenteral administration encompass aseptic, aqueous or non-aqueous solutions, suspensions, and emulsions. The solvents for aqueous solutions and suspensions include, for example, distilled water for injections and physiological saline. The non-aqueous solvents for solutions and suspensions include, for example, propylene glycol, polyethylene glycol, vegetable oils such as olive oil, alcohols such as EtOH, polysorbate 80, and the like. Such a composition may further contain a preservative, a wetting agent, an emulsifier, a dispersant, a stabilizing agent, and a solubilizing agent. They may be sterilized, for example, by filtration through a bacteria-retaining filter, blending with germicides, or irradiation. They may be also prepared into aseptic solid compositions and the compositions may be used, after dissolution in aseptic water or aseptic solvents for injections prior to use.

EXAMPLES

The following will explain the invention specifically with reference to Examples but the invention is not limited to these Examples. In this connection, some of the starting materials to be used in Examples are novel compounds and production methods of such starting materials are explained as Referential Examples.

Incidentally, the symbols in Examples represent the following meanings (the same shall apply hereinafter).

Rf. Referential Example No.; Ex: Example No.; No: Compound No.; Structure: structural formula, Data: physicochemical data (EI: EI-MS; ESP: ESI-MS (Pos); FP: FAB-MS (Pos);

FN: FAB-MS (Neg); NMR1: δ (ppm) of characteristic peaks in $^1$HNMR in DMSO-$d_6$, NMR2: δ (ppm) of characteristic peaks in $^1$HNMR in CDCl$_3$; Sal: salt (compound not indicated represents a free body and each numeral before the salt indicates a compositional ratio; for example, the case that 2HCl is described shows that the compound is a dihydrochloride); Me: methyl; Et ethyl; nPr: n-propyl; iPr: isopropyl; cBu: cyclobutyl; tBu: tert-butyl; cPen: cyclopentyl; cHex: cyclohexyl; Ph: phenyl; Bn: benzyl; Ac: acetyl, Bz: benzoyl, Ms: methanesulfonyl, MOM: methoxymethyl, Boc: tert-butoxycarbonyl, 1-hydroxybenzotriazole: HOBt, 1-ethyl-3-(3-dimethylaminopropyl)carbodiimide: WSC, NMO: N-methylmorpholine-N-oxide (each numeral before the substituent indicates a substitution position and hence, for example, 2-Me-3-Cl—Ph indicates 2-methyl-3-chlorophenyl), Syn: Production method (each numeral indicates that the compound was produced in a similar manner to the compound of Example having the number as Example No. using corresponding starting material(s)); RSyn: Production method (each numeral indicates that the compound was produced in a similar manner to the compound of Referential Example having the number as Referential Example No. using corresponding starting material(s)).

Referential Example 1

Lithium aluminum hydride (1.35 g) was added to a THF (50 ml) solution of methyl 3-chloro-4-methylthiophene-2-carboxylate (3.40 g) at 0° C., followed by stirring at 0° C. for 20 minutes. An 1M aqueous hydrochloric acid solution was added to the reaction solution and the whole was stirred at room temperature for 1 hour. The solution was filtered and, after ethyl acetate was added, the organic layer was separated. Furthermore, the organic layer washed with brine and, after drying over anhydrous sodium sulfate and filtration, the solvent was removed by evaporation under reduced pressure. The resulting crude product was purified by column chromatography (hexane:ethyl acetate=4:1) to obtain 2.68 g of (3-chloro-4-methyl-2-thienyl)methanol (pale yellow oil).

Referential Example 2

Thionyl chloride (2.1 ml) was added dropwise to a chloroform (30 ml) solution of (3-chloro-4-methyl-2-thienyl) methanol (2.34 g), followed by stirring at room temperature for 30 minutes. The reaction solution and chloroform were added to a saturated aqueous sodium hydrogen carbonate solution and then the organic layer was separated. Furthermore, the organic layer washed with brine and, after drying over anhydrous sodium sulfate and filtration, the solvent was removed by evaporation under reduced pressure to obtain 3-chloro-2-(chloromethyl)-4-methylthiophene. Sodium cyamide (1.06 g) and water (15 ml) were added to an acetone (9 ml) solution of 3-chloro-2-(chloromethyl)-4-methylthiophene, followed by stirring at 60° C. for 1 hour. After water and ether were added to the reaction solution, the organic layer was separated. Furthermore, the organic layer washed with brine and, after drying over anhydrous sodium sulfate and filtration, the solvent was removed by evaporation under reduced pressure. The resulting crude product was purified by column chromatography (hexane:ethyl acetate=9:1) to obtain 1.33 g of (3-chloro-4-methyl-2-thienyl)acetonitrile (yellow oil).

Referential Example 3

To a DMF (20 ml) solution of sodium hydride (55%, 967 mg) washed with hexane was added dropwise a DMF (10 ml) solution of (3-chloro-4-methyl-2-thienyl)acetonitrile (1.52 g) and 1,4-dibromobutane (1.27 ml) at 0° C., followed by stirring at room temperature for 19 hours. After the reaction solution and chloroform were added to water, the organic layer was separated. Furthermore, the organic layer washed with brine and, after drying over anhydrous sodium sulfate and filtration, the solvent was removed by evaporation under reduced pressure. The resulting crude product was purified by column chromatography (hexane:ethyl acetate=9:1) to obtain 1.83 g of 1-(3-chloro-4-methyl-2-thienyl)cyclopentanecarbonitrile (colorless oil).

Referential Example 4

Potassium hydroxide (1.36 g) was added to an ethylene glycol (20 ml) solution of 1-(3-chloro-4-methyl-2-thienyl) cyclopentanecarbonitrile and the whole was stirred at 190° C. for 2 hours. After the reaction solution and ether were added to water, the aqueous layer was separated. An 1M aqueous hydrochloric acid solution was added to the aqueous layer to acidify the liquid and, after ether was added, the organic layer was separated. The layer was dried over anhydrous sodium sulfate and filtered and then the solvent was removed by evaporation under reduced pressure to obtain 1.59 g of 1-(3-chloro-4-methyl-2-thienyl)cyclopentanecarboxylic acid (pale brown solid).

Referential Example 5

DMF (a catalytic amount) was added to a thionyl chloride (15 ml) solution of 1-(3-chloro-4-methyl-2-thienyl)cyclopentanecarboxylic acid (1.59 g), followed by stirring at 75° C. for 30 minutes. The reaction solution was subjected to evaporation under reduced pressure to obtain 1-(3-chloro-4-methyl-2-thienyl)cyclopentanecarbonyl chloride. A THF (20 ml) solution of 1-(3-chloro-4-methyl-2-thienyl)cyclopentanecarbonyl chloride was added dropwise to a THF (20 ml) solution of hydrazine monohydrate (12.6 ml) at 0° C., followed by stirring at 0° C. for 3 hours. After the reaction solution and chloroform were added to a saturated aqueous sodium hydrogen carbonate solution, the organic layer was separated. The organic layer washed with brine and, after drying over anhydrous sodium sulfate and filtration, the solvent was removed by evaporation under reduced pressure to obtain 1.65 g of 1-(3-chloro-4-methyl-2-thienyl)cyclopentanecarbohydrazide (pale yellow solid).

Referential Example 6

Hydrazine monohydrate (2.6 ml) was added to an ethanol (10 ml) solution of ethyl 2-methyl-2-(2-thienyl)propanoate (530 mg), followed by stirring at 70° C. for 48 hours. After the reaction solution and ethyl acetate were added to water, the organic layer was separated. Furthermore, the organic layer washed with saturated brine and, after drying over anhydrous sodium sulfate and filtration, the solvent was removed by evaporation under reduced pressure to obtain 447 mg of 2-methyl-2-(2-thienyl)propanohydrazide (colorless oil).

Referential Example 7

Methyl N,2-dimethylbenzenecarbodiimidethioate (717 mg) was dissolved in ethanol (8 ml) and hydrazine monohydrate (3.9 ml) was added thereto at room temperature, followed by stirring at 70° C. for 18 hours. Furthermore, hydrazine monohydrate (2.0 ml) was added thereto and the whole was stirred at 70° C. for 7 hours. After the reaction mixture was concentrated under reduced pressure, it was subjected to azeotropic distillation with toluene to obtain 663 mg of N,2-dimethylbenzenecarbohydrazonamide.

Referential Example 8

1,3-Dibromo-2-propanol, dimethoxymethane, and boron trifluoride diethyl ether complex were reacted in methylene chloride at room temperature to obtain 1,3-dibromo-2-(methoxymethoxy)propane.

Referential Example 9

Thiophene-2-acetonitrile and 1,4-dichloride-2-butene were added to a DMF solution of sodium hydride washed with hexane and the whole was reacted at room temperature to obtain 1-(2-thienyl)cyclopent-3-ene-1-carbonitrile.

Referential Example 10

Cyclohex-1-en-1-ylacetonitrile and 1,4-dibromobutane were reacted in DMF at room temperature in the presence of sodium hydride to obtain 1-cyclohex-1-en-1-ylcyclopentanecarbonitrile.

Referential Example 11

1-Cyclohex-1-en-1-ylcyclopentanecarbonitrile was reacted in methanol at room temperature in the presence of palladium-carbon under a hydrogen atmosphere to obtain 1-cyclohexylcyclopentanecarbonitrile.

Referential Example 12

1-(2-Thienyl)cyclopent-3-en-1-carbonitrile and potassium hydroxide were reacted in ethylene glycol under heating to obtain 1-(2-thienyl)cyclopent-3-en-1-carboxylic acid.

Referential Example 13

1-Cyclohexylcyclopentanecarbonitrile and diisobutylaluminum hydride were reacted in toluene at −78° C. and then the residue and sodium hypochlorite were reacted in a mixed solvent of tert-butanol and THF at room temperature in the presence of 2-methyl-2-butene to obtain 1-cyclohexylcyclopentanecarboxylic acid.

Referential Example 14

1-(2-Thienyl)cyclobutanecarboxylic acid, methyl iodide, and potassium hydrogen carbonate were reacted in DMF at room temperature to obtain methyl 1-(2-thienyl)cyclobutanecarboxylate.

Referential Example 15

Ethyl 2-thienylacetate and 1-propyl iodide were reacted in DMF at room temperature in the presence of sodium hydride to obtain ethyl 2-propyl-2-(2-thienyl)pentanoate.

Referential Example 16

2-(4-Methyl-1,3-thiazol-2-yl)acetonitrile was reacted in a saturated methanol solution of hydrogen chloride under a nitrogen stream under heating and refluxing conditions to obtain methyl (4-methyl-1,3-thiazol-2-yl)acetate.

Referential Example 17

Aniline, ethyl 2-bromoisobutyrate and potassium carbonate were reacted in DMF at 90° C. to obtain ethyl 2-anilino-2-methylpropanoate.

Referential Example 18

Ethyl 1-pyridin-4-ylcyclopentanecarboxylate and benzyl bromide were reacted in acetonitrile under heating. The residue obtained by subjecting the reaction solution to evaporation under reduced pressure, triethylamine and platinum oxide were reacted in ethanol under a hydrogen atmosphere to obtain ethyl 1-(1-benzylpiperidin-4-yl)cyclopentanecarboxylate.

Referential Example 19

Ethyl 1-(1-benzylpiperidin-4-yl)cyclopentanecarboxylate was reacted with potassium hydroxide in ethylene glycol under heating to obtain 1-(1-benzylpiperidin-4-yl)cyclopentanecarboxylic acid.

Referential Example 20

4-(2-Thienyl)tetrahydropyran-4-carboxylic acid was reacted with thionyl chloride and a catalytic amount of DMF in methylene chloride under heating to obtain 4-(2-thienyl)tetrahydropyran-4-carbonyl chloride. A THF solution of 4-(2-thienyl)tetrahydropyran-4-carbonyl chloride was added dropwise to a THF solution of hydrazine monohydrate and the whole was reacted at 0° C. to obtain 4-(2-thienyl)tetrahydropyran-4-carbohydrazide.

Referential Example 21

3,3-Dimethyl-1-(2-thienyl)cyclobutanecarboxylic acid was reacted with HOBt monohydrate and WSC monohydrochloride in acetonitrile at room temperature. The above reaction solution was added dropwise to an acetonitrile solution of hydrazine monohydrate and the whole was reacted at 0° C. to obtain 3,3-dimethyl-1-(2-thienyl)cyclobutanecarbohydrazide.

Referential Example 22

Methyl 1-[(tert-butoxycarbonyl)amino]cyclopentanecarboxylate and hydrazine monohydrate were reacted in methanol under heating to obtain 1-[(tert-butoxycarbonyl)amino]cyclopentanecarbohydrazide.

Referential Example 23

Aniline, cyclopentanone and trimethylsilaneacetonitrile were reacted in acetic acid to obtain 1-aminocyclopentanecarbonitrile.

Referential Example 24

1-Aminocyclopentanecarbonitrile was added to a solution obtained by heating acetic anhydride and formic acid under stirring and the whole was heated to obtain N-(1-cyanocyclopentyl)-N-phenylformamide.

Referential Example 25

N-(1-Cyanocyclopentyl)-N-phenylformamide was suspended in conc. hydrochloric acid (10 ml) and the whole was heated at 105° C. under stirring for 3 hours. The precipitated crystals were collected by filtration and washed with ethyl acetate to obtain 1-anilinocyclopentanecarboxylic acid hydrochloride.

Referential Example 26

1-Anilinocyclopentanecarboxylic acid hydrochloride and N-[3-(dimethylaminopropyl)]-N'-ethylcarbodiimide hydrochloride, 1H-1,2,3-benzotriazol-1-ol hydrate, tert-butyl hydrazinecarboxylate, N,N-diethylisopropylamine were stirred in DMF at room temperature to obtain tert-butyl 2-[(1-anilinocyclopentyl)carbonyl]hydrazinecarboxylate.

Referential Example 27 tert-Butyl 2-[(1-anilinocyclopentyl)carbonyl]hydrazinecarboxylate was dissolved in dioxane and a 4M hydrogen chloride dioxane solution was added thereto. The whole was stirred at room temperature for 3.5 hours to obtain 1-anilinocyclopentanecarbohydrazide.

Referential Example 28

2-(Trifluoromethyl)benzoyl chloride and methylamine (2M, THF solution) were reacted in chloroform at room temperature to obtain N-methyl-2-(trifluoromethyl)benzamide.

Referential Example 29

Toluene solution of 3-(Methoxycarbonyl)benzenecarboxylic acid, thionyl chloride and DMF (a catalytic amount) were heated under stirring. The reaction solution was dissolved in chloroform after evaporation under reduced pressure. After cyclopropylamine and triethylamine were added thereto and the whole was stirred at room temperature to obtain methyl 3-[(cyclopropylamino)carbonyl]benzoate.

Referential Example 30

4-Hydroxybenzenecarboxylic acid was stirred with WSC hydrochloride, HOBt hydrate and cyclopropylamine in DMF at room temperature to obtain N-cyclopropyl-4-hydroxybenzamide.

Referential Example 31

N-Cyclopropyl-4-hydroxybenzamide was stirred with benzyl bromide and potassium carbonate in DMF at room temperature to obtain 4-(benzyloxy)-N-cyclopropylbenzamide.

Referential Example 32

2-piperazinone was suspended in a mixed solvent of dichloromethane and dioxane and then pyridine and benzenesulfonyl chloride were added thereto. After stirring at room temperature for 16 hours, the solvent was removed by evaporation and the resulting solid was suspended in 1N hydrochloric acid, filtered, and washed with diisopropyl ether to obtain 4-(phenylsulfonyl)-2-piperazinone.

Referential Example 33

4-(Phenylsulfonyl)-2-piperazinone was dissolved in dichloromethane, tetramethyloxonium tetrafluoroborate was added thereto, and the whole was stirred to obtain 5-methoxy-1-(phenylsulfonyl)-1,2,3,6-tetrahydropyrazine.

Referential Example 34

After methyltriphenylphosphonium bromide and n-butyllithium were reacted in THF, a THF solution of tert-butyl 2,2-dimethyl-3-oxo-3-phenylpropanoate was added thereto and the whole was reacted under heating to obtain tert-butyl 2,2-dimethyl-3-phenylbut-3-enoate.

Referential Example 35 tert-Butyl 2,2-dimethyl-3-phenylbut-3-enoate and trifluoroacetic acid were reacted in methylene chloride at room temperature to obtain 2,2-dimethyl-3-phenylbut-3-enoic acid.

Referential Example 36 tert-Butyl {2-[(2-chlorobenzoyl)amino]ethyl}carbamate was dissolved in dioxane and a 4M hydrogen chloride dioxane solution was added thereto. The whole was stirred at room temperature to obtain N-(2-aminoethyl)-2-chlorobenzamide hydrochloride.

Referential Example 37

N-(2-Aminoethyl)-2-chlorobenzamide hydrochloride was suspended in dichloromethane and stirred with triethylamine and methanesulfonyl chloride to obtain 2-chloro-N-{2-[(methylsulfonyl)amino]ethyl}benzamide.

Referential Example 38

Ethyl 2-[5-(2-chlorophenyl)-4-methyl-1,2,4-triazol-3-yl]-2-methylpropanoate was reacted with diisobutylaluminum hydride in toluene at −78° C. to obtain 2-[5-(2-chlorophenyl)-4-methyl-1,2,4-triazol-3-yl]-2-methylpropanal.

Referential Example 39

N,2-Dimethylbenzamide, thionyl chloride and a catalytic amount of DMF were reacted in methylene chloride under heating. The residue obtained by evaporation of the reaction solution under reduced pressure was reacted with tert-butyl (2-hydradino-1,1-dimethyl-2-oxoethyl)carbamate in toluene under heating to obtain tert-butyl {1-methyl-1-[4-methyl-5-(2-methylphenyl)-1,2,4-triazol-3-yl]ethyl}carbamate.

Referential Example 40 tert-Butyl {1-methyl-1-[4-methyl-5-(2-methylphenyl)-1,2,4-triazol-3-yl]ethyl}carbamate was reacted with a 4M hydrochloric acid-ethyl acetate solution in ethanol under heating to obtain 2-[4-methyl-5-(2-methylphenyl)-1,2,4-triazol-3-yl]propan-2-amine dihydrochloride.

Referential Example 41

2-Chloro-N-methylbenzamide, thionyl chloride and a catalytic amount of DMF were reacted in methylene chloride under heating. The residue obtained by evaporation of the reaction solution under reduced pressure was reacted with ethyl 1-(hydradinocarbonyl)cyclobutanecarboxylate in toluene under heating to obtain ethyl 1-[5-(2-chlorophenyl)-4-methyl-1,2,4-triazol-3-yl]cyclobutanecarboxylate.

Referential Example 42

Ethyl 1-[5-(2-chlorophenyl)-4-methyl-1,2,4-triazol-3-yl]cyclobutanecarboxylate was reacted with potassium hydroxide in hydrous ethanol at room temperature to obtain 1-[5-(2-chlorophenyl)-4-methyl-1,2,4-triazol-3-yl]cyclobutanecarboxylic acid.

Referential Example 43

Acetaldehyde, acetic acid and sodium triacetoxyborohydride were added to a THF solution of 2-[5-(2-chlorolphenyl)-4-methyl-4H-1,2,4-triazol-3-yl]-2-propanamine and the whole was reacted at room temperature to obtain 2-[5-(2-chlorolphenyl)-4-methyl-4H-1,2,4-triazol-3-yl]-N-ethyl-2-propanamine.

Referential Example 44

Diisopropylethylamine (15.9 ml) and chloro(methoxy)methane (5.48 ml) were added dropwise to a methylene chloride (270 ml) solution of ethyl 3-hydroxy-2,2-dimethyl-3-phenylpropanoate (13.5 g) under ice cooling, followed by stirring at room temperature for 3 days. After the reaction mixture was concentrated under reduced pressure, the residue was diluted with ethyl acetate and water and the organic layer washed with an aqueous hydrochloric acid solution (1M), a saturated aqueous sodium hydrogen carbonate solution and a saturated aqueous sodium chloride solution. The organic layer was subjected to evaporation under reduced pressure and then the residue was purified by silica gel column chromatography to obtain ethyl 3-(methoxymethoxy)-2,2-dimethyl-3-phenylpropanoate (13.1 g).

Similarly to the methods of the above Referential Examples 1 to 44, compounds of Referential Examples 45 to 158 shown in Tables 2 to 16 below were produced using respective corresponding starting materials. Tables 2 to 16 show structures and physicochemical data of the compounds of Referential Examples.

Example 1

7-Methoxy-3,4,5,6-tetrahydro-2H-azepine (0.5 ml) was added to a dioxane (20 ml) and toluene (15 ml) solution of 1-(3-chloro-4-methyl-2-thienyl)cyclopentane-carbohydrazide (800 mg), followed by stirring at 100° C. for 3 days. The reaction solution was subjected to evaporation under reduced pressure and the resulting crude product was purified by column chromatography (chloroform:methanol=40:1). The resulting solid was washed with hexane to obtain 770 mg of 3-[1-(3-chloro-4-methyl-2-thienyl)cyclopentyl]-6,7,8,9-tetrahydro-5H-[1,2,4]triazolo[4,3-a]azepine (colorless solid).

Example 2

3-[1-(Phenylsulfonyl)cyclopentyl]-6,7,8,9-tetrahydro-5H-[1,2,4]triazolo[4,3-a]azepine (110 mg) (colorless oil) was obtained in a similar manner to Referential Example 3 starting from 3-[(phenylsulfonyl)methyl]-6,7,8,9-tetrahydro-5H-[1,2,4]triazolo[4,3-a]azepine (150 mg) synthesized in a similar manner to Example 1 starting from 2-(phenylsulfonyl)acetohydrazide.

Example 3

1-(2-Thienyl)cyclopentanecarboxylic acid (393 mg) was suspended in chloroform (6 ml) and thionyl chloride (0.73 ml) and DMF (2 drops with Pasteur pipette) were added thereto at room temperature, followed by stirring under heating and refluxing for 80 minutes. The reaction system was concentrated under reduced pressure and then was subjected to azeotropic distillation with toluene. The resulting residue was dissolved in THF (7 ml) and the solution was added dropwise under ice cooling to a THF (7 ml) solution of N,2-dimethylbenzenecarbohydrazonamide (322 mg) to which triethylamine (0.28 ml) had been added, followed by stirring under ice cooling for 80 minutes. The reaction system was diluted with diethyl ether (20 ml) and washed with a saturated aqueous sodium bicarbonate solution (15 ml) and brine (15 ml) and then the organic layer was concentrated under reduced pressure after drying. The resulting residue was dissolved in toluene (20 ml) and the whole was stirred at 100° C. for 14 hours. After the reaction system was concentrated under reduced pressure, the residue was purified by column chromatography (methanol:chloroform-3:97) and the resulting solid washed with hexane to obtain-486 mg of 4-methyl-3-(2-methylphenyl)-5-[1-(2-thienyl)cyclopentyl]-4H-1,2,4-triazole.

Example 4

1) Methyl isothiocyanate (62 mg) was added to an ethanol (10 ml) solution of 1-(3-chloro-4-methyl-2-thienyl)cyclopentanecarbohydrazide (200 mg), followed by stirring at 75° C. for 3 hours. The reaction solution was subjected to evaporation under reduced pressure and the resulting crude product washed with ether to obtain 167 mg of 2-{[1-(3-chloro-4-methyl-2-thienyl)cyclopentyl]carbonyl}-N-methylhydrazinecarbothioamide.

2) An 1M aqueous sodium hydroxide solution (10 ml) of 2-{[1-(3-chloro-4-methyl-2-thienyl)cyclopentyl]carbonyl}-N-methylhydrazinecarbothioamide (167 mg) was refluxed for 20 hours. An 1M aqueous hydrochloric acid solution was added to the reaction solution to acidify the solution and precipitated crude crystals were collected by filtration and washed with water to obtain 154 mg of 5-[1-(3-chloro-4-methyl-2-thienyl)cyclopentyl]-4-methyl-2,4-dihydro-3H-1,2,4-triazol-3-thione (pale brown solid).

3) Sodium hydride (55%, 24 mg) was added to a THF (10 ml) solution of 5-[1-(3-chloro-4-methyl-2-thienyl)cyclopentyl]-4-methyl-2,4-dihydro-3H-1,2,4-triazol-3-thione (154 mg) at 0° C. and the whole was stirred for 5 minutes. Then, 2-chlorobenzyl bromide (0.07 ml) was added thereto, followed by stirring at 0° C. for 3 hours. The reaction solution and chloroform were added to a saturated aqueous sodium hydrogen carbonate solution and then the organic layer was separated. Furthermore, the organic layer washed with brine, dried over anhydrous sodium sulfate, and filtered and then the solvent was removed by evaporation under reduced pressure. The resulting crude product was purified by column chromatography (hexane:ethyl acetate=1:1) to obtain 200 mg of 3-[(2-chlorobenzyl)thio]-5-[1-(3-chloro-4-methyl-2-thienyl)cyclopentyl]-4-methyl-4H-1,2,4-triazole (pale yellow foam). It was converted into an ethyl acetate (5 ml) solution and 4M hydrogen chloride-ethyl acetate (0.23 ml) was added, followed by removal of the solvent by evaporation under reduced pressure. The resulting solid washed with ether to obtain 185 mg of 3-[(2-chlorobenzyl)thio]-5-[1-(3-chloro-4-methyl-2-thienyl)cyclopentyl]-4-methyl-4H-1,2,4-triazole hydrochloride (colorless solid).

Example 5

1-(1-Benzylpiperidin-4-yl)cyclopentane-1-carbohydrazide (573 mg) and 8-methoxy-2,3,4,5,6,7-hexahydroazocine (671 mg) were stirred in toluene (10 ml) at 110° C. for 21 hours. The reaction solution was subjected to evaporation under reduced pressure and the resulting crude product was purified by column chromatography (chloroform:methanol=97:3). The resulting solid washed with hexane to obtain 255 mg of 3-[1-(1-benzyl-4-piperidinyl)cyclopentyl]-5,6,7,8,9,10-hexahydro[1,2,4]triazolo[4,3-a]azocine (white solid).

Example 6

(1E)-8-Methoxy-2,3,4,5,6,7-hexahydroazocine (614 mg) and p-toluenesulfonic acid monohydrate (207 mg) were added to a toluene (20 ml) solution of 1-cyclohexylcyclopentanecarbohydrazide (762 mg), followed by stirring at 105° C. for 3 days. The reaction solution and chloroform were added to a saturated aqueous sodium hydrogen carbonate solution and then the organic layer was separated. Furthermore, the organic layer washed with a saturated aqueous sodium chloride solution, dried over anhydrous magnesium sulfate, and filtered and then the solvent was removed by evaporation under reduced pressure. The resulting crude product was purified by flash column chromatography (chloroform:methanol=97:3) to obtain 152 mg of 3-(1-cyclohexylcyclopentyl)-5,6,7,8,9,10-hexahydro[1,2,4]triazolo[4,3-a]azocine (pale brown solid).

Example 7

1M Hydrochloric acid was added to a THF (10 ml) solution of 3-[7,7-dimethyl-2-(2-thienyl)-6,8-dioxaspiro[3,5]non-2-yl]-5,6,7,8,9,10-hexahydro[1,2,4]triazolo[4,3-a]azocine (2270 mg) and the whole was stirred at room temperature for 30 minutes. The reaction solution and chloroform were added to a saturated aqueous sodium hydrogen carbonate solution and then the organic layer was separated. Furthermore, the organic layer washed with a saturated aqueous sodium chloride solution, dried over anhydrous magnesium sulfate, and filtered and then the solvent was removed by evaporation under reduced pressure. The resulting crude product was purified by flash column chromatography (chloroform:methanol=9:1) to obtain 1862 mg of [3-(5,6,7,8,9,10-hexahydro[1,2,4]triazolo[4,3-a]azocin-3-yl)-3-(2-thienyl)cyclobutane-1,1-diyl]dimethanol (colorless solid).

Example 8

Sodium hydride (55%, 193 mg) was added to a THF (10 ml) and DMF (10 ml) mixed solution of [3-(5,6,7,8,9,10-hexahydro[1,2,4]triazolo[4,3-a]azocin-3-yl)-3-(2-thienyl)cyclobutane-1,1-diyl]dimethanol (700 mg), followed by stirring at room temperature for 30 minutes. Then, methyl iodide (0.28 ml) was added thereto and the whole was stirred at room temperature for 1 hour. The reaction solution and chloroform were added to distilled water and then the organic layer was separated. Furthermore, the organic layer was washed with a saturated aqueous sodium chloride solution, dried over anhydrous magnesium sulfate, and filtered and then the solvent was removed by evaporation under reduced pressure. The resulting crude product was purified by flash column chromatography (chloroform:methanol=97:3). 4M hydrogen chloride-ethyl acetate (1 ml) was added to an ethyl acetate (10 ml) solution of the resulting product, followed by stirring at room temperature for 1 hour. Thereafter, the precipitated solid was collected by filtration to obtain 164 mg of 3-[3,3-bis(methoxymethyl)-1-(2-thienyl)cyclobutyl]-5,6,7,8,9,10-hexahydro[1,2,4]triazolo[4,3-a]azocine hydrochloride (colorless solid).

Example 9

3-[1-(2-thienyl)-3-cyclopenten-1-yl]-5,6,7,8,9,10-hexahydro[1,2,4]triazolo[4,3-a]azocine (1.00 g) was dissolved in acetone-water (5:2, 35 ml) and then NMO (587 mg) and osmium tetroxide (0.08M, tert-butanol solution, 4.2 ml) were added thereto, followed by stirring at room temperature for 5.5 hours. A saturated aqueous sodium sulfite solution (40 ml) was added to the reaction solution and the whole was stirred at room temperature for 30 minutes and then diluted with water (200 ml), followed by extraction with chloroform (200 ml×2). The organic layer was dried over anhydrous sodium sulfate, and filtered and then the solvent was removed by evaporation under reduced pressure. The resulting solid was recrystallized from ethanol-water to obtain 367 mg of (1R,2S/1S,2R,4r)-4-(5,6,7,8,9,10-hexahydro[1,2,4]triazolo[4,3-a]azocin-3-yl)-4-(2-thienyl)-1,2-cyclopentanediol (white solid).

Example 10

Sodium hydride (55% oily, 132 mg) was suspended in DMF (5 ml) and then (1R,2S/1S,2R,4r)-4-(5,6,7,8,9,10-hexahydro[1,2,4]triazolo[4,3-a]azocin-3-yl)-4-(2-thienyl)-1,2-cyclopentanediol (459 mg) and methyl iodide (0.017 ml) were added thereto under ice cooling, followed by stirring at room temperature for 2.5 hours. The reaction solution was diluted with water (10 ml) and then extracted with ethyl acetate (15 ml×2). The organic layer washed with water (is ml), dried over anhydrous sodium sulfate, and filtered and then the solvent was removed by evaporation under reduced pressure. The resulting solid was recrystallized from ethyl acetate to obtain 252 mg of 3-[(1r,3R,4S/3S,4R)-3,4-dimethoxy-1-(2-thienyl)cyclopentyl]-5,6,7,8,9,10-hexahydro[1,2,4]-triazolo[4,3-a]azocine (white solid).

Example 11

3-[3-(Methoxymethoxy)-1-(2-thienyl)cyclobutyl]-5,6,7,8,9,10-hexahydro[1,2,4]triazolo[4,3-a]azocine (6.14 g) was dissolved in methylene chloride (125 ml) and then trifluoroacetic acid (25 ml) was added thereto, followed by stirring at room temperature for 21 hours. The reaction solution was subjected to evaporation under reduced pressure and the resulting residue was diluted with a 1M aqueous sodium hydroxide solution (100 ml), followed by extraction with chloroform (100 ml×2). The organic layer was dried over anhydrous sodium sulfate, and filtered and then the solvent was removed by evaporation under reduced pressure. The resulting solid washed with diethyl ether to obtain 3.84 g of 3-(5,6,7,8,9,10-hexahydro[1,2,4]triazolo[4,3-a]azocin-3-yl)-3-(2-thienyl)cyclobutanol (white solid).

Example 12

3-(5,6,7,8,9,10-hexahydro[1,2,4]triazolo[4,3-a]azocin-3-yl)-3-(2-thienyl)cyclobutanol (2.73 g) was dissolved in methylene chloride (330 ml) and then tetra-n-propylammonium perruthenate(VII) (316 mg) and NMO (1.58 g) were added thereto, followed by stirring at room temperature for 15 hours. The reaction solution was subjected to evaporation under reduced pressure and the resulting residue was purified by column chromatography (methanol:chloroform=3:97) to obtain 2.16 g of 3-(5,6,7,8,9,10-hexahydro[1,2,4]triazolo[4,3-a]azocin-3-yl)-3-(2-thienyl)cyclobutanone (pale yellow solid).

Example 13 trans-3-(5,6,7,8,9,10-Hexahydro[1,2,4]triazolo[4,3-a]azocin-3-yl)-3-(2-thienyl)cyclobutyl benzoate (100 mg) was dissolved in methanol (5 ml) and then sodium methoxide (1.0M methanol solution, 0.25 ml) was added under ice cooling, followed by stirring at room temperature for 1 hour. The reaction solution was treated with Amberlyst (registered trademark) A-26 and then the resin was removed by filtration, followed by washing with methanol. The filtrate was subjected to evaporation under reduced pressure and the resulting solid washed with diethyl ether to obtain 65 mg of trans-3-(5,6,7,8,9,10-hexahydro[1,2,4]triazolo[4,3-a]azocin-3-yl)-3-(2-thienyl)cyclobutanol (white solid).

Example 14

N-Cyclopropyl-2-methylbenzamide (263 mg) was dissolved in chloroform (5 ml) and then thionyl chloride (0.55 ml) and DMF (1 drops with Pasteur pipette) were added thereto at room temperature, followed by stirring at 60° C. for 30 minutes. The reaction solution was subjected to evaporation under reduced pressure and then to azeotropic distillation with toluene. The resulting residue was suspended in toluene (10 ml) and then 1-(2-thienyl)cyclopentanecarbohydrazide (210 mg) was added thereto at room temperature, followed by stirring at 60° C. for 30 minutes and subsequently at 110° C. for 38 hours. The reaction solution was subjected to evaporation under reduced pressure and the resulting residue was diluted with ethyl acetate (20 ml), followed by washing with a saturated aqueous sodium bicarbonate solution (10 ml) and brine (10 ml). The organic layer was dried over anhydrous sodium sulfate and filtrated and then the solvent was removed by evaporation under reduced pressure. The resulting residue was purified by column chromatography (methanol:chloroform=3:97) and the resulting solid washed with hexane to obtain 174 mg of 4-cyclopropyl-3-(2-methylphenyl)-5-[1-(2-thienyl)cyclopentyl]-4H-1,2,4-triazole (white solid).

Example 15

To a THF (7 ml) solution of N-{1-[5-(2-chlorophenyl)-4-methyl-4H-1,2,4-triazol-3-yl]-1-methylethyl}aniline (200 mg) were added 36% formaldehyde solution (0.14 ml) and 1.5M sulfuric acid (0.05 ml) and, after stirring at room temperature for 10 minutes, sodium borohydride (81 mg) was added thereto, followed by stirring at room temperature for 10 minutes. After a 1M aqueous sodium hydroxide solution was added to the reaction solution, the reaction solution and chloroform were added to a saturated aqueous sodium chloride solution and then the organic layer was separated. Furthermore, the organic layer was dried over anhydrous magnesium sulfate and filtered and then the solvent was removed by evaporation under reduced pressure. The resulting crude product was purified by flash column chromatography (chloroform:methanol=99:1) and the resulting solid washed with hexane to obtain 72 mg of N-{1-[5-(2-chlorophenyl)-4-methyl-4H-1,2,4-triazol-3-yl]-1-methylethyl}-N-methylaniline (colorless solid).

Example 16

Benzoyl chloride (0.21 ml) and N,N-dimethylaminopyridine (40 mg) were added to a pyridine (15 ml) solution of N-{1-methyl-1-[4-methyl-5-(2-methylphenyl)-4H-1,2,4-triazol-3-yl]ethyl}aniline (500 mg), followed by stirring at 80° C. for 3 days. After the reaction solution and chloroform were added to 1M hydrochloric acid, the reaction solution and chloroform were added to brine and then the organic layer was separated. Furthermore, the organic layer washed with a saturated aqueous sodium hydrogen carbonate solution and a saturated sodium chloride solution successively, dried over anhydrous magnesium-sulfate, and filtered and then the solvent was removed by evaporation under reduced pressure. The resulting crude product was purified by flash column chromatography (chloroform:methanol=99:1 to 98:2) and then the resulting solid washed with ether to obtain 523 mg of N-{1-methyl-1-[4-methyl-5-(2-methylphenyl)-4H-1,2,4-triazol-3-yl]ethyl}-N-phenylbenzamide (colorless solid).

Example 17

Acetic anhydride (0.19 ml) and N,N-dimethylaminopyridine (40 mg) were added to a pyridine (10 ml) solution of N-{1-methyl-1-[4-methyl-5-(2-methylphenyl)-4H-1,2,4-triazol-3-yl]ethyl}aniline (500 mg), followed by stirring at 80° C. for 4 days. After the reaction solution and chloroform were added to a 1M hydrochloric acid solution, the reaction solution and chloroform were added to brine and then the organic layer was separated. Furthermore, the organic layer washed with a saturated aqueous sodium hydrogen carbonate solution and a saturated sodium chloride solution successively, dried over anhydrous magnesium sulfate, and filtered and then the solvent was removed by evaporation under reduced pressure. The resulting crude product was purified by flash column chromatography (chloroform:methanol=99:1 to 96:4) and then the resulting solid was washed with ether to obtain 393 mg of N-{1-methyl-1-[4-methyl-5-(2-methylphenyl)-4H-1,2,4-triazol-3-yl]ethyl}-N-phenylacetamide (pale yellow solid).

Example 18

Thionyl chloride (0.90 ml) and DMF (a catalytic amount) were added to a chloroform (10 ml) solution of 2-chloro-N-methylbenzamide (418 mg), followed by stirring at 60° C. for 30 minutes. The reaction solution was subjected to evaporation under reduced pressure and then toluene (15 ml) and 2-(2,3-dihydro-1H-indol-1-yl)-2-methylpropanhydrazide (450 mg) were added thereto, followed by stirring at 60° C. for 1 hour. The reaction solution and chloroform were added to a saturated aqueous sodium hydrogen carbonate solution and then the organic layer was separated. Furthermore, the organic layer washed with a saturated sodium chloride solution, dried over anhydrous magnesium sulfate, and filtered and then the solvent was removed by evaporation under reduced pressure. Xylene (15 ml) and p-toluenesulfonic acid monohydrate (118 mg) were added to the resulting residue, followed by stirring at 130° C. for 14 hours. The reaction solution and chloroform were added to an aqueous saturated sodium hydrogen carbonate solution and then the organic layer was separated. Furthermore, the organic layer was washed with a saturated sodium chloride solution, dried over anhydrous magnesium sulfate, and filtered and then the solvent was removed by evaporation under reduced pressure. The resulting crude product was purified by flash column chromatography (chloroform:methanol=100:3) to obtain 45 mg of 1-{1-[5-(2-chlorophenyl)-4-methyl-4H-1,2,4-triazol-3-yl]-methylethyl}-1H-indole (pale yellow hard amorphous).

Example 19

Sodium ethanethiolate was added to a DMF (10 ml) solution of 3-(2-chloro-4-methoxyphenyl)-4-methyl-5-[1-(2-thienyl)cyclopentyl]-4H-1,2,4-triazole (300 mg), followed by stirring at 100° C. for 2 hours. After the reaction solution and chloroform were added to distilled water, the organic layer was separated. Furthermore, the organic layer washed with a saturated sodium chloride solution, dried over anhydrous magnesium sulfate, and filtered and then the solvent was removed by evaporation under reduced pressure. The resulting crude product was purified by flash column chromatography (chloroform:methanol=97:3) and then the resulting solid was recrystallized from isopropanol to obtain 30 mg of 3-chloro-4-{4-methyl-5-[1-(2-thienyl)cyclopentyl]-4H-1,2,4-triazol-3-yl}phenol (colorless solid).

Example 20

3-(1-Piperidin-4-ylcyclopentyl)-5,6,7,8,9,10-hexahydro[1,2,4]triazolo[4,3-a]azocine (302 mg) was dissolved in methylene chloride (5 ml) and then methanesulfonyl chloride (0.09 ml) and pyridine (0.24 ml) were added thereto, followed by stirring at room temperature for 6 hours. Furthermore, methanesulfonyl chloride (0.09 ml) and pyridine (0.57 ml) were added thereto, followed by stirring at room temperature for 16 hours. The reaction solution was diluted with a saturated aqueous sodium bicarbonate solution, followed by extraction with chloroform (10 ml×2). The organic layer was dried over anhydrous sodium sulfate and filtered and then the solvent was removed by evaporation under reduced pressure. The resulting residue was purified by column chromatography (methanol:chloroform=1:9) and then the resulting solid washed with ethyl acetate to obtain 117 mg of 3-{1-[1-(methylsulfonyl)-4-piperidinyl]cyclopentyl}-5,6,7,8,9,10-hexahydro[1,2,4]triazolo[4,3-a]azocine (white solid).

Example 21

Sodium hydride (55% oily, 13 mg) was suspended in DMF (2 ml) and then N-{1-methyl-1-[4-methyl-5-(2-methylphenyl)-1,2,4-triazol-3-yl]ethyl}benzensulfonamide (100 mg) and methyl iodide (0.017 ml) were added thereto under ice cooling, followed by stirring at room temperature for 7 hours. The reaction solution was diluted with water (30 ml) and then extracted with chloroform (15 ml×2). The organic layer was dried over anhydrous sodium sulfate and filtered and then the solvent was removed by evaporation under reduced pressure. The resulting solid washed with diethyl ether to obtain 81 mg of N-methyl-N-{1-methyl-1-[4-methyl-5-(2-methylphenyl)-1,2,4-triazol-3-yl]ethyl}benzensulfonamide (white solid).

Example 22

1-[4-Methyl-5-(2-methylphenyl)-1,2,4-triazol-3-yl]cyclopentanamine (263 mg) was dissolved in chloroform (5 ml) and then diisopropylethylamine (1.7 ml) and phenyl isocyanate (0.43 ml) were added thereto, followed by stirring at room temperature for 90 minutes. The reaction solution was diluted with a saturated aqueous sodium bicarbonate solution, followed by extraction with chloroform (10 ml×2). The organic layer was dried over anhydrous sodium sulfate and filtered and then the solvent was removed by evaporation under reduced pressure. The resulting residue was purified by column chromatography (methanol:chloroform=1:19) and the resulting solid washed with ethyl acetate to obtain 68 mg of 1-{1-[4-methyl-5-(2-methylphenyl)-1,2,4-triazol-3-yl]cyclopentyl}-3-phenylurea (white solid).

Example 23

1-[4-Methyl-5-(2-methylphenyl)-1,2,4-triazol-3-yl]cyclopentanamine (270 mg) was dissolved in chloroform (5 ml) and then diisopropylethylamine (1.7 ml) and benzoyl chloride (0.48 ml) were added thereto, followed by stirring at room temperature for 19 hours. The reaction solution was diluted with a saturated aqueous sodium bicarbonate solution, followed by extraction with chloroform (10 ml×2). The organic layer was dried over anhydrous sodium sulfate and filtered and then the solvent was removed by evaporation under reduced pressure. The resulting residue was purified by column chromatography (methanol:chloroform=1:19) and the resulting solid was dissolved in ethanol (1 ml) and then a 1M aqueous sodium hydroxide solution (2 ml) was added thereto, followed by stirring at room temperature for 6 days. The resulting solid was collected by filtration and washed with water to obtain 51 mg of N-{1-[4-methyl-5-(2-methylphenyl)-1,2,4-triazol-3-yl]cyclopentyl}benzamide (white solid).

Example 24

Sodium hydride (60%, 16 mg) was added to a DMF (10 ml) solution of N-{1-[5-(2-chlorophenyl)-4-methyl-4H-1,2,4-triazol-3-yl]-1-methylethyl}benzamide (130 mg), followed by stirring at room temperature for 30 minutes. Then, methyl iodide (0.027 ml) was added thereto and the whole was stirred at room temperature for 1 hour. A saturated aqueous sodium hydrogen carbonate solution and chloroform were added to the reaction solution and then the organic layer was separated. Furthermore, the organic layer was washed with a saturated aqueous sodium chloride solution, dried over anhydrous magnesium sulfate and filtered and then the solvent was removed by evaporation under reduced pressure. The resulting crude product was purified by flash column chromatography (chloroform:methanol=100:3) to obtain 104 mg of N-{1-[5-(2-chlorophenyl)-4-methyl-4H-1,2,4-triazol-3-yl]-1-methylethyl}-N-methylbenzamide (colorless solid).

Example 25

2-[4-Methyl-5-(2-chlorophenyl)-1,2,4-triazol-3-yl]propan-2-amine (1.19 g) and phthalic anhydride (704 mg) were diluted with acetic acid (5 ml), followed by stirring under heating and refluxing for 22 hours. The reaction solution was subjected to evaporation under reduced pressure and the resulting residue was diluted with ethyl acetate (50 ml) and washed with a saturated aqueous sodium bicarbonate solution (30 ml×2). The organic layer was dried over anhydrous sodium sulfate and filtered and then the solvent was removed by evaporation under reduced pressure. The resulting solid was recrystallized from ethanol-water to obtain 1.47 g of 2-{1-[5-(2-chlorophenyl)-4-methyl-1,2,4-triazol-3-yl]-1-methylethyl}-1H-isoindole-1,3-(2H)-dione (white solid).

Example 26

Trifluoroacetic acid (2 ml) was added to a chloroform (4 ml) solution of tert-Butyl-{1-[5-(2-chlorophenyl)-4-methyl-4H-1,2,4-triazol-3-yl]-1-methylethyl}carbamate (500 mg), followed by stirring at room temperature for 2 hours. The reaction solution and chloroform were added to an aqueous saturated sodium hydrogen carbonate solution and then the organic layer was separated. Furthermore, the organic layer washed with a saturated aqueous sodium chloride solution, dried over anhydrous magnesium sulfate, and filtered and then the solvent was removed by evaporation under reduced pressure. Potassium carbonate (394 mg) and 1,2-bis(bromomethyl)benzene (376 mg) were added to a DMF (10 ml) solution of the resulting residue, followed by stirring at 60° C. for 14 hours. Distilled water and chloroform were added to the reaction solution and then the organic layer was separated. Furthermore, the organic layer washed with an aqueous saturated sodium chloride solution, dried over anhydrous magnesium sulfate, and filtered and then the solvent was removed by evaporation under reduced pressure. The resulting crude product was purified by flash chromatography (chloroform:methanol=25:1) to obtain 35 mg of 2-{1-[5-(2-chlorophenyl)-4-methyl-4H-1,2,4-triazol-3-yl]-1-methylethyl} isoindoline (colorless solid).

Example 27

3-(1-Piperidin-4-ylcyclopentyl)-5,6,7,8,9,10-hexahydro [1,2,4]triazolo[4,3-a]azocine (263 mg) and 1H-triazole-1-methanol (86 mg) were diluted with methanol (4 ml), followed by stirring at 60° C. for 1 hour. After 1H-triazole-1-methanol (93 mg) was added thereto and the whole was stirred for 1 hour, 1H-triazole-1-methanol (107 mg) was further added and the whole was stirred for 1 hour. The reaction solution was cooled to room temperature and then sodium borohydride (91 mg) was added thereto, followed by stirring at room temperature for 16 hours. The reaction solution was subjected to evaporation under reduced pressure and the resulting residue was diluted with a 1M aqueous sodium hydroxide solution (30 ml), followed by extraction with chloroform (15 ml×2). The organic layer was dried over anhydrous sodium sulfate and filtered and then the solvent was removed by evaporation under reduced pressure. The resulting residue was purified by column chromatography (methanol:chloroform=1:6) and then the resulting solid washed with hexane to obtain 105 mg of 3-[1-(1-methyl-4-piperidinyl)cyclopentyl]-5,6,7,8,9,10-hexahydro[1,2,4]triazolo[4,3-a] azocine (white solid).

Example 28

1-[5-(2-Chlorophenyl)-4-methyl-1,2,4-triazol-3-yl]cyclobutanecarboxylic acid (150 mg) was suspended in chloroform (5 ml) and then thionyl chloride (0.2 ml) and DMF (1 drop with Pasteur pipette) were added thereto, followed by stirring at 60° C. for 30 minutes. Then, the reaction solution was subjected to evaporation under reduced pressure and then to azeotropic distillation with toluene. The resulting residue was dissolved in chloroform (5 ml) and then diisopropylethylamine (0.27 ml) and (2-fluorophenyl)amine (60 μl) were added thereto, followed by stirring at room temperature for 3 days. The reaction solution was diluted with a saturated aqueous sodium bicarbonate solution (20 ml), followed by extraction with chloroform (10 ml×2). The organic layer was dried over anhydrous sodium sulfate and filtrated and then the solvent was removed by evaporation under reduced pressure. The resulting residue was purified by column chromatography (methanol:chloroform=2:98) and the resulting solid washed with hexane and diethyl ether to obtain 28 mg of 1-[5-(2-chlorophenyl)-4-methyl-1,2,4-triazol-3-yl]-N-(2-fluorophenyl)cyclobutanecarboxamide (white solid).

Example 29

1-[5-(2-Chlorophenyl)-4-methyl-1,2,4-triazol-3-yl]cyclobutanecarboxylic acid (200 mg) was suspended in methylene chloride (7 ml) and then diisopropylethylamine (0.72 ml) and bromotris(pyrrolidino)phosphonium hexafluorophosphate salt (416 mg) were added thereto, followed by stirring at room temperature for 30 minutes. Then, 1-adamantanamine (104 mg) was added to the reaction solution and the whole was stirred at room temperature for 15 hours. The reaction solution was diluted with a saturated aqueous sodium bicarbonate solution (30 ml), followed by extraction with chloroform (20 ml×2). The organic layer was dried over anhydrous sodium sulfate and filtrated and then the solvent was removed by evaporation under reduced pressure. The resulting residue was purified by column chromatography (methanol:chloroform=2:98) and the resulting solid washed with hexane and diethyl ether to obtain 212 mg of N-1-adamantyl-1-[5-(2-chlorophenyl)-4-methyl-1,2,4-triazol-3-yl]cyclobutanecarboxamide (white solid).

Example 30

Sodium hydride (55% oily, 13 mg) was suspended in DMF (3 ml) and then N-(4-chlorophenyl)-1-[5-(2-chlorophenyl)-4-methyl-1,2,4-triazol-3-yl]cyclobutanecarboxamide was added thereto under ice cooling, followed by stirring at room temperature for 30 minutes. Methyl iodide (17 μl) was added thereto under ice cooling, followed by stirring at room temperature for 3 hours. The reaction solution was diluted with ethyl acetate (30 ml) and washed with a saturated sodium bicarbonate solution (10 ml×2). The organic layer was dried over anhydrous sodium sulfate and filtered and then the solvent was removed by evaporation under reduced pressure. The resulting residue was purified by column chromatography (methanol:chloroform=2:98) to obtain 83 mg of N-(4-chlorophenyl)-1-[5-(2-chlorophenyl)-4-methyl-1,2,4-triazol-3-yl]-N-methylcyclobutanecarboxamide (white solid).

Example 31

Methyl 3-{4-cyclopropyl-5-[1-(2-thienyl)cyclobutyl]-4H-1,2,4-triazol-3-yl}benzoate (206 mg) was dissolved in dioxane (4 ml) and a 1M aqueous sodium hydroxide solution (1.1 ml) was added thereto at room temperature, followed by stirring at the same temperature for 12 hours. The solvent was removed by evaporation and pH was adjusted to 4 by adding an aqueous citric acid solution, followed by extraction with chloroform. The extract was dried over anhydrous magnesium sulfate and filtered and then the solvent was removed by evaporation under reduced pressure to obtain an amorphous. Furthermore, ethyl acetate was added thereto and the whole was heated under stirring to obtain 155 mg of 3-{4-cyclopropyl-5-[1-(2-thienyl)cyclobutyl]-4H-1,2,4-triazol-3-yl}benzenecarboxylic acid (white crystals).

Example 32

3-[4-(Benzyloxy)phenyl]-4-cyclopropyl-5-[1-(2-thienyl)cyclobutyl]-4H-1,2,4-triazole was dissolved in methanol (4 ml) and 1,4-dioxane (3 ml) and, after palladium hydroxide (236 mg) was added thereto, the whole was stirred under a hydrogen atmosphere of 1 atm at room temperature for 15 hours. After filtration through celite, the filtrate was purified by silica gel chromatography (chloroform:methanol=99:1 to 95:5) and the resulting crystals were washed with diisopropyl ether to obtain 32 mg of 4-{4-cyclopropyl-5-[1-(2-thienyl)cyclobutyl]-4H-1,2,4-triazol-3-yl}phenol (white crystals).

Example 33

Cyclopentanone (0.18 ml), acetic acid (0.14 ml), and sodium triacetoxyborohydride (380 mg) were added to a toluene (9 ml) solution of 2-[5-(2-chlorolphenyl)-4-methyl-4H-1,2,4-triazol-3-yl]propan-2-amine, followed by stirring at 100° C. for 16 hours. Chloroform, a 1M aqueous sodium hydroxide solution, and distilled water were added to the reaction solution and then the organic layer was separated. Furthermore, the organic layer washed with a saturated aqueous sodium chloride solution, dried over anhydrous magnesium sulfate, and filtered and then the solvent was removed by evaporation under reduced pressure. The resulting crude product was purified by flash column chromatography (chloroform:methanol=100:1) and the resulting solid was washed with hexane to obtain 170 mg of N-{1-[5-(2-chlorolphenyl)-4-methyl-4H-1,2,4-triazol-3-yl]-1-methylethyl}cyclopentanamine (colorless solid).

Example 34

To an acetonitrile (10 ml) solution of N-{1-[5-(2-chlorophenyl)-4-methyl-4H-1,2,4-triazol-3-yl]-1-methylethyl}cyclopentanamine (120 mg) were added 36% formaldehyde solution (92 µl) and sodium triacetoxyborohydride (239 mg), followed by stirring at room temperature for 6 hours. After chloroform, a 1M aqueous sodium hydroxide solution, and distilled water were added to the reaction solution, the organic layer was separated. Furthermore, the organic layer washed with a saturated aqueous sodium chloride solution, dried over anhydrous magnesium sulfate and filtered and then the solvent was removed by evaporation under reduced pressure. The resulting crude product was purified by flash column chromatography (chloroform:methanol=25:1). 4M hydrogen chloride-ethyl acetate (0.38 ml) was added to an ethyl acetate (15 ml) solution of the resulting product and, after stirring at room temperature for 30 minutes, the precipitated solid was collected by filtration to obtain 146 mg of N-{1-[5-(2-chlorophenyl)-4-methyl-4H-1,2,4-triazol-3-yl]-1-methylethyl}-N-methylcyclopentanamine dihydrochloride (colorless solid).

Example 35

2-[5-(2-Chlorophenyl)-4-methyl-1,2,4-triazol-3-yl]-2-methylpropanal (200 mg) was dissolved in 1,2-dichloroethane (4 ml) and then aniline (73 µl) and sodium triacetoxyborohydride (225 mg) were added thereto, followed by stirring at room temperature for 3 days. The reaction solution was diluted with a saturated aqueous sodium bicarbonate solution (30 ml), followed by extraction with chloroform (10 ml×3). The organic layer was dried and then concentrated under reduced pressure and the resulting residue was purified by silica gel column chromatography (methanol:chloroform=2:98). The resulting solid washed with diethyl ether to obtain 98 mg of N-{2-[5-(2-chlorophenyl)-4-methyl-1,2,4-triazol-3-yl]-2-methylpropyl}aniline (white solid).

Example 36

Benzyltriphenylphosphonium bromide (1.15 g) was suspended in THF (30 ml) and, under ice cooling, n-butyllithium (1.60M hexane solution, 1.50 ml) was added thereto, followed by stirring at room temperature for 30 minutes. A THF (20 ml) solution of 2-[5-(2-chlorophenyl)-4-methyl-1,2,4-triazol-3-yl]-2-methylpropanal (633 mg) was added dropwise to the reaction solution and the whole was stirred under heating and refluxing for 20 hours. The reaction mixture was quenched with water (50 ml) and then extracted with ethyl acetate (50 ml×2). The organic layer washed with a 1M aqueous hydrochloric acid solution (30 ml), a saturated aqueous sodium bicarbonate solution, and a brine (30 ml). The organic layer was dried and then concentrated under reduced pressure and the resulting residue was purified by silica gel column chromatography (methanol:chloroform=2:98) and preparative thin layer chromatography (ethyl acetate:hexane=3:1) to obtain 86 mg of 3-(2-chlorophenyl)-5-[(2E)-1,1-dimethyl-3-phenylprop-2-en-1-yl]-4-methyl-1,2,4-triazol (white solid).

Example 37

3-[1-(2-Thienyl)cyclobutyl]-5,6,7,8,9,10-hexahydro[1,2,4]triazolo[4,3-a]azocine (60 mg) was dissolved in acetic acid (3 ml) and then bromosuccinimide (38 mg) was added, followed by stirring at room temperature for 8 hours under light-shielding. The reaction solution was diluted with chloroform (30 ml) and then washed with water (10 ml), a 1M aqueous sodium hydroxide solution (10 ml), and brine (10 ml). The organic layer was dried and then concentrated under reduced pressure and the resulting residue was purified by silica gel column chromatography (methanol:chloroform=2:98) to obtain 60 mg of 3-[1-(5-bromo-2-thienyl)cyclobutyl]-5,6,7,8,9,10-hexahydro[1,2,4]triazolo[4,3-a]azocine (white solid).

Example 38

Benzyl 3-[1-(5-chloro-2-thienyl)cyclopentyl]-5,6,8,9-tetrahydro-7H-[1,2,4]triazolo[4,3-d][1,4]diazepine-7-carboxylate (565 mg) was dissolved in a mixed solvent of methanol (10 ml) and 1,4-dioxane (5 ml). After palladium hydroxide (86 mg) was added thereto, the whole was stirred under a hydrogen atmosphere of 1 atm at room temperature for 48 hours to obtain 3-[1-(2-thienyl)cyclopentyl]-6,7,8,9-tetrahydro-5H-[1,2,4]triazolo[4,3-d][1,4]diazepine (190 mg).

Example 39

3-[1-(2-Thienyl)cyclopentyl]-6,7,8,9-tetrahydro-5H-[1,2,4]triazolo[4,3-d][1,4]diazepine (190 mg) was dissolved in dichloromethane (15 ml) and then pyridine (106 µl) and acetic anhydride (62 µl) were added at room temperature, followed by stirring at the same temperature for 15 hours. The residue obtained by removing the solvent by evaporation was diluted with ethyl acetate and washed with 0.3M hydrochloric acid, water, and brine, successively. The solution was dried over anhydrous magnesium sulfate and filtered and then the solvent was removed by evaporation under reduced pressure. The residue was purified by silica gel column chromatography (chloroform:methanol=99:1 to 95:5) to obtain 110 mg of 7-acetyl-3-[1-(2-thienyl)cyclopentyl]-6,7,8,9-tetrahydro-5H-[1,2,4]triazolo[4,3-d][1,4]diazepine (white solid).

Example 40

1-(1-Benzylpiperidin-4-yl)cyclopentane-1-carbohydrazide (1.04 g) and 8-methoxy-2,3,4,5,6,7-hexahydroazocine (1.46 g) were reacted in toluene (10 ml) under heating to obtain 3-[1-(1-benzyl-4-piperidinyl)cyclopentyl]-5,6,7,8,9,10-hexahydro[1,2,4]triazolo[4,3-a]azocine (0.686 g). The resulting compound was reacted in ethanol under a hydrogen atmosphere using 10% palladium-active carbon (0.14 g) as a catalyst and, after filtration through celite, the resulting solution was concentrated to obtain 3-(1-piperidin-4-ylcyclopentyl)-5,6,7,8,9,10-hexahydro[1,2,4]triazolo[4,3-a]azocine (0.610 g).

Example 41

1-Benzyl-4-{1-[5-(2-chlorophenyl)-4-methyl-1,2,4-triazol-3-yl]cyclopentyl}piperidine (0.87 g) and 1-chloroethyl chlorocarbonate (0.24 ml) were reacted in methylene chloride (20 ml) at room temperature for 2.5 hours. The residue obtained by subjecting the reaction solution to evaporation under reduced pressure was heated and refluxed in methanol (20 ml). After concentration, dil. hydrochloric acid (30 ml) was added thereto and the whole washed with diethyl ether. After neutralization, the product was extracted with chloroform (20 ml×2) and the concentration residue was purified by silica gel column chromatography (methanol:chloroform=4:96) to obtain 4-{1-[5-(2-chlorophenyl)-4-methyl-1,2,4-triazol-3-yl]cyclopentyl}piperidine (0.553 g).

Example 42

3-(Methoxymethoxy)-1-(2-thienyl)cyclobutanecarbohydrazide (5.45 g) and 8-methoxy-2,3,4,5,6,7-hexahydroazocine (4.51 g) were heated in toluene (60 ml) at 110° C. for 19 hours. After concentration, the concentrate was purified by silica gel column chromatography (methanol:chloroform=2:98) to obtain 3-[3-(methoxymethoxy)-1-(2-thienyl)cyclobutyl]-5,6,7,8,9,10-hexahydro[1,2,4]triazolo[4,3-a]azocine (6.14 g).

Examples 43 and 44

3-(5,6,7,8,9,10-Hexahydro[1,2,4]triazolo[4,3-a]azocin-3-yl)-3-(2-thienyl)cyclobutanol (303 mg), benzoyl chloride (0.12 ml), and pyridine (0.12 ml) were heated and refluxed in methylene chloride (20 ml) for 4 hours. A saturated aqueous sodium bicarbonate solution was added thereto and the whole was extracted with chloroform (30 ml). The concentration residue was purified by silica gel column chromatography (methanol:chloroform=4:96) to obtain trans-3-(5,6,7,8,9,10-hexahydro[1,2,4]triazolo[4,3-a]azocin-3-yl)-3-(2-thienyl)cyclobutyl benzoate (180 mg, Example 43) and cis-3-(5,6,7,8,9,10-hexahydro[1,2,4]triazolo[4,3-a]azocin-3-yl)-3-(2-thienyl)cyclobutyl benzoate (95 mg, Example 44).

Example 45

Methyl 4-[5-(1-anilino-1-methylethyl)-4-methyl-4H-1,2,4-triazol-3-yl]benzoate (300 mg) was dissolved in methanol (1 ml) and then methylamine (30% methanol solution, 886.3 mg) was added thereto, followed by stirring at room temperature overnight. The resulting precipitate was collected by filtration to obtain 349 mg of 4-[5-(1-anilino-1-methylethyl)-4-methyl-4H-1,2,4-triazol-3-yl}benzamide (white crystals).

Example 46

HOBt hydrate (82 mg), WSC hydrochloride (103 mg), and ammonia water (33 μl) were added to a THF (1 ml) and DMF (1 ml) solution of 4-[5-(1-anilino-1-methylethyl)-4-methyl-4H-1,2,4-triazol-3-yl]benzoic acid (150 mg) at room temperature, followed by stirring at the same temperature overnight. After most of the solvent was removed by evaporation under reduced pressure, water was added thereto and the whole was extracted four times with ethyl acetate. The organic layer washed with brine, dried over anhydrous magnesium sulfate, and filtered, and then the solvent was removed by evaporation. Ethyl acetate was added to the resulting white crystals, which was filtered and washed with ethyl acetate to obtain 120 mg of 4-[5-(1-anilino-1-methylethyl)-4-methyl-4H-1,2,4-triazol-3-yl]benzamide (white crystals).

Example 47

Acetic anhydride (37 μl) was added to a pyridine solution (1 ml) of 4-[5-(1-anilino-1-methylethyl)-4-methyl-4H-1,2,4-triazol-3-yl}phenol (60 mg), followed by stirring for 3 hours. After most of acetic anhydride and pyridine was removed by evaporation under reduced pressure, the residue was purified by thin layer chromatography (chloroform:methanol=9:1) to obtain 40 mg of 4-[5-(1-anilino-1-methylethyl)-4-methyl-4H-1,2,4-triazol-3-yl}phenyl acetate (white crystals).

Example 48

Palladium hydroxide was added to a methanol (10 ml) suspension of N-(1-{5-[4-(benzyloxy)-3-chlorophenyl]-4-methyl-4H-1,2,4-triazol-3-yl}-1-methylethyl)aniline (925 mg) and the whole was vigorously stirred under a normal pressure hydrogen atmosphere for 2 hours. After filtration through celite using dioxane (150 ml), methanol (150 ml) and chloroform (150 ml), the solvent was removed by evaporation to obtain a white solid. The resulting solid washed with chloroform and further purified by thin layer chromatography (chloroform:methanol=9:1) to obtain 81.4 mg of 4-[5-(1-anilino-1-methylethyl)-4-methyl-4H-1,2,4-triazol-3-yl}-3-chlorophenol.

Example 49

Triethylamine and ethyl isocyanate were added to a chloroform solution (3 ml) of 4-[5-(1-anilino-1-methylethyl)-4-methyl-4H-1,2,4-triazol-3-yl}phenol (20 mg), followed by stirring at 60° C. for 3 hours. After concentration, a small amount of ethyl acetate was added to the residue and the resulting crystalline powder was filtered to obtain 4-[5-(1-anilino-1-methylethyl)-4-methyl-4H-1,2,4-triazol-3-yl}phenyl ethylcarbamate.

Example 50

3-[3-(Methoxymethoxy)-1-(2-thienyl)cyclobutyl]-5,6,7,8,9,10-hexahydro[1,2,4]triazolo[4,3-a]azocine (343 mg) was dissolved in acetic acid (3 ml) and then N-bromosuccinimide (193 mg) was added, followed by stirring at room temperature for 7 hours under light-shielding. The reaction solution was diluted with chloroform (40 ml) and then washed with water (10 ml), a 1M aqueous sodium hydroxide solution (10 ml), and brine (10 ml). The organic layer was dried and then concentrated under reduced pressure and the resulting residue was purified by silica gel column chromatography (methanol:chloroform=2:98) to obtain 392 mg of 3-[1-(5-bromo-2-thienyl)-3-(methoxymethoxy)cyclobutyl]-5,6,7,8,9,10-hexahydro[1,2,4]triazolo[4,3-a]azocine (reddish purple syrup).

Example 51 cis-3-(5-Bromo-2-thienyl)-3-(5,6,7,8,9,10-hexahydro[1,2,4]triazolo[4,3-a]azocin-3-yl)cyclobutyl benzoate (487 mg) was dissolved in 1-propanol (40 ml) and then [1,1'-bis(diphenylphosphino)ferrocene]dichloropalladium(II) dichloromethane complex (82 mg), potassium vinyltrifluoroborate (402 mg), and triethylamine (0.14 ml) were added thereto, followed by heating and refluxing under a nitrogen atmosphere for 15 hours. The resulting precipitate was removed by filtration and washed with ethanol, and the filtrate was concentrated under reduced pressure. The resulting residue was diluted with brine (30 ml), followed by extraction with chloroform (20 ml×3). The organic layer was dried and then concentrated under reduced pressure and the resulting residue was purified by silica gel chromatography (methanol:chloroform=2:98) to obtain 433 mg of cis-3-(5,6,7,8,9,10-hexahydro[1,2,4]triazolo[4,3-a]azocin-3-yl)-3-(5-vinyl-2-thienyl)cyclobutyl benzoate (yellow solid).

Example 52 cis-3-(5,6,7,8,9,10-Hexahydro[1,2,4]triazolo[4,3-a]azocin-3-yl)-3-(2-thienyl)cyclobutyl benzoate (408 mg) was dissolved in acetic acid (8 ml) and then N-chlorosuccinimide (150 mg) was added, followed by stirring at 80° C. for 5 hours. The reaction solution was diluted with chloroform (40 ml) and then washed with water (10 ml), a 1M aqueous sodium hydroxide solution (10 ml) and brine (10 ml). The organic layer was dried and then concentrated under reduced pressure, and the resulting solid washed with diethyl ether to obtain 398 mg of cis-3-(5-chloro-2-thienyl)-3-(5,6,7,8,9,10-hexahydro[1,2,4]triazolo[4,3-a]azocin-3-yl)cyclobutyl benzoate (white solid).

Example 53 cis-3-(5,6,7,8,9,10-Hexahydro[1,2,4]triazolo[4,3-a]azocin-3-yl)-3-(2-thienyl)cyclobutyl benzoate (204 mg) was suspended in acetic anhydride (3 ml) and then 60% perchloric acid (20 mg) was added thereto, followed by stirring at room temperature for 5 hours. The reaction solution was diluted with a saturated aqueous sodium bicarbonate solution (30 ml), followed by extraction with chloroform (10 ml×3). The organic layer was dried and then concentrated under reduced pressure, and the resulting residue was purified by silica gel chromatography (methanol:ethyl acetate=2:98) to obtain 156 mg of cis-3-(5-acetyl-2-thienyl)-3-(5,6,7,8,9,10-hexahydro[1,2,4]triazolo[4,3-a]azocin-3-yl)cyclobutyl benzoate (pale yellow syrup).

Example 54 cis-3-(5,6,7,8,9,10-Hexahydro[1,2,4]triazolo[4,3-a]azocin-3-yl)-3-(5-vinyl-2-thienyl)cyclobutanol (112 mg) was dissolved in methanol (10 ml) and then 10% palladium-carbon powder (20 mg) was added, followed by stirring under a hydrogen atmosphere at room temperature for 1 hour. The catalyst was removed by filtration through celite and washed with methanol and then the filtrate was concentrated under reduced pressure. The resulting residue was purified by silica gel column chromatography (methanol:chloroform=2:98) and the resulting solid washed with diethyl ether to obtain 90 mg of cis-3-(5-ethyl-2-thienyl)-3-(5,6,7,8,9,10-hexahydro[1,2,4]triazolo[4,3-a]azocin-3-yl)cyclobutanol (white solid).

Example 55

A toluene solution (3.0 ml) of pyrrolidine (0.100 ml) was added to a mixture of 2-{1-[5-(2-bromophenyl)-4-methyl-4H-1,2,4-triazol-3-yl]-1-methylethyl}pyridine (360 mg), sodium tert-butoxide (136 mg), bis(dibenzylideneacetone)dipalladium (23.1 mg) and 2,2'-bis(diphenylphosphino)-1,1'-binaphthyl (31.4 mg) under a nitrogen condition, followed by stirring at 100° C. for 18 hours. The reaction solution was diluted with water (15 ml) and then extracted with ethyl acetate (15 ml). The organic layer washed with brine, dried over anhydrous magnesium sulfate and filtered and then the solvent was removed by evaporation under reduced pressure. The resulting crude product was purified by flash column chromatography (chloroform:methanol=90:10) and further purified by preparative thin layer chromatography (hexane:acetone=1:1) to obtain 81.4 mg of 2-(1-methyl-1-{4-methyl-5-[2-(1-pyrrolidinyl)phenyl]-4H-1,2,4-triazol-3-yl]ethyl}pyridine (pale yellow crystals).

Example 56

A chloroform solution (2.7 ml) of 4-{4-methyl-[5-(1-(2-thienyl)cyclopentyl]-4H-1,2,4-triazol-3-yl}phenol (40 mg), triethylamine (103 μl), and ethyl isocyanate (57 μl) was heated at 60° C. for 5 hours. The solvent was removed by evaporation and a small amount of ethyl acetate was added to the residue. The resulting white solid was collected by filtration and washed with diethyl ether to obtain 4-{4-methyl-[5-(1-(2-thienyl)cyclopentyl]-4H-1,2,4-triazol-3-yl}phenyl ethylcarbamate (30 mg).

Example 57

Trifluoroacetic acid (3 ml) and water (1 ml) were added to a methylene chloride (3 ml) solution of 3-(2-chlorophenyl)-5-[2-(methoxymethoxy)-1,1-dimethyl-2-phenylethyl]-4-methyl-4H-1,2,4-triazole (173 mg) under ice cooling, followed by stirring at room temperature for 19 hours. Then, the whole was stirred at 40° C. for 3.5 hours, at 50° C. for 2.5 hours and at 60° C. for 65 hours. The reaction mixture was concentrated under reduced pressure and ethyl acetate and a saturated sodium hydrogen carbonate solution were added thereto. The organic layer was dried over anhydrous sodium sulfate and then the solvent was removed by evaporation under reduced pressure. The residue was purified by silica gel column chromatography (chloroform:methanol=40:1) to obtain 2-[5-(2-chlorophenyl)-4-methyl-4H-1,2,4-triazol-3-yl]-2-methyl-1-phenylpropan-1-ol (110 mg).

Example 58

Manganese dioxide (955 mg) was gradually added to a methylene chloride (4.8 ml) solution of 2-[5-(2-chlorophenyl)-4-methyl-4H-1,2,4-triazol-3-yl]-2-methyl-1-phenylpropan-1-ol (191 mg) under ice cooling. The reaction mixture was stirred at room temperature for 3 hours and then manganese dioxide (955 mg) was added thereto, followed by stirring at room temperature for another 18.5 hours. Then, the mixture was subjected to filtration through celite. The filtrate was subjected to evaporation under reduced pressure and then purified by silica gel column chromatography (chloroform:

methanol=50:1) to obtain 2-[5-(2-chlorophenyl)-4-methyl-4H-1,2,4-triazol-3-yl]-2-methyl-1-phenylpropan-1-one (140 mg).

Example 59

Diisopropylethylamine (229 μl) and 4-bromobutanoyl chloride (76 μl) were added to a chloroform (10 ml) solution of 2-[5-(2-chlorophenyl)-4-methyl-4H-1,2,4-triazol-3-yl] propan-2-amine (150 mg), followed by stirring at room temperature for 18 hours. Chloroform and a saturated aqueous sodium hydrogen carbonate solution were added to the reaction solution and the organic layer washed with a saturated aqueous sodium chloride solution, dried over anhydrous magnesium sulfate and filtered, followed by evaporation under reduced pressure. The residue was purified by silica gel column chromatography (chloroform:methanol=100:3) to obtain 4-bromo-N-{1-[5-(2-chlorophenyl)-4-methyl-4H-1,2,4-triazol-3-yl]-1-methylethylbutanamide (125 mg). Sodium hydride (16.5 mg) was added to a DMF (10 ml) solution of 4-methyl-4H-1,2,4-triazol-3-yl]-1-methylethylbutanamide (125 mg), followed by stirring at room temperature for 4 hours. Chloroform and water were added to the reaction solution and then the organic layer was washed with a saturated aqueous sodium chloride solution, dried over anhydrous magnesium sulfate, followed by evaporation under reduced pressure. The residue was purified by silica gel column chromatography (chloroform:methanol=25:1) to obtain an oily product. The product was dissolved in ethyl acetate (10 ml) and a 4M hydrogen chloride-ethyl acetate solution (156 μl) was added thereto, followed by stirring for 30 minutes. The precipitated solid was collected by filtration to obtain 1-{1-[5-(2-chlorophenyl)-4-methyl-4H-1,2,4-triazol-3-yl]-1-methylethyl}pyrrolidin-1-one hydrochloride (20 mg) as a brown solid.

Similarly to the methods of the above Examples 1 to 59, compounds of Examples 60 to 227 shown in Tables 17 to 46 below were produced using respective corresponding starting materials. Tables 17 to 46 show structures and physicochemical data of the compounds of Examples.

In addition, Tables 47 to 54 below shows structures of the other compounds of the invention. They are easily produced by the use of the above production methods and the methods described in Examples or methods obvious to those skilled in the art, or modified methods thereof.

TABLE 2

| Rf | RSyn | Structure | Data |
|---|---|---|---|
| 1 | 1 | Me, Cl thiophene-CH2OH | EI: 162 |
| 2 | 2 | Me, Cl thiophene-CH2CN | EI: 171 |
| 7 | 7 | Me-Ph-C(=NMe)(NH-NH2) | ESP: 164 |
| 8 | 8 | Br-CH2-CH(OMOM)-CH2-Br | EI: 261 |
| 16 | 16 | Me-thiazole-CH2CO2Me | ESP: 172 |
| 28 | 28 | (2-CF3—Ph)—C(O)NHMe | FP: 204 |
| 32 | 32 | piperazinone-S(O)2Ph | ESP: 241 |
| 33 | 33 | MeO-dihydropyrazine-S(O)2Ph | ESP: 255 |
| 45 | 2 | Cl-thiophene-CH2CN | NMR2: 3.88 (2H, s), 6.93 (1H, d), 7.28 (1H, d) |
| 46 | 6 | PhS(O)2CH2C(O)NHNH2 | ESP: 215 |
| 47 | 16 | Cl-pyridine-CH2CO2Me | NMR2: 3.02 (3H, s), 3.85 (2H, s), 7.2-7.3 (2H, m), 7.64 (1H, t) |
| 48 | 33 | OMe-dihydropyridine-CO2Et | NMR2: 3.22 (1H, dd), 3.45-3.63 (2H, m), 3.65 (3H, s) |

TABLE 3

| Rf | RSyn | Structure | Data |
|---|---|---|---|
| 49 | 33 | OMe-piperazinone-Et | NMR2: 3.44 (2H, dd), 3.67 (2H, dd), 3.77 (3H, s) |
| 50 | 33 | MeO-diazepine-CO2Bn | NMR2: 2.51-2.69 (2H, brs), 3.46-3.69 (9H, m), 5.15 (2H, s), 7.29-7.46 (5H, m) |

TABLE 4
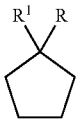
| Rf | RSyn | R¹ | R | Data |
|---|---|---|---|---|
| 3 | 3 | 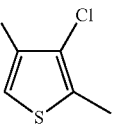 | CN | ESP: 226 |
| 4 | 4 | | CO₂H | FP: 245 |
| 5 | 5 | | —C(O)NHNH₂ | ESP: 259 |
| 10 | 10 | cHex | CN | NMR2: 1.20-1.33 (6H, m), 1.50-1.91 (11H, m), 2.12-2.18 (2H, m) |
| 13 | 13 | | CO₂H | FP: 197 |
| 51 | 20 | | —C(O)NHNH₂ | FP: 211 |
| 11 | 11 | 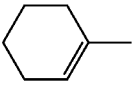 | CN | EI: 175 |
| 18 | 18 | 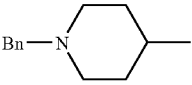 | CO₂Et | FP: 316 |
| 19 | 19 | | CO₂H | FP: 288 |
| 52 | 20 | | —C(O)NHNH₂ | FP: 302 |
| 22 | 22 | BocN— | —C(O)NHNH₂ | FP: 244 |
| 23 | 23 | PhNH— | CN | NMR2: 2.07-2.49 (4H, m), 3.84 (1H, s), 7.26 (2H, dd) |
| 25 | 25 | | CO₂H | NMR1: 1.58-1.80 (4H, m), 1.90-2.24 (4H, m), 7.14 (2H, dd); Sal: HCl |
| 26 | 26 | | —C(O)NHNHBoc | NMR2: 1.47 (9H, s), 3.82 (1H, s), 6.25 (1H, brs), 6.58 (2H, d) |
| 27 | 27 | | —C(O)NHNH₂ | NMR2: 6.50 (1H, d), 6.60 (1H, d), 9.71 (1H, brs) |
| 24 | 24 | PhN(CHO)— | CN | ESP: 215 |
| 53 | 3 | 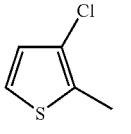 | CN | ESP: 215 |
| 54 | 4 | | CO₂H | FP: 211 |
| 55 | 5 | | —C(O)NHNH₂ | FP: 245 |
| 56 | 3 | 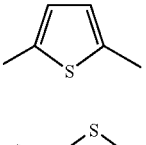 | CN | EI: 211 |
| 57 | 4 | | CO₂H | FN: 229 |
| 58 | 5 | | —C(O)NHNH₂ | FP: 245 |
| 59 | 3 | 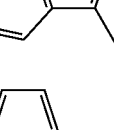 | CN | EI: 227 |
| 60 | 4 | | CO₂H | FN: 245 |
| 61 | 5 | | —C(O)NHNH₂ | ESP: 261 |
| 62 | 5 |  | —C(O)NHNH₂ | ESP: 211 |

TABLE 5

| | | | | |
|---|---|---|---|---|
| 63 | 5 | 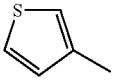 (3-methylthiophene) | —C(O)NHNH$_2$ | FP: 211 |
| 64 | 5 | Bn | —C(O)NHNH$_2$ | ESP: 219 |
| 65 | 6 | 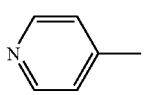 (4-methylpyridine) | —C(O)NHNH$_2$ | EF: 206 |
| 66 | 15 | 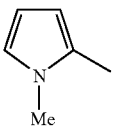 (N-methylpyrrole) | CO$_2$Me | ESP: 208 |
| 67 | 19 | | CO$_2$H | ESP: 194 |
| 68 | 21 | | —C(O)NHNH$_2$ | NMR2: 2.36-2.45 (2H, m), 3.43 (3H, s), 3.79 (2H, d), 6.36 (1H, dd), |
| 69 | 15 | 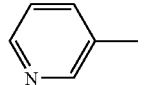 (3-methylpyridine) | CO$_2$Et | ESP: 220 |
| 70 | 22 | | —C(O)NHNH$_2$ | ESP: 206 |
| 71 | 15 | 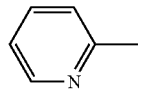 (2-methylpyridine) | CO$_2$Me | ESP: 206 |
| 72 | 22 | | —C(O)NHNH$_2$ | NMR2: 2.20-2.55 (4H, m), 3.77 (2H, d), 7.35 (1H, d) |
| 73 | 15 | 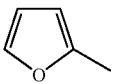 (2-methylfuran) | CO$_2$Et | NMR2: 2.08-2.40 (4H, m), 4.13 (2H, q), 6.15 (1H, m) |
| 74 | 22 | | —C(O)NHNH$_2$ | ESP: 195 |
| 75 | 15 | 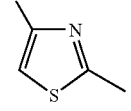 (2,4-dimethylthiazole) | CO$_2$Me | ESP: 226 |
| 76 | 22 | | —C(O)NHNH$_2$ | ESP: 226 |

TABLE 6

| Rf | RSyn | R$^1$ | R | Data |
|---|---|---|---|---|
| 14 | 14 | 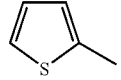 | CO$_2$Me | EI: 196 |
| 77 | 22 | | —C(O)NHNH$_2$ | FP: 197 |
| 78 | 3 | 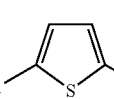 | CN | EI: 197 |
| 79 | 4 | | CO$_2$H | FN: 215 |
| 80 | 5 | | —C(O)NHNH$_2$ | FP: 231 |
| 81 | 14 | BocNH— | CO$_2$Me | FP: 230 |
| 82 | 22 | | —C(O)NHNH$_2$ | FP: 230 |
| 83 | 21 | EtO$_2$C— | —C(O)NHNH$_2$ | FP: 187 |

TABLE 7

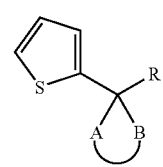

| Rf | RSyn | R | Data |
|---|---|---|---|
| 9 | 9 | CN | EI: 175 |
| 12 | 12 | CO$_2$H | FN: 193 |
| 84 | 14 | CO$_2$Me | EI: 208 |
| 85 | 22 | —C(O)NHNH$_2$ | FP: 209 |

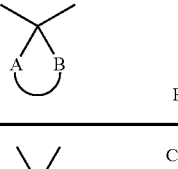

TABLE 7-continued

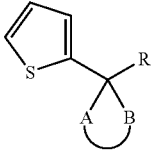

| Rf | RSyn | (structure) | R | Data |
|---|---|---|---|---|
| 86 | 9 | | CN | EI: 193 |
| 87 | 12 | | CO₂H | FN: 211 |
| 20 | 20 | (tetrahydropyran, 4-Me) | —C(O)NHNH₂ | FN: 225 |
| 88 | 9 | | CN | EI: 191 |
| 89 | 12 | | CO₂H | FN: 209 |
| 21 | 21 | (cyclobutane, 3,3-diMe) | —C(O)NHNH₂ | FP: 225 |
| 90 | 9 | | CN | EI: 223 |
| 91 | 12 | | CO₂H | FN: 241 |
| 92 | 21 | (cyclobutane, OMOM) | —C(O)NHNH₂ | FP: 257 |
| 93 | 9 | | CN | EI: 149 |
| 94 | 12 | | CO₂H | FN: 167 |
| 95 | 20 | (cyclopropane) | —C(O)NHNH₂ | FP: 183 |

TABLE 7-continued

| Rf | RSyn | (structure) | R | Data |
|---|---|---|---|---|
| 96 | 9 | | CN | EI: 219 |
| 97 | 12 | | CO₂H | FP: 239 |
| 98 | 20 | (cyclobutane, 3,3-diEt) | —C(O)NHNH₂ | FP: 253 |
| 99 | 15 | | CO₂Me | EI: 224 |
| 100 | 22 | (cyclohexane) | —C(O)NHNH₂ | FP: 225 |
| 101 | 15 | | CO₂Me | FP: 297 |
| 102 | 22 | (dioxaspiro) | —C(O)NHNH₂ | FP: 297 |

TABLE 8

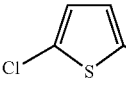

| Rf | RSyn | R¹ | R | Data |
|---|---|---|---|---|
| 6 | 6 | (thiophene) | —C(O)NHNH₂ | ESP: 185 |
| 17 | 17 | PhNH— | CO₂Et | ESP: 208 |
| 103 | 22 | | —C(O)NHNH₂ | ESP: 194 |
| 34 | 34 | | CO₂tBu | EI: 190(M-tBu) |
| 35 | 35 | (=CH₂, Ph) | CO₂H | EI: 190 |
| 104 | 21 | | —C(O)NHNH₂ | FP: 205 |
| 44 | 44 | OMOM | CO₂Et | FP: 267 |
| 105 | 19 | | CO₂H | FP: 239 |
| 106 | 21 | (Ph) | —C(O)NHNH₂ | FP: 253 |
| 107 | 4 | | CO₂H | FN: 203 |
| 108 | 5 | (5-Cl-thiophene) | —C(O)NHNH₂ | FP: 219 |

TABLE 8-continued

| Rf | RSyn | R¹ | R | Data |
|---|---|---|---|---|
| 109 | 4 | 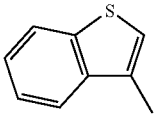 | CO₂H | FP: 221 |
| 110 | 5 |  | —C(O)NHNH₂ | FP: 235 |
| 111 | 5 | 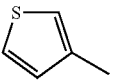 | —C(O)NHNH₂ | EP: 185 |
| 112 | 5 | Bn | —C(O)NHNH₂ | ESP: 193 |
| 113 | 6 | PhO— | —C(O)NHNH₂ | ESP: 195 |
| 114 | 15 | 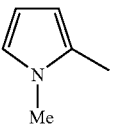 | CO₂Me | ESP: 182 |
| 115 | 22 |  | —C(O)NHNH₂ | NMR2: 1.56 (6H, s), 3.47 (3H, s), 6.05 (1H, dd) |
| 116 | 17 | (2-Cl—Ph)—NH— | CO₂Et | EI: 241 |
| 117 | 22 |  | —C(O)NHNH₂ | EF: 228 |
| 118 | 17 | (2-Cl—Ph)—O— | CO₂Et | FP: 243 |
| 119 | 22 |  | —C(O)NHNH₂ | FP: 229 |
| 120 | 17 | 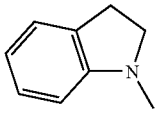 | CO₂Et | FP: 234 |
| 121 | 19 |  | CO₂H | ESP: 206 |
| 122 | 21 |  | —C(O)NHNH₂ | FP: 220 |
| 123 | 17 | (2-Me—Ph)—NH— | CO₂Et | NMR2: 1.57 (3H, s), 1.59 (3H, s), 2.17 (3H, s), 6.47 (1H, d) |
| 124 | 22 |  | —C(O)NHNH₂ | ESP: 208.37 |
| 125 | 17 | (4-Me—Ph)—NH— | CO₂Et | NMR2: 1.53 (6H, s), 2.23 (3H, s), 6.53 (2H, d), |
| 126 | 22 |  | —C(O)NHNH₂ | ESP: 208.37 |

TABLE 9

| 127 | 17 | (2-Me-3-Cl—Ph)—NH— | CO₂Et | NMR2: 1.59 (6H, s), 2.24 (3H, s), 6.37 (1H, d), |
|---|---|---|---|---|
| 128 | 22 |  | —C(O)NHNH₂ | NMR2: 1.55 (6H, s), 2.25 (3H, s), 6.29 (1H, d) |
| 129 | 22 | 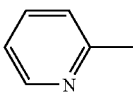 | —C(O)NHNH₂ | ESP: 180 |
| 130 | 15 | 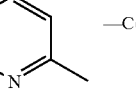 | CO₂Et | ESP: 208 |
| 131 | 22 |  | —C(O)NHNH₂ | ESP: 194 |
| 132 | 21 | EtO₂C— | —C(O)NHNH₂ | ESP: 175 |
| 133 | 15 | 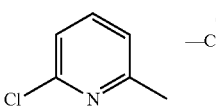 | CO₂Me | NMR2: 1.60 (6H, s), 3.69 (3H, s), 7.22 (2H, d), 7.60 (1H, t) |
| 134 | 22 |  | —C(O)NHNH₂ | NMR2: 1.63 (6H, s), 3.84 (2H, brs), 7.22 (1H, d), 7.32 (1H, d), 7.64 (1H, t), 7.66 (1H, brs) |

TABLE 10

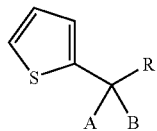

| Rf | RSyn | A | B | R | Data |
|---|---|---|---|---|---|
| 15 | 15 | nPr | nPr | CO$_2$Et | EI: 254 |
| 135 | 19 | | | CO$_2$H | FP: 227 |
| 136 | 20 | | | —C(O)NHNH$_2$ | FP: 241 |
| 137 | 9 | Et | Et | CN | EI: 179 |
| 138 | 12 | | | CO$_2$H | FN: 197 |
| 139 | 20 | | | —C(O)NHNH$_2$ | FP: 213 |
| 140 | 15 | —(CH$_2$)$_2$OMe | —(CH$_2$)$_2$OMe | CO$_2$Et | FP: 287 |
| 141 | 22 | | | —C(O)NHNH$_2$ | FP: 273 |
| 142 | 15 | —(CH$_2$)$_2$OMOM | —(CH$_2$)$_2$OMOM | CO$_2$Me | FP: 333 |
| 143 | 22 | | | —C(O)NHNH$_2$ | EF: 333 |

TABLE 11

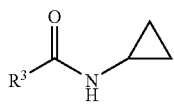

| Rf | RSyn | R$^3$ | Data |
|---|---|---|---|
| 29 | 29 | 3-MeO$_2$C—Ph | NMR2: 0.61-0.95 (4H, m), 3.95 (3H, s), 8.31 (1H, s) |
| 30 | 30 | 4-HO—Ph | NMR1: 0.48-0.72 (4H, m), 6.76 (2H, d), 9.93 (1H, s) |
| 31 | 31 | 4-BnO—Ph | ESP: 268 |
| 144 | 28 | 2-CF$_3$—Ph | FP: 230 |
| 145 | 28 | 4-MeO$_2$C—Ph | NMR2: 0.61-0.96 (4H, m), 3.95 (3H, s), 8.10 (2H, d) |

TABLE 12

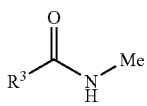

| Rf | RSyn | R | Data |
|---|---|---|---|
| 36 | 36 | —(CH$_2$)$_2$NH$_2$ | NMR1: 2.88-3.02 (2H, m), 3.43-3.56 (2H, m), 7.35-7.64 (4H, m), 8.10 (3H, br), 8.60-8.71 (1H, m) |
| 37 | 37 | —(CH$_2$)$_2$NHMs | ESP: 277 |
| 146 | 30 | —(CH$_2$)$_2$NHBoc | NMR2: 1.43 (9H, s), 3.33-3.46 (2H, m), 3.52-3.65 (2H, m), 4.94 (1H, br), 6.68 (1H, br), 7.27-7.45 (3H, m), 7.62 (1H, m) |

TABLE 13

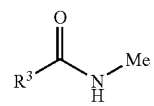

| Rf | RSyn | R$^3$ | Data |
|---|---|---|---|
| 147 | 28 | 4-MeO$_2$C—Ph | ESP: 194 |
| 148 | 30 | 4-BnO—Ph | ESP: 242 |

TABLE 13-continued

| Rf | RSyn | R$^3$ | Data |
|---|---|---|---|
| 149 | 30 | 3-BnO—Ph | ESP: 242 |
| 150 | 30 | 3-Cl-4-BnO—Ph | ESP: 276 |

TABLE 14

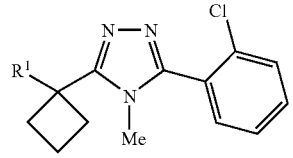

| Rf | RSyn | R$^1$ | Data |
|---|---|---|---|
| 41 | 41 | EtO$_2$C— | ESP: 320 |
| 42 | 42 | HO$_2$C— | ESP: 292 |
| 151 | 39 | BocHN— | FP: 363 |
| 152 | 40 | H$_2$N— | FP: 263; Sal: 2HCl |

TABLE 15

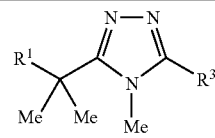

| Rf | RSyn | R$^1$ | R$^3$ | Data |
|---|---|---|---|---|
| 38 | 38 | OHC— | 2-Cl—Ph | ESP: 264 |
| 39 | 39 | BocHN— | 2-Me—Ph | FP: 331 |
| 40 | 40 | H$_2$N— | 2-Me—Ph | FP: 231; Sal: 2HCl |
| 43 | 43 | EtNH— | 2-Cl—Ph | NMR2: 1.67 (6H, s), 2.47 (2H, q), 3.73 (3H, s) |
| 153 | 39 | BocHN— | 2-Cl—Ph | FP: 351 |
| 154 | 40 | H$_2$N— | 2-Cl—Ph | FP: 251; Sal: 2HCl |
| 155 | 41 | EtO$_2$C— | 2-Cl—Ph | ESP: 308 |
| 156 | 42 | HO$_2$C— | 2-Cl—Ph | ESP: 280 |

TABLE 16

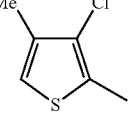

| Rf | RSyn | R¹ | Data |
|---|---|---|---|
| 157 | 39 | BocHN— | FP: 357 |
| 158 | 39 | H₂N— | FP: 257 |

TABLE 17

| Ex | Syn | R¹ | Data |
|---|---|---|---|
| 1 | 1 | 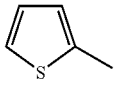 | NMR1: 1.18-1.25 (2H, m), 1.48-1.54 (2H, m), 1.62-1.82 (6H, m), 2.06 (3H, d), 2.06-2.15 (2H, m), 2.58-2.66 (2H, m), 2.81-2.84 (2H, m), 3.62-3.64 (2H, m), 7.28 (1H, d); FP: 336 |
| 2 | 2 | PhS(O)₂— | NMR1: 1.63-1.87 (10H, m), 2.40-2.48 (2H, m), 2.59-2.70 (2H, m), 3.15-3.18 (2H, m), 4.41-4.47 (2H, m), 7.53-7.61 (4H, m), 7.76-7.80 (1H, m); FP: 346; Sal: HCl |
| 60 | 1 | 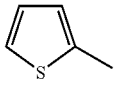 | NMR1: 1.25-1.31 (2H, m), 1.49-1.55 (2H, m), 1.66-1.80 (6H, m), 2.18-2.24 (2H, m), 2.50-2.56 (2H, m), 2.81-2.84 (2H, m), 3.70-3.73 (2H, m), 6.86 (1H, dd), 6.95 (1H, dd), 7.40 (1H, dd); FP: 288 |
| 61 | 1 | 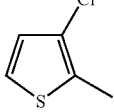 | NMR2: 1.34-1.39 (2H, m), 1.65-1.77 (4H, m), 1.79-1.93 (4H, m), 2.22-2.28 (2H, m), 2.71-2.77 (2H, m), 2.92-2.96 (2H, m), 3.63-3.66 (2H, m), 6.83 (1H, d), 7.14 (1H, dd); FP: 322 |
| 62 | 1 | 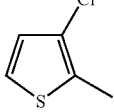 | NMR1: 1.33-1.40 (2H, m), 1.50-1.57 (2H, m), 1.64-1.79 (6H, m), 2.16-2.23 (2H, m), 2.47-2.53 (2H, m), 2.82-2.85 (2H, m), 3.76-3.79 (2H, m), 6.78 (1H, d), 6.96 (1H, d); FP: 322 |
| 63 | 1 | 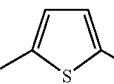 | NMR2: 1.27-1.36 (2H, m), 1.62-1.76 (4H, m), 1.77-1.90 (4H, m), 2.17-2.27 (2H, m), 2.52-2.63 (2H, m), 2.87-2.97 (2H, m), 3.58-3.68 (2H, m), 6.80 (1H, m), 6.97 (1H, m), 7.24 (1H, m); FP: 288 |
| 64 | 1 | 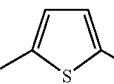 | NMR1: 0.71-0.85 (2H, m), 1.29-1.37 (2H, m), 1.45-1.51 (2H, m), 1.73-1.80 (4H, m), 2.28-2.38 (2H, m), 2.58-2.68 (2H, m), 2.73-2.76 (2H, m), 3.64-3.67 (2H, m), 7.17-7.21 (1H, m), 7.26-7.30 (1H, m), 7.36 (1H, d), 7.83 (1H, s), 7.94 (1H, d); FP: 338 |

TABLE 17-continued

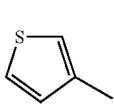

| Ex | Syn | R¹ | Data |
|---|---|---|---|
| 65 | 1 | 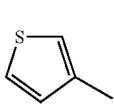 | NMR2: 1.24-1.35 (2H, m), 1.64-1.76 (4H, m), 1.78-1.94 (4H, m), 2.16-2.27 (2H, m), 2.56-2.67 (2H, m), 2.90-2.98 (2H, m), 3.45-3.52 (2H, m), 7.09 (2H, dd), 8.53 (2H, dd); FP: 283 |
| 66 | 1 | Bn | NMR1: 1.52-1.92 (12H, m), 2.05-2.12 (2H, m), 2.85-2.88 (2H, m), 2.91 (2H, s), 4.10-4.12 (2H, m), 6.72-6.74 (2H, m), 7.13-7.18 (3H, m); FP: 296 |
| 67 | 6 | cHex | FP: 288 |

TABLE 18

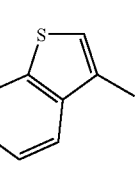

| Ex | Syn | R¹ | Data |
|---|---|---|---|
| 5 | 5 | 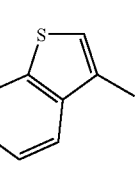 | FP: 393 |
| 6 | 6 | cHex | NMR1: 0.86-1.17 (5H, m), 1.35-1.86 (20H, m), 2.22-2.28 (2H, m), 2.78-2.81 (2H, m), 4.08-4.11 (2H, m); FP: 302 |
| 20 | 20 | 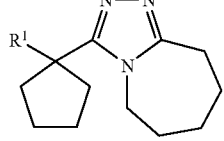 | FP: 381 |
| 27 | 27 | 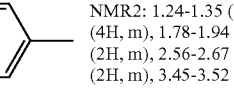 | FP: 317 |
| 40 | 40 | 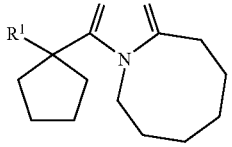 | ESP: 303 |
| 68 | 1 | 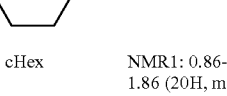 | NMR1: 0.94-0.99 (2H, m), 1.07-1.13 (2H, m), 1.25-1.30 (2H, m), 1.59-1.65 (2H, m), 1.68-1.76 (4H, m), 2.27-2.33 (2H, m), 2.48-2.55 (2H, m), 2.76-2.79 (2H, m), 3.81-3.84 (2H, m), 6.95-6.99 (2H, m), 7.41 (1H, dd); FP: 302 |
| 69 | 1 | 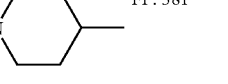 | NMR2: 1.01-1.07 (2H, m), 1.24-1.30 (2H, m), 1.37-1.42 (2H, m), 1.76-1.92 (6H, m), 2.32-2.38 (2H, m), 2.73-2.80 (2H, m), 2.83-2.86 (2H, m), 3.71-3.74 (2H, m), 6.85 (1H, d), 7.17 (1H, d); FP: 336 |

TABLE 18-continued

| Ex | Syn | R¹ | Data |
|---|---|---|---|
| 70 | 1 | 5-chloro-2-methylthiophene | NMR1: 1.13-1.19 (4H, m), 1.27-1.33 (2H, m), 1.60-1.66 (2H, m), 1.69-1.73 (4H, m), 2.26-2.32 (2H, m), 2.44-2.48 (2H, m), 2.76-2.80 (2H, m), 3.83-3.88 (2H, m), 6.88 (1H, d), 6.97 (1H, d); FP: 336 |
| 71 | 1 | 4-methylpyridine | NMR2: 1.03-1.11 (2H, m), 1.15-1.24 (2H, m), 1.31-1.40 (2H, m), 1.74-1.83 (2H, m), 1.84-1.93 (4H, m), 2.25-2.35 (2H, m), 2.57-2.67 (2H, m), 2.80-2.86 (2H, m), 3.56-3.62 (2H, m), 7.12-7.16 (2H, m), 8.50-8.55 (2H, m); FP: 297 |
| 72 | 5 | 2-methylpyridine | ESP: 297 |
| 73 | 5 | 3-methylpyridine | ESP: 297 |
| 74 | 5 | 2-methylfuran | NMR2: 2.84 (2H, t), 3.75 (2H, t), 6.14-6.16 (1H, m); ESP: 286 |

TABLE 19

| Ex | Syn | R¹ | Data |
|---|---|---|---|
| 75 | 5 | 1-methyl-2-methylpyrrole | NMR2: 2.83 (2H, t), 3.24 (3H, s), 3.73 (2H, t), 6.04 (1H, t); ESP: 299 |
| 76 | 5 | 3-chloro-2,4-dimethylthiophene | FP: 350 |
| 77 | 5 | 2,4-dimethylthiazole | ESP: 317 |

TABLE 20

| Ex | Syn | A,B | Data |
|---|---|---|---|
| 7 | 7 | 3,3-bis(hydroxymethyl)-1,1-dimethylcyclobutane | FP: 348 |
| 8 | 8 | 3,3-bis(methoxymethyl)-1,1-dimethylcyclobutane | FP: 376; Sal: HCl |
| 9 | 9 | cis-diol dimethylcyclopentane | FP: 334 |
| 10 | 10 | dimethoxy dimethylcyclopentane | FP: 362 |
| 11 | 11 | 3-hydroxy-1,1-dimethylcyclobutane | NMR1: 0.77-0.84, 0.99-1.13 (4H, m), 1.21-1.30 (2H, m), 1.58-1.64 (2H, m), 2.42-2.50, 2.71-2.79 (4H, m), 2.92-2.98, 3.23-3.28 (2H, m), 3.67-3.74 (2H, m), 3.96-4.06 (1H × 7/20, m), 4.29-4.39 (1H × 13/20, m), 5.29-5.32 (1H, m), 6.92 (1H × 7/20, dd), 6.96-6.98 (1H, m), 7.09 (1H × 13/20, dd), 7.40-7.43 (1H, m); FP: 304 |
| 12 | 12 | 3-oxo-1,1-dimethylcyclobutane | FP: 300 |
| 42 | 42 | 3-(methoxymethoxy)-1,1-dimethylcyclobutane | FP: 348 |
| 78 | 5 | spiro[2.2]pentane | FP: 274 |

TABLE 20-continued

[Structure: thiophene-C(A)(B)-triazolo-azocine core]

[Structure: C(A)(B) with two methyl groups]

| Ex | Syn | [A-B group] | Data |
|---|---|---|---|
| 79 | 5 | cyclobutyl (spiro) | NMR1: 0.90-0.96 (2H, m), 1.04-1.12 (2H, m), 1.23-1.29 (2H, m), 1.59-1.65 (2H, m), 1.89-1.99 (1H, m), 2.05-2.16 (1H, m), 2.55-2.62 (2H, m), 2.77 (2H, dd), 2.91-2.99 (2H, m), 3.68 (2H, t), 7.00 (1H, dd), 7.07 (1H, dd), 7.44 (1H, dd); FP: 288 |

TABLE 21

| Ex | Syn | [A-B group] | Data |
|---|---|---|---|
| 80 | 5 | 3,3-dimethylcyclobutyl | NMR1: 0.84-0.90 (2H, m), 1.04 (3H, s), 1.05-1.11 (2H, m), 1.17 (3H, s), 1.21-1.26 (2H, m), 1.58-1.65 (2H, m), 2.55 (2H, d), 2.77 (2H, t), 2.92 (2H, d), 3.69 (2H, t), 6.97 (1H, dd), 7.02 (1H, dd), 7.42 (1H, dd); FP 316 |
| 81 | 5 | 3,3-diethylcyclobutyl | FP: 344 |
| 82 | 5 | spiro dioxane-cyclobutyl with Me, Me | FP: 388 |
| 83 | 5 | spiro cyclopentenyl-cyclobutyl | NMR1 1.00-1.06 (2H, m), 1.09-1.15 (2H, m), 1.27-1.33 (2H, m), 1.60-1.66 (2H, m), 2.77-2.80 (2H, m), 3.03 (2H, d), 3.44 (2H, d), 3.79 (2H, t), 5.77 (2H, br s), 6.84 (1H, dd), 6.93 (1H, dd), 7.38 (1H, dd); FP: 300 |
| 84 | 5 | cyclohexyl | NMR1: 1.09-1.66 (14H, m), 1.99-2.06 (2H, m), 2.48-2.58 (2H, m), 2.76-2.79 (2H, m), 3.74-3.78 (2H, m), 6.90-6.97 (2H, m), 7.40(1H, dd); FP: 316 |
| 85 | 5 | tetrahydropyranyl | FP: 318 |

TABLE 22

[Structure: R¹-C(A)(B)-triazolo-azocine core]

[Structure: R¹-C(A)(B) generic]

| Ex | Syn | [R¹ and A-B group] | Data |
|---|---|---|---|
| 37 | 37 | 5-Br-thienyl, cyclobutyl | NMR1: 1.02-1.22(4H, m), 1.23-1.37(2H, m), 1.56-1.70 (2H, m), 1.84-2.01(1H, m), 2.02-2.20(1H, m), 2.52-2.65(2H, m), 2.79 (2H, t), 2.87-3.01(2H, m), 3.72 (2H, t), 6.97 (1H, d), 7.12(1H, d); ESP: 368 |
| 50 | 50 | 5-Br-thienyl, 3-OMOM-cyclobutyl | ESP: 428 |

TABLE 22-continued
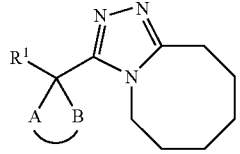
| Ex | Syn | 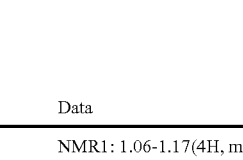 | Data |
|---|---|---|---|
| 86 | 1 | 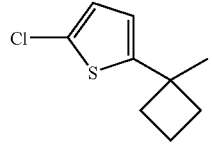 | NMR1: 1.06-1.17(4H, m), 1.27-1.32(2H, m), 1.60-1.66 (2H, m), 1.88-1.98(1H, m), 2.05-2.16(1H, m), 2.55-2.61 (2H, m), 2.77-2.80(2H, m), 2.89-2.96(2H, m), 3.71-3.74 (2H, m), 7.00(1H, d), 7.02(1H, d); FP: 322 |
| 87 | 11 | 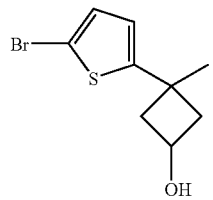 | FP: 382 |
TABLE 23
| Ex | Syn | Structure | Data |
|---|---|---|---|
| 13 | 13 | 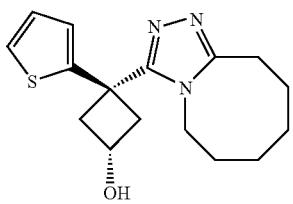 | FP: 304 |
| 43 | 43 | 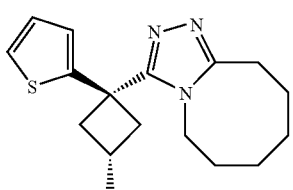 | FP: 408 |
TABLE 24
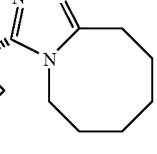
| Ex | Syn | R$^1$ | Data |
|---|---|---|---|
| 44 | 44 | 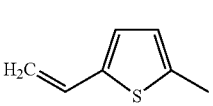 | FP: 408 |
| 51 | 51 | 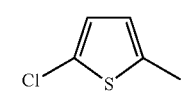 | ESP: 434 |
| 52 | 52 |  | ESP: 442 |

TABLE 24-continued

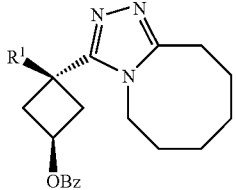

| Ex | Syn | R¹ | Data |
|---|---|---|---|
| 53 | 53 | 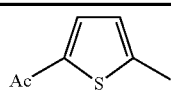 (5-Ac thiophene-2-methyl) | ESP: 450 |
| 88 | 44 | 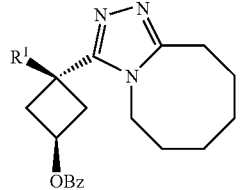 (5-Br thiophene-2-methyl) | FP: 488 |

TABLE 25

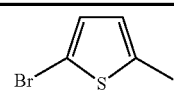

| Ex | Syn | R¹ | Data |
|---|---|---|---|
| 54 | 54 | 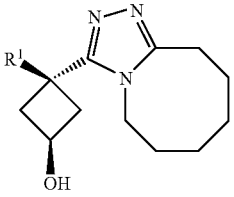 (5-Et thiophene-2-methyl) | ESP: 332 |
| 89 | 13 | 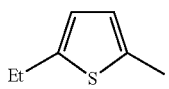 (thiophen-2-yl) | NMR1: 0.75-0.86(2H, m), 1.00-1.14(2H, m), 1.18-1.32 (2H, m), 1.55-1.68(2H, m), 2.40-2.51(2H, m), 2.72-2.82 (2H, m), 3.20-3.29(2H, m), 3.67-3.77(2H, m), 3.95-4.07 (1H, m), 5.24-5.46(1H, br), 6.92(1H, dd), 6.98(1H, dd), 7.41(1H, dd) ; FP: 304 |
| 90 | 13 |  (5-Br thiophene-2-methyl) | NMR1: 0.94-1.04(2H, m), 1.08-1.19(2H, m), 1.22-1.33 (2H, m), 1.58-1.69(2H, m), 2.39-2.49(2H, m), 2.76-2.84 (2H, m), 3.19-3.28(2H, m), 3.71-3.81(2H, m), 3.94-4.06 (1H, m), 5.35(1H, d), 6.80(1H, d), 7.10(1H, d).; FP: 384 |
| 91 | 13 | 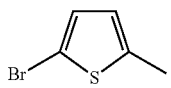 (5-Cl thiophene-2-methyl) | NMR1: 0.92-1.05(2H, m), 1.09-1.20(2H, m), 1.23-1.34 (2H, m), 1.57-1.69(2H, m), 2.40-2.49(2H, m), 2.75-2.84 (2H, m), 3.17-3.28(2H, m), 3.72-3.81(2H, m), 3.95-4.06 (1H, m), 5.36(1H, d), 6.85(1H, d); FP: 338 |
| 92 | 13 | 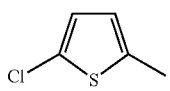 (5-vinyl thiophene-2-methyl) | NMR1: 0.89-1.03(2H, m), 1.06-1.18(2H, m), 1.20-1.33 (2H, m), 1.57-1.70(2H, m), 2.39-2.49(2H, m), 2.74-2.84 (2H, m), 3.18-3.30(2H, m), 3.69-3.80(2H, m), 3.94-4.08 (1H, m), 5.08(1H, d), 5.34(1H, d), 5.39(1H, d), 6.78(1H, dd), 6.83(1H, d), 6.95(1H, d).; ESP: 330 |
| 93 | 13 | 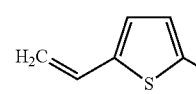 (5-Ac thiophene-2-methyl) | ESP: 346 |

TABLE 26
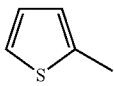
| Ex | Syn | R¹ | Data |
|---|---|---|---|
| 94 | 1 | 2-thienyl | NMR1: 1.40-1.46(2H, m), 1.61-1.79(4H, m), 1.81(6H, s), 3.15-3.17 (2H, m), 3.87-3.89(2H, m), 7.02-7.08(2H, m), 7.54-7.56 (1H, m); FP: 262; Sal:HCl |
| 95 | 1 | 5-chloro-2-thienyl | NMR1: 1.37-1.42(2H, m), 1.50-1.59(2H, m), 1.66-1.73(2H, m), 1.72(6H, s), 2.83-2.86(2H, m), 3.71-3.74(2H, m), 6.79(1H, d), 6.99(1H, d); FP: 296 |
| 96 | 1 | 3-thienyl | NMR1: 1.34-1.43(2H, m), 1.67-1.74(8H, m), 2.43-2.52(2H, m), 3.09-3.16(2H, m), 3.78-3.83(2H, m), 7.00(1H, d), 7.48(1H, m), 7.61(1H, dd); FP: 262; Sal:HCl |
| 97 | 1 | 3-benzothienyl | NMR2: 0.72-0.94(2H,m), 1.46-1.62(4H, m), 1.94(6H, s), 2.80-2.94 (2H, m), 3.40-3.52(2H, m), 7.12-7.23(2H, m), 7.27(1H, m), 7.37(1H, s),7.82(1H, d); FP: 312 |
| 98 | 1 | Bn | NMR1: 1.41(6H, s), 1.70-1.78(2H, m), 1.80-1.90(4H, m), 3.06 (2H, s), 3.17-3.20(2H, m), 4.57-4.62(2H, m), 7.00(2H, dd), 7.20-7.28 (3H, m); FP: 270; Sal:HCl |
| 99 | 1 | PhO— | NMR1: 1.58-1.64(2H, m), 1.66-1.84(4H, m), 1.75(6H, s), 3.19-3.22 (2H, m), 4.53-4.55(2H, m), 6.76-6.79(2H, m), 7.07(1H, t), 7.25-7.30(2H, m); FP: 272; Sal:HCl |
TABLE 27
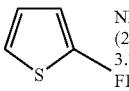
| Ex | Syn | R¹ | Data |
|---|---|---|---|
| 100 | 5 | 2-thienyl | NMR1: 0.95-1.01(2H, m), 1.08-1.13(2H, m), 1.26-1.31 (2H, m), 1.59-1.65(2H, m), 1.79(6H, s), 2.75-2.78(2H, m), 3.75-3.78(2H, m), 6.96-6.99(2H, m), 7.42-7.44(1H, m); FP: 276 |
| 101 | 5 | PhNH— | FP: 285 |
| 102 | 15 | PhN(Me)— | NMR1: 1.22-1.40(4H, m), 1.48(6H, s), 1.64-1.74(4H, m), 2.64(3H, s), 2.82-2.85(2H, m), 4.32-4.35(2H, m), 6.94-6.98 (3H, m), 7.19-7.23(2H, m); FP: 299 |

TABLE 28

[Structure: 4-methyl-3-(2-methylphenyl)-5-(1-R¹-cyclopentyl)-4H-1,2,4-triazole]

| Ex | Syn | R¹ | Data |
|---|---|---|---|
| 3 | 3 | 2-thienyl | NMR1: 1.73-1.86(4H, m), 2.07(3H, s), 2.26-2.32(2H, m), 2.62-2.68(2H, m), 2.99(3H, s), 6.93(1H, dd), 6.97(1H, dd), 7.30-7.46(5H, m); FP: 324 |
| 22 | 22 | PhNHC(O)NH— | FP: 376 |
| 23 | 23 | BzNH— | FP: 361 |
| 103 | 14 | Bn | FP: 332; Sal:HCl |
| 104 | 14 | 1-benzyl-4-piperidinyl (Bn—N, 4-Me) | FP: 415; Sal:HCl |
| 105 | 20 | PhS(O)₂NH— | FP: 397 |

TABLE 29

[Structure: 3-(2-chlorophenyl)-4-methyl-5-(1-R¹-cyclopentyl)-4H-1,2,4-triazole]

| Ex | Syn | R¹ | Data |
|---|---|---|---|
| 41 | 41 | 4-methylpiperidin-4-yl (HN) | ESP: 345 |
| 106 | 2 | PhS(O)₂— | FP: 402; Sal:HCl |
| 107 | 14 | 2-thienyl | NMR1: 1.72-1.86(4H, m), 2.27-2.33(2H, m), 2.60-2.67(2H, m), 3.03(3H, s), 6.91-6.99(2H, m), 7.44-7.67(5H, m); FP: 344 |
| 108 | 14 | Bn | FP: 352 |
| 109 | 14 | PhNH— | NMR2: 3.51(3H, s), 3.90(1H, s), 6.51(2H, d), 7.34-7.51(4H, m); ESP: 353 |
| 110 | 14 | 1-benzyl-4-methylpiperidin-4-yl | FP: 435; Sal:HCl |
| 111 | 20 | 1-(phenylsulfonyl)-4-methylpiperidin-4-yl | FP: 485 |
| 112 | 20 | 1-(methylsulfonyl)-4-methylpiperidin-4-yl (Ms—N) | FP: 423 |
| 113 | 20 | PhS(O)₂NH— | NMR2: 1.63-1.77(4H, m), 1.94-2.08(2H, m), 2.36-2.49(2H, m), 3.54(3H, s), 5.18(1H, s), 7.38-7.62(7H, m), 7.79-7.84(2H, m); ESP: 417.43 |
| 114 | 20 | (4-MeO—Ph)—S(O)₂NH— | NMR2: 1.64-1.78(4H, m), 1.94-2.07(2H, m), 2.36-2.49(2H, m), 3.54(3H, s), 3.87(3H, s), 4.99(1H, s), 6.95(2H, d, J=3.0 Hz), 7.36-7.54(4H, m), 7.72(2H, d, J=3.0 Hz); ESP: 447.39 |

TABLE 29-continued

| Ex | Syn | R¹ | Data |
|---|---|---|---|
| 115 | 21 | PhS(O)₂N(Me)13 | NMR2: 1.40-1.64(4H, m), 1.84-1.99(2H, m), 2.61-2.72(2H, m), 2.94(3H, s), 3.68(3H, s), 7.38-7.68(7H, m), 7.85-7.92 (2H, m); ESP: 431.38 |
| 116 | 23 | (adamantyl-C(O)NH-Me) | NMR2: 1.62-1.95(16H, m), 2.00-2.07(3H, m), 2.39-2.54 (4H, m), 3.59(3H, s), 5.82(1H, s), 7.35-7.59(4H, m) |

TABLE 30

| Ex | Syn | R³ | Data |
|---|---|---|---|
| 19 | 19 | 2-Cl-4-HO-Ph | NMR1: 1.70-1.85(4H, m), 2.25-2.32(2H, m), 2.57-2.66 (2H, m), 3.01(3H, s), 6.85-6.98(4H, m), 7.31(1H, d), 7.44 (1H, d), 10.44(1H, s); FP: 360 |
| 56 | 56 | 4-EtNHC(O)O—Ph | NMR1: 7.86(1H, t), 3.11(2H, m), 1.10(3H, t); ESP: 397 |
| 117 | 14 | 4-BnO—Ph | ESP: 416 |
| 118 | 14 | Ph | NMR1: 1.73-1.85(4H, m), 2.28-2.34(2H, m), 2.63-2.69 (2H, m), 3.32(3H, s), 6.93(1H, dd), 6.97(1H, dd), 7.43(1H, dd), 7.51-7.54(3H, m), 7.63-7.66(2H, m); FP: 310 |
| 119 | 14 | 2-CF₃—Ph | NMR1: 1.72-1.85(4H, m), 2.24-2.32(2H, m), 2.61-2.68 (2H, m), 2.96(3H, s), 6.88(1H, dd), 6.97(1H, dd), 7.45(1H, dd), 7.63(1H, d), 7.78-7.86(2H, m), 7.93-7.96(1H, m) FP: 378 |
| 120 | 14 | 2-Cl-4-MeO—Ph | NMR1: 1.76-1.82(4H, m), 2.26-2.32(2H, m), 2.59-2.66 (2H, m), 3.02(3H, s), 3.84(3H, s), 6.90-6.91(1H, m), 6.96-6.98 (1H, m), 7.05-7.08(1H, m), 7.28(1H, d), 7.43-7.46(2H, m); FP: 374 |
| 121 | 32 | 4-HO—Ph | NMR1: 6.88(1H, d), 7.43(2H, d), 9.93(1H, s); ESP: 326 |

TABLE 31

| Ex | Syn | R¹ | R³ | Data |
|---|---|---|---|---|
| 14 | 14 | 2-methylthiophene | 2-Me—Ph | NMR1: 0.01-0.06(2H, m), 0.48-0.53(2H, m), 1.76-1.83(4H, m), 2.11(3H, s), 2.40-2.48(2H, m), 2.65-2.72(2H, m), 2.83-2.89(1H, m), 6.93 (1H, dd), 6.96(1H, dd), 7.27-7.35(3H, m), 7.38-7.43(2H, m); FP: 350 |

TABLE 31-continued

[Structure: 1,2,4-triazole with R¹-substituted cyclopentyl at position 3, R³ at position 5, cyclopropyl on N4]

| Ex | Syn | R¹ | R³ | Data |
|---|---|---|---|---|
| 122 | 14 | | Ph | NMR1: −0.03-0.01(2H, m), 0.66-0.72(2H, m), 1.75-1.82(4H, m), 2.44-2.50(2H, m), 2.65-2.72 (2H, m), 3.24-3.30(1H, m), 6.92(1H, dd), 6.95 (1H, dd), 7.39(1H, dd), 7.48-7.51(3H, m), 7.68-7.72(2H, m); FP: 336 |
| 123 | 14 | | 2-Cl—Ph | NMR1: 0.08-0.12(2H, m), 0.50-0.56(2H, m), 1.74-1.84(4H, m), 2.42-2.45(2H, m), 2.64-2.71 (2H, m), 2.85-2.91(1H, m), 6.91-6.97(2H, m), 7.41-7.63(5H, m); FP: 370 |
| 124 | 14 | | 2-CF₃—Ph | NMR1: −0.02-0.02(2H, m), 0.46-0.52(2H, m), 1.76-1.84(4H, m), 2.38-2.46(2H, m), 2.66-2.74 (2H, m), 2.86-2.91(1H, m), 6.86(1H, dd), 6.96 (1H, dd), 7.42(1H, dd), 7.68(1H, d), 7.76-7.83 (2H, m), 7.90-7.93(1H, m); FP: 404 |
| 125 | 14 | | 2-Cl-4-MeO—Ph | NMR1: 0.07-0.14(2H, m), 0.52-0.57(2H, m), 1.74-1.84(4H, m), 2.38-2.48(2H, m), 2.62-2.72 (2H, m), 2.82-2.88(1H, m), 3.84(3H, s), 6.90-6.97 (2H, m), 7.03-7.06(1H, m), 7.19(1H, d), 7.41-7.46(2H, m); FP: 400 |
| 126 | 14 | Bn | 2-Me—Ph | FP: 358; Sal:HCl |
| 127 | 14 | | 2-Cl—Ph | NMR1: 0.40-0.90(4H, m), 1.75-1.97(4H, m), 2.15-2.28(4H, m), 3.10-3.24(2H, m), 3.56-3.62 (1H, m), 6.85-6.87(2H, m), 7.20-7.25(3H, m), 7.57-7.76(4H, m); FP: 378; Sal:HCl |
| 128 | 2 | PhS(O)₂— | 2-Cl—Ph | FP: 428 |

TABLE 32

| Ex | Syn | Structure | Data |
|---|---|---|---|
| 4 | 4 | [4-Me-3-Cl-thiophene attached to cyclopentyl-triazole with N-Me and S-CH₂-(2-Cl-phenyl)] | NMR1: 1.67-1.82(4H, m), 2.08(3H, s), 2.10-2.18(2H, m), 2.59-2.64(2H, m), 2.87 (3H, s), 4.34(2H, s), 7.18-7.25(2H, m), 7.29-7.33 (2H, m), 7.45(1H, d); FP: 438; Sal: HCl |

TABLE 33

[Structure: thiophen-2-yl attached to cyclobutyl-triazole with N-cyclopropyl, R³ substituent]

| Ex | Syn | R³ | Data |
|---|---|---|---|
| 31 | 31 | 3-HO₂C—Ph | ESP: 366 |
| 32 | 32 | 4-HO—Ph | NMR1: 0.12-0.23(2H, m), 6.85(2H, d), 7.00(1H, m), 9.87(1H, s); ESP: 338 |
| 129 | 14 | Ph | NMR1: 0.11-0.21(2H, m), 0.63-0.74(2H, m), 7.01(1H, m), 7.42-7.54(4H, m); ESP: 322 |
| 130 | 14 | 4-BnO-Ph | ESP: 428 |
| 131 | 14 | 3-MeO₂C—Ph | NMR1: 0.12-0.22(2H, m), 3.89(3H, s), 7.02(1H, m), 8.30(1H, s) |
| 132 | 14 | 4-MeO₂C—Ph | NMR1: 0.12-0.23(2H, m), 3.89(3H, s), 7.02(1H, m), 7.09(1H, m), 8.07(2H, d); ESP: 380 |
| 133 | 31 | 4-HO₂C—Ph | NMR1: 0.14-0.23(2H, m), 7.02(1H, m), 8.04(2H, d); ESP: 366 |

TABLE 34
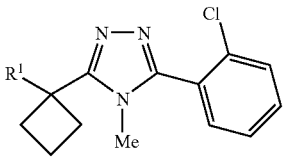
| Ex | Syn | R¹ | Data |
|---|---|---|---|
| 28 | 28 | (2-F—Ph)—NHC(O)— | FP: 385 |
| 29 | 29 | 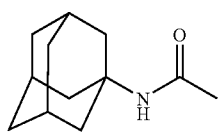 | FP: 425 |
| 30 | 30 | (4-Cl—Ph)—N(Me)—C(O)— | FP: 415 |
| 134 | 14 | 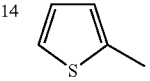 | NMR1: 3.00(3H, s), 6.95—7.06(2H, m), 7.45-7.71 (5H, m); FP: 330 |
| 135 | 20 | PhS(O)₂NH— | FP: 403 |
| 136 | 20 | (2-Cl—Ph)—S(O)₂NH— | NMR2: 1.77-1.96(2H, m), 2.21-2.36(2H, m), 2.66-2.77(2H, m), 3.55(3H, s), 5.58(1H, s), 7.38-7.58(7H, m), 7.93(1H, d, J=7.3Hz); ESP: 437.12 |
| 137 | 20 | (4-Cl—Ph)—S(O)₂NH— | NMR2: 1.78-1.99(2H, m), 2.12-2.27(2H, m), 2.77-2.91(2H, m), 3.45(3H, s), 5.15(1H, s), 7.40-7.55(6H, m), 7.77(2H, d, J=8.4Hz); ESP: 437.11 |
| 138 | 20 | (2-Me-3-Cl—Ph)—S(O)₂NH— | FP: 451 |
| 139 | 21 | PhS(O)₂N(Me)— | NMR1: 1.52-1.64(2H, m), 2.44-2.50(2H, m), 2.61-2.67(2H, m), 2.79(3H, s), 3.40(3H, s), 7.54-7.77(7H, m), 7.85-7.88(2H, m); FP: 417 |
| 140 | 21 | (2-Me-3-Cl—Ph)—S(O)₂N(Me)— | NMR1: 1.55-1.75(2H, m), 2.62(3H, s), 2.72-2.79 (4H, m), 2.86(3H, s), 3.39(3H, s), 7.48(1H, t), 7.52-7.58(2H, m), 7.62-7.66(1H, m), 7.70(1H, d, 7.77-7.81(2H, m); FP: 465 |
| 141 | 29 | cHex—N(Me)C(O)— | FP: 387 |
| 142 | 29 | (4-Cl—Ph)—NHC(O)— | NMR1: 1.95-2.06(2H, m), 2.75-2.93(4H, m), 3.23 (3H, s), 7.35(2H, d), 7.50-7.68(6H, m), 9.80(1H, s). FP: 401 |
| 143 | 29 | 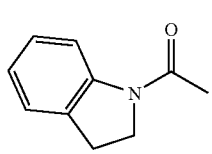 | NMR1: 1.88-2.13(2H, m), 2.82(2H, br s), 2.91-3.05 (4H, m), 3.18(3H, s), 3.62(2H, t), 7.03(1H, t), 7.18 (1H, t), 7.23(1H, d), 7.51(1H, t), 7.58-7.66(3H, m), 8.14(1H, d); FP: 393 |
| 144 | 29 | PhNHC(O)— | FP: 367 |
| 145 | 29 | 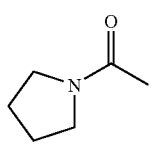 | FP: 345 |

TABLE 35

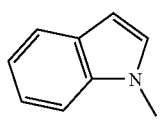

| Ex | Syn | R¹ | Data |
|---|---|---|---|
| 16 | 16 | PhN(Bz)— | NMR1: 1.61(6H, s), 1.99(3H, s), 2.77(3H, s), 3.46(3H, s), 6.90-6.94(3H, m), 7.15-7.47(6H, m); FP: 321 |
| 17 | 17 | PhN(Ac)— | NMR1: 1.55(6H, s), 1.65(3H, s), 2.09(3H, s), 3.47(3H, s), 7.29-7.56(9H, m); FP: 349 |
| 21 | 21 | PhS(O)₂N(Me)— | NMR1: 1.59(6H, s), 2.13(3H, s), 2.86(3H, s), 3.46(3H, s), 7.33-7.50(4H, m), 7.63-7.67(2H, m), 7.70-7.75(1H, m), 7.85-7.88(2H, m); FP: 385 |
| 146 | 14 | PhO— | NMR1: 1.84(6H, s), 2.01(3H, s), 3.43(3H, s), 6.64-6.67(2H, m), 6.97-7.01(1H, m), 7.20-7.50(6H, m); FP: 308; Sal: HCl |
| 147 | 14 | (2-Cl—Ph)—O— | NMR1: 1.88(6H, s), 2.08(3H, s), 3.53(3H, s), 6.52-6.54(1H, m), 7.04-7.08(1H, m), 7.16-7.20(1H, m), 7.38-7.54(5H, m); FP: 342; Sal: HCl |
| 148 | 14 | PhNH— | NMR1: 1.73(6H, s), 1.92(3H, s), 3.31(3H, s), 6.09(1H, s), 6.34(2H, d), 6.52(1H, dd), 6.95-6.99(2H, m), 7.23-7.45(4H, m); FP: 307 |
| 149 | 15 | PhN(Me)— | NMR1: 1.61(6H, s), 1.99(3H, s), 2.77(3H, s), 3.46(3H, s), 6.90-6.94(3H, m), 7.15-7.47(6H, m); FP: 321 |
| 150 | 20 | MsNH— | FP: 309 |
| 151 | 20 | PhS(O)₂NH— | FP: 371 |
| 152 | 20 | (2-Me-3-Cl—Ph)—S(O)₂NH— | FP: 419 |
| 153 | 22 | PhNHC(O)NH— | FP: 350 |
| 154 | 23 | BzNH— | FP: 335 |

TABLE 36

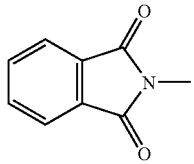

| Ex | Syn | R¹ | Data |
|---|---|---|---|
| 15 | 15 | PhN(Me)— | NMR1: 1.58(6H, s), 2.74(3H, s), 3.54(3H, s), 6.93-6.96(3H, m), 7.17-7.21(2H, m), 7.51-7.56(2H, m), 7.58-7.67(2H, m); FP: 341 |
| 18 | 18 | 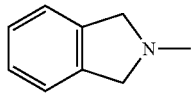 | NMR1: 2.11(6H, s), 2.43(3H, s), 6.57-6.63(2H, m), 6.92-7.03(2H, m), 7.45-7.59(5H, m), 7.70(1H, d); ESP: 351 |
| 24 | 24 | BzN(Me)— | FP: 369 |
| 25 | 25 | (phthalimido) | NMR1: 2.06(6H, s), 3.27(3H, s), 7.52-7.55(2H, m), 7.59-7.68(2H, m), 7.86(4H, br s); FP: 381 |
| 26 | 26 | (isoindolinyl) | NMR1: 1.61(6H, s), 3.61(3H, s), 3.93(4H, s), 7.18-7.26(4H, m), 7.52-7.69(4H, m); FP: 353 |
| 33 | 33 | cPen—NH— | NMR1: 1.03-1.16(2H, m), 1.30-1.41(2H, m), 1.47-1.59(4H, m), 1.54(6H, s), 2.09-2.14(1H, m), 2.82-2.90(1H, m), 3.65(3H, s), 7.49-7.68(4H, m); FP: 319 |

TABLE 36-continued

| Ex | Syn | R¹ | Data |
|---|---|---|---|
| 34 | 34 | cPen—N(Me)— | NMR1: 1.34-1.86(8H, m), 1.93(6H, s), 2.77(3H, s), 3.68(3H, s), 3.82-3.92(1H, m), 7.57-7.74(4H, m); FP: 333 |
| 35 | 35 | PhNHCH₂— | FP: 341 |
| 36 | 36 |  | NMR1: 1.63(6H, s), 3.11(3H, s), 5.86(1H, d), 6.53 (1H, d), 6.87(1H, dd), 6.95(2H, d), 7.08-7.20(3H, m), 7.42(1H, dt), 7.50-7.58(2H, m); FP: 338 |
| 57 | 57 | PhCH(OH)— | FP: 342 |
| 58 | 58 | Bz | FP: 340 |
| 59 | 59 |  | FP: 319 |
| 155 | 2 | PhS(O)₂— | FP: 376 |
| 156 | 14 | 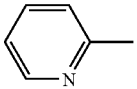 | NMR1: 1.85(6H, s), 2.98(3H, s), 6.94-7.01(2H, m), 7.47-7.66(5H, m); FP: 318 |

TABLE 37

| 157 | 14 | 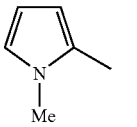 | NMR2: 1.94(6H, s), 2.88(3H, s), 7.13-7.22(2H, m), 8.58-8.63(1H, m); ESP: 313 |
| 158 | 14 | 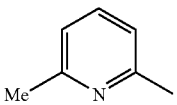 | NMR2: 1.89(6H, s), 2.89(3H, s), 3.21(3H, s), 7.35-7.52(4H, m); ESP: 315 |
| 159 | 14 | PhO— | FP: 328; Sal: HCl |
| 160 | 14 | (2-Cl—Ph)—O— | NMR1: 1.86(6H, s), 3.51(3H, s), .643-6.45(1H, m), 7.04-7.06(1H, m), 7.13-7.15(1H, m), 7.48-7.68(5H, m); FP: 362; Sal: HCl |
| 161 | 14 | PhNH— | NMR1: 1.72(6H, s), 3.37(3H, s), 6.05(1H, s), 6.40 (2H, d), 6.46-6.55(1H, m), 6.95-6.99(2H, m), 7.49-7.63 (4H, m); FP: 327 |
| 162 | 14 | (2-Cl—Ph)—NH— | NMR1: 1.82(6H, s), 3.32(3H, s), 5.23(1H, s), 6.14-6.16 (1H, m), 6.61-6.65(1H, m), 6.92-6.96(1H, m), 7.30-7.32 (1H, m), 7.48-7.63(4H, m); FP: 361 |
| 163 | 14 | (2-Me—Ph)—NH— | NMR2: 1.90(6H, s), 2.19(3H, s), 3.46(3H, s), 3.70 (1H, s), 6.22(1H, d, J=2.5Hz), 6.66(1H, dd, J=2.5, 2.4Hz), 6.92(1H, dd, J=2.7, 2.4Hz), 7.07(1H, d, J=2.4Hz), 7.33-7.53(4H, m); ESP: 341.40 |
| 164 | 14 | (4-Me—Ph)—NH— | NMR2: 1.84(6H, s), 2.20(3H, s), 3.56(3H, s), 3.67 (1H, s), 6.30(2H, d, J=2.9Hz), 6.90(2H, d, J=2.9Hz), 7.34-7.53(4H, m); ESP: 341.34 |
| 165 | 14 | (2-Me-3-Cl—Ph)—NH— | NMR2: 1.91(6H, s), 2.27(3H, s), 3.43(3H, s), 3.84 (1H, s), 6.15(1H, d, J=2.7Hz), 6.74-6.86(2H, m), 7.34-7.52(4H, m) |
| 166 | 14 |  | NMR2: 1.91(6H, s), 2.53(3H, s), 2.90(3H, s), 6.93 (1H, d, J=7.7Hz), 7.02(1H, d, J=7.7Hz), 7.34-7.55 (5H, m); ESP: 327 |

TABLE 37-continued

| | | | |
|---|---|---|---|
| 167 | 14 |  | NMR1: 1.64(6H, s), 3.34(3H, s), 5.30(1H, br), 5.43 (1H, br), 6.88-7.02(2H, m), 7.16-7.30(3H, m), 7.46-7.72 (2H, m); ESP: 338 |
| 168 | 17 | (4-Me—Ph)—N(Ac)— | NMR2: 1.71(6H, s), 1.74(3H, s), 2.43(3H, s), 3.64 (3H, s), 7.36-7.63(8H, m); ESP: 383 |
| 169 | 20 | PhS(O)$_2$NH— | NMR1: 1.54(6H, s), 3.45(3H, s), 7.46(1H, dd), 7.53-7.65(5H, m), 7.68(1H, dd), 7.73-7.76(2H, m), 8.42 (1H, s); FP: 391 |
| 170 | 20 | (2-Me-3-Cl—Ph)—S(O)$_2$NH— | NMR1: 1.54(6H, s), 2.66(3H, s), 3.50(3H, s), 7.42 (1H, t), 7.48(1H, dd), 7.55(1H, dt), 7.63(1H, dt), 7.69 (1H, dd), 7.72-7.77(2H, m), 8.64(1H, s); FP: 439 |
| 171 | 21 | PhS(O)$_2$N(Me)— | NMR1: 1.61(6H, s), 2.83(3H, s), 3.49(3H, s), 7.53-7.58(2H, m), 7.62-7.75(5H, m), 7.86-7.90(2H, m); FP: 405 |

TABLE 38

| | | | |
|---|---|---|---|
| 172 | 21 | (2-Me-3-Cl—Ph)—S(O)$_2$N(Me)— | NMR1: 1.75(6H, s), 2.61(3H, s), 2.86(3H, s), 3.41 (3H, s), 7.49(1H, t), 7.52-7.56(2H, m), 7.61-7.66(1H, m), 7.69(1H, d), 7.80(1H, d), 7.92(1H, d); FP: 453 |
| 173 | 21 | PhS(O)$_2$N(Et)— | NMR2: 1.15(3H, t, J=7.0Hz), 1.73(6H, s), 3.45(2H, q, J=7.0Hz), 3.68(3H, s), 7.38-7.66(7H, m), 7.92(2H, d, J=7.0Hz); ESP: 419 |
| 174 | 23 | BzNH— | FP: 355 |
| 175 | 29 | 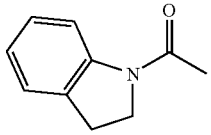 | FP: 381 |
| 176 | 33 | cHex—NH— | FP: 333 |
| 177 | 33 | BnNH— | FP: 341 |
| 178 | 33 | cHex—CH$_2$—NH— | FP: 347 |
| 179 | 33 | iPrNH— | NMR1: 0.79(6H, d), 1.55(6H, s), 1.87-1.91(1H, m), 2.82-2.92(1H, m), 3.67(3H, s), 7.48-7.68(4H, m) FP: 293 |
| 180 | 33 | cBu—NH— | NMR1: 1.37-1.52(2H, m), 1.49(6H, s), 1.64-1.74(2H, m), 1.93-2.00(2H, m), 2.46(1H, d), 2.79-2.90(1H, m), 3.59(3H, s), 7.50-7.69(4H, m) FP: 305 |
| 181 | 34 | cHex—N(Me)— | NMR1: 1.01-2.23(10H, m), 1.99(6H, s), 2.81(3H, s), 3.37-3.48(1H, m), 3.68(3H, s), 7.56-7.74(4H, m); FP: 347 |
| 182 | 34 | cHex—CH$_2$—N(Me)— | FP: 361 |
| 183 | 34 | BnN(Me)— | NMR1: 1.88(6H, br, s), 2.58(3H, br, s), 3.68(3H, br, s), 4.88(2H, br, s), 7.36-7.74(9H, m); FP: 355 |
| 184 | 34 | iPrN(Me)— | NMR1: 0.89(3H, br, s), 1.38(3H, br, s), 1.98(6H, s), 2.77(3H, s), 3.67(3H, s), 3.78-3.92(1H, m), 7.58-7.74 (4H, m); FP: 307 |
| 185 | 34 | cBu—N(Me)— | NMR1: 1.15-1.42(2H, m), 1.44-1.62(2H, m), 1.93(6H, s), 1.93-2.29(2H, m), 2.65(3H, s), 3.80(3H, s), 3.90-4.00(1H, m), 7.52-7.73(4H, m); FP: 319 |
| 186 | 14 | 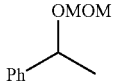 | FP: 386 |

TABLE 39

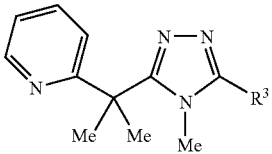

| Ex | Syn | R¹ | R³ | Data |
|---|---|---|---|---|
| 187 | 2 | PhS(O)₂— | 2-Cl—Ph | FP: 402 |
| 188 | 14 | PhO— | 2-Me—Ph | NMR1: 0.65-0.70(2H, m), 0.80-0.86(2H, m), 1.92(6H, s), 2.17(3H, s), 3.37-3.46(1H, m), 6.72(2H, d), 7.03-7.07(1H, m), 7.25-7.29(2H, m), 7.37-7.43 (2H, m), 7.49-7.54(2H, m); FP: 334; Sal: HCl |
| 189 | 14 | PhO— | 2-Cl—Ph | FP: 354; Sal: HCl |

TABLE 40

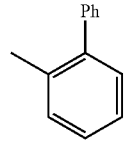

| Ex | Syn | R³ | Data |
|---|---|---|---|
| 45 | 45 | 4-MeHNOC—Ph | ESP: 350 |
| 46 | 46 | 4-H₂NOC—Ph | ESP: 336 |
| 47 | 47 | 4-AcO—Ph | ESP: 351 |
| 48 | 48 | 3-Cl-4-HO—Ph | NMR2: 1.70(6H, s), 3.45(3H, s), 6.05(1H, s), 6.35(2H, d), 6.51(1H, dd), 6.97(2H, dd), 7.08(1H, d), 7.37 (1H, dd), 7.56(1H, d), 10.73(1H, brs) ESP: 343 |
| 49 | 49 | 4-EtNHC(O)O—Ph | ESP: 380 |
| 190 | 14 | 4-BnO—Ph | ESP: 399 |
| 191 | 14 | 4-MeO₂C—Ph | ESP: 351 |
| 192 | 14 | 3-Cl-4-BnO—Ph | ESP: 433 |
| 193 | 14 | 4-CF₃O—Ph | ESP: 377 |
| 194 | 19 | 2-HO—Ph | ESP: 309 |
| 195 | 31 | 4-HO₂C—Ph | ESP: 337 |
| 196 | 32 | 4-HO—Ph | ESP: 309 |

TABLE 41

| Ex | Syn | R³ | Data |
|---|---|---|---|
| 55 | 55 | (pyrrolidinyl-o-tolyl) | ESP: 348 |
| 197 | 14 | 4-BnO—Ph | ESP: 385 |
| 198 | 14 | 4-HO—Ph | ESP: 295 |

TABLE 41-continued

| Ex | Syn | R³ | Data |
|---|---|---|---|
| 199 | 14 | 4-NC—Ph | ESP: 304 |
| 200 | 14 | 2-F—Ph | ESP: 297 |
| 201 | 14 | 4-F—Ph | ESP: 297 |
| 202 | 14 | 2-Br—Ph | NMR2: 1.94(6H, s), 2.87(3H, s), 7.14-7.22 (2H, m), 7.33-7.52(3H, m), 7.62-7.68(2H, m), 8.59-8.62(1H, m); ESP: 357 |
| 203 | 14 | 4-Br—Ph | ESP: 357 |
| 204 | 14 | 3-BnO—Ph | ESP: 385 |
| 205 | 14 | 4-MeO₂C—Ph | ESP: 337 |
| 206 | 14 | 3-HO—Ph | ESP: 395 |
| 207 | 14 | 2-CF₃—Ph | NMR2: 1.93(6H, s), 2.77(3H, s), 7.10(1H, d), 7.19(1H, dd), 7.47-7.51(1H, m), 7.61-7.69(3H, m), 7.77-7.82 (1H, m), 8.57-8.61(1H, m) ESP: 347 |
| 208 | 14 | 3-Br—Ph | ESP: 357 |
| 209 | 14 | 4-CF₂O—Ph | ESP: 363 |
| 210 | 14 | 2-MeO—Ph | NMR2: 1.93(6H, s), 2.86(3H, s), 3.75(3H, s), 6.94(1H, d), 7.06(1H, dt), 7.13(1H, dt), 7.18(1H, ddd), 7.45(1H, ddd), 7.50(1H, dd), 7.63(1H, dt), 8.57-8.62(1H, m) ESP: 309 |
| 211 | 14 | 2-methylphenyl (Ph-tolyl) | ESP: 355 |

TABLE 42

| Ex | Syn | R³ | Data |
|---|---|---|---|
| 212 | 14 | 2-Cl—Ph | NMR2: 1.92(6H, s), 2.98(3H, s), 7.02(1H, d), 7.23(1H, d), 7.35-7.54(4H, m), 7.61(1H, t) ESP: 347 |
| 213 | 14 | 2-Br—Ph | NMR2: 1.92(6H, s), 2.97(3H, s), 7.04(1H, d), 7.23(1H, d), 7.33-7.51(3H, m), 7.60(1H, t), 7.66(1H, dd) ESP: 391 |

TABLE 43
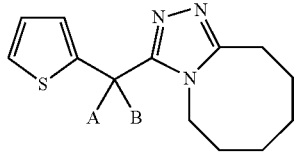
| Ex | Syn | A | B | Data |
|---|---|---|---|---|
| 214 | 5 | Et | Et | FP: 304; Sal: HCl |
| 215 | 5 | MeO—(CH$_2$)$_2$— | MeO—(CH$_2$)$_2$— | FP: 364 |
TABLE 43-continued
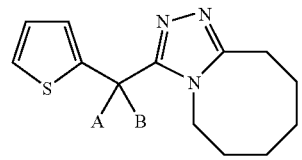
| Ex | Syn | A | B | Data |
|---|---|---|---|---|
| 216 | 5 | nPr | nPr | FP: 332; Sal: HCl |
| 217 | 7 | HO—(CH$_2$)$_2$— | HO—(CH$_2$)$_2$— | FP: 336 |
TABLE 44
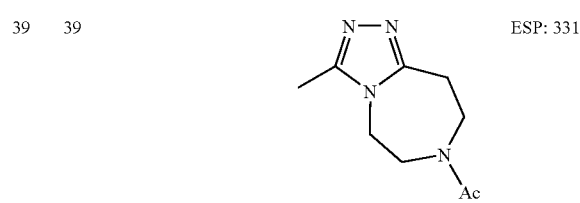
| Ex | Syn | R$^1$ | | Data |
|---|---|---|---|---|
| 38 | 38 | (2-thienyl) | (3-methyl-triazolo-diazepine-NH) | ESP: 289 |
| 39 | 39 | | (3-methyl-triazolo-diazepine-N-Ac) | ESP: 331 |
| 218 | 5 | 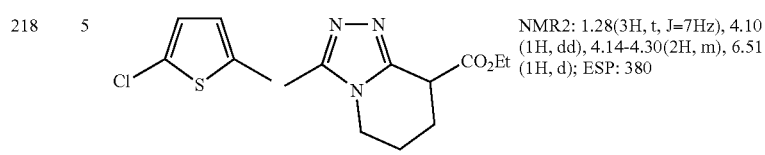 | | NMR2: 1.28(3H, t, J=7Hz), 4.10 (1H, dd), 4.14-4.30(2H, m), 6.51 (1H, d); ESP: 380 |
| 219 | 5 | 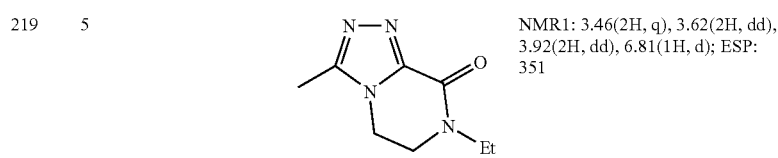 | | NMR1: 3.46(2H, q), 3.62(2H, dd), 3.92(2H, dd), 6.81(1H, d); ESP: 351 |

TABLE 44-continued

| Ex | Syn | R¹ | Data |
|---|---|---|---|
| 220 | 5 | [triazole-piperazine-SO₂Ph structure] | NMR2: 3.40(2H, dd), 3.64(2H, dd), 4.48(2H, s), 6.49(1H, d, J=4Hz), 7.77-7.83(2H, m); ESP: 449 |
| 221 | 5 | [triazole-diazepane-CO₂Bn structure] | ESP: 457 |

TABLE 45

| Ex | Syn | R¹ | Data |
|---|---|---|---|
| 222 | 5 | [triazole-diazepane-CO₂Bn structure] | ESP: 409 |
| 223 | 15 | [triazole-piperazine-Me structure] | ESP: 289 |
| 224 | 20 | [triazole-diazepane-Ms structure] | ESP: 353 |
| 225 | 22 | [triazole-diazepane-CONH₂ structure] | ESP: 318 |

TABLE 45-continued

[Structures: thiophene-cyclobutyl-triazole with R2, R3 substituents; methyl-triazole with R2, R3]

| Ex | Syn | Data |
|---|---|---|
| 226 | 38 | ESP: 275 |

[Structure: methyl-triazolo-diazepine with NH]

TABLE 46

| Ex | Syn | Structure | Data |
|---|---|---|---|
| 227 | 14 | [thiophene-cyclobutyl-triazole-(2-chlorophenyl) with CH2CH2-NH-Ms] | ESP: 437 |

TABLE 47

[Structure: R¹–C(Me)₂– attached to triazole (N-Me) with 2-chlorophenyl]

| No | R¹ |
|---|---|
| 1 | BnC(O)— |
| 2 | Ph—CH(—NHAc)— |
| 3 | EtO₂C–C(Ph)=CH–Me |
| 4 | Ph-cyclopropyl |
| 5 | PhNHCH(Ph)— |
| 6 | PhCF₂— |
| 7 | HO₂C–C(Ph)=CH–Me |

TABLE 47-continued

[Same core structure]

| No | R¹ |
|---|---|
| 8 | Ph—C≡C— |
| 9 | 2-methyl-indane |
| 10 | 1-phenyl-1-methyl-cyclopropyl |
| 11 | Ph₂CH— |
| 12 | Ph—(CH₂)₂— |
| 13 | 2-methyl-indene |
| 14 | PhC(Me)₂— |
| 15 | cHex—N(Et)— |
| 16 | cHex—N(Ac)— |
| 17 | cHex—N(Ms)— |
| 18 | cHex–N(Me)–CH₂–CO₂H |
| 19 | cHex–N(Me)–CH₂–CO₂Me |
| 20 | cHex–N(Me)–CH₂CH₂–OH |
| 21 | cHex–N(Me)–CH₂CH₂–OMe |
| 22 | BnN(Et)— |
| 23 | BnN(Ac)— |
| 24 | BnN(Ms)— |
| 25 | HO₂C—CH₂—N(Bn)— |
| 26 | MeO₂C—CH₂—N(Bn)— |
| 27 | HO—(CH₂)₂—N(Bn)— |
| 28 | MeO—(CH₂)₂—N(Bn)— |
| 29 | 2-(N-methylamino)-tetrahydronaphthalene |

TABLE 47-continued
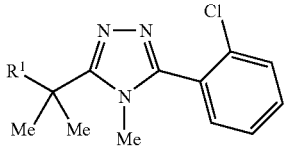
| No | R¹ |
|---|---|
| 30 | 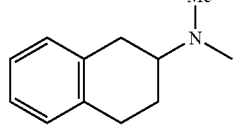 |
| 31 | 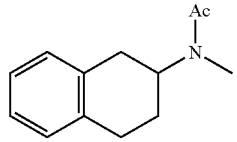 |
| 32 | 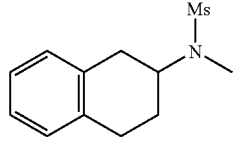 |
| 33 | 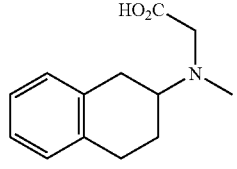 |
| 34 | 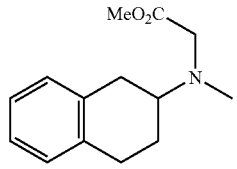 |
| 35 | 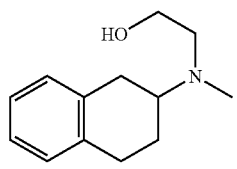 |
| 36 | 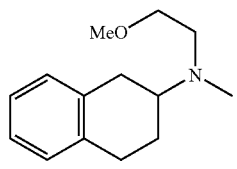 |
| 37 | 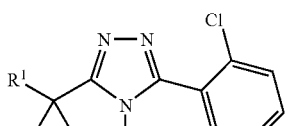 |
TABLE 47-continued
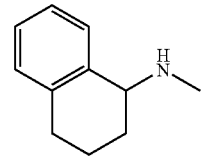
| No | R¹ |
|---|---|
| 38 | 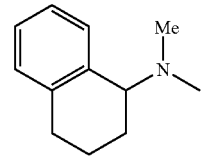 |
| 39 | 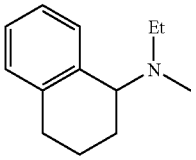 |
TABLE 48
| 40 | 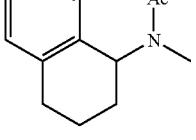 |
|---|---|
| 41 | 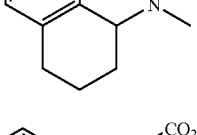 |
| 42 | 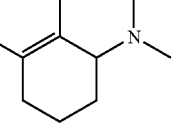 |
| 43 | 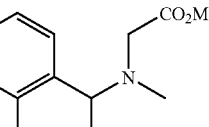 |
| 44 | (image not listed) |

TABLE 48-continued
| | | | | |
|---|---|---|---|---|
| 45 | 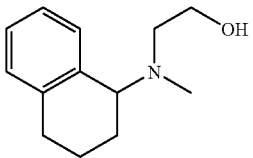 | 54 | 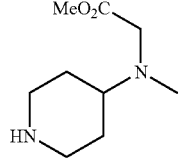 |
| 46 | 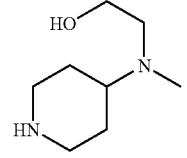 | 55 | 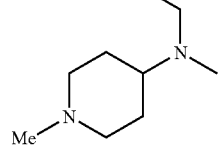 |
| 47 | 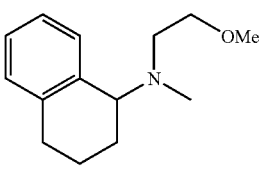 | 56 | 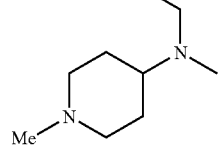 |
| 48 | 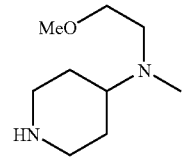 | 57 | 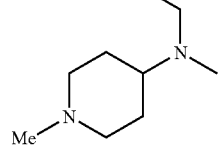 |
| 49 | 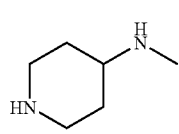 | 58 | 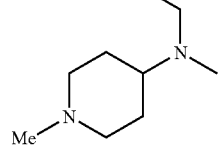 |
| 50 | 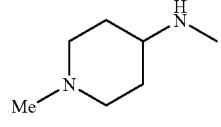 | 59 | 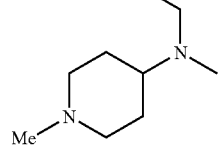 |
| 51 | 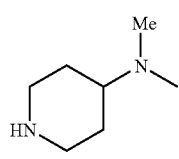 | 60 | 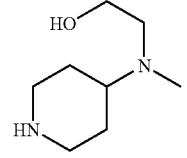 |
| 52 | 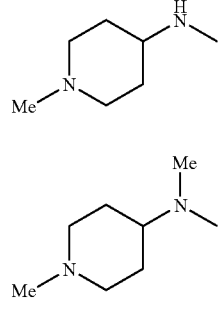 | 61 | 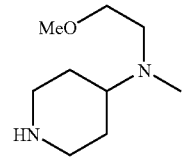 |
| 53 | 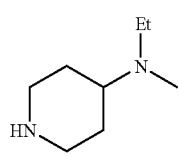 | 62 | 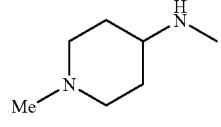 |

TABLE 48-continued
| | |
|---|---|
| 63 | 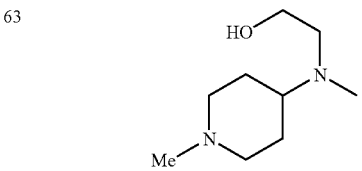 |
| 64 | 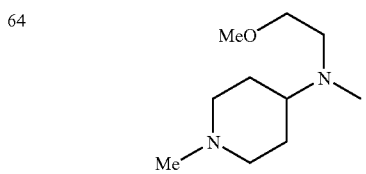 |
| 65 | 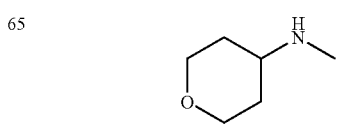 |
| 66 | 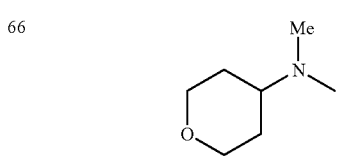 |
| 67 | 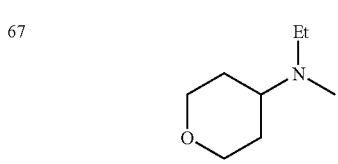 |
| 68 | 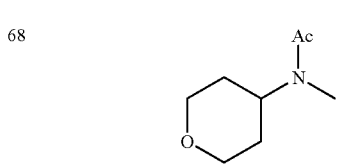 |
| 69 | 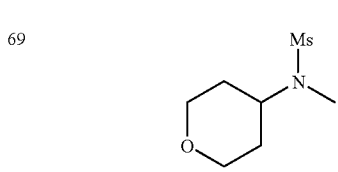 |
TABLE 49
| | |
|---|---|
| 70 | 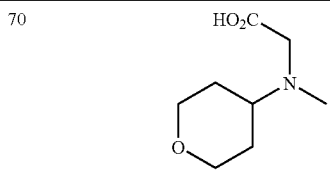 |
| 71 | 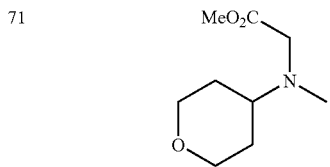 |
TABLE 49-continued
| | |
|---|---|
| 72 | 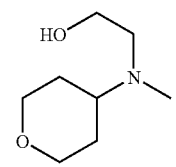 |
| 73 | 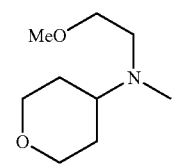 |
| 74 |  |
| 75 | 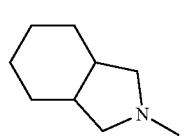 |
| 76 | 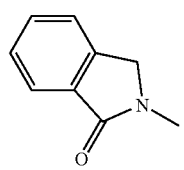 |
| 77 | 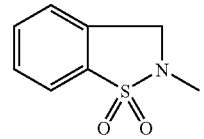 |
| 78 | 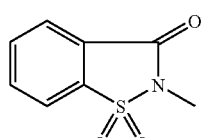 |
| 79 | PhS(O)$_2$N(Et)— |
| 80 | PhS(O)$_2$N(iPr)— |
| 81 | PhS(O)$_2$N(Ac)— |
TABLE 50
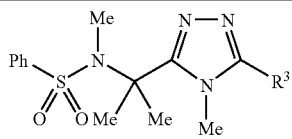
| No | R$^3$ |
|---|---|
| 82 | 2-HO—Ph |
| 83 | 4-HO—Ph |
| 84 | 4-MsNH—Ph |
| 85 | 4-MeO$_2$C—Ph |
| 86 | 4-H$_2$NOC—Ph |

TABLE 50-continued

[Structure: Ph-S(=O)₂-N(Me)-C(Me)(OMe)-triazole(N-Me)-R³]

| No | R³ |
|---|---|
| 87 | 2-pyridyl (methyl-linked) |
| 88 | 4-pyridyl (methyl-linked) |
| 89 | 2,6-dimethyl-4-pyridyl |
| 90 | 4-(piperidin-1-yl)phenyl |
| 91 | 2-(methylcarbamoylmethoxy)phenyl |
| 92 | quinolin-2-yl (methyl-linked) |
| 93 | benzo[1,3]dioxol-5-yl (methyl-linked) |

TABLE 51

[Structure: R¹-C(Me)(Me)-triazole(N-Me)-phenyl-OH]

| No | R¹ |
|---|---|
| 94 | 3-pyridyl |
| 95 | 4-pyridyl |

TABLE 52

[Structure: 2-pyridyl-C(Me)(Me)-triazole(N-Me)-R³]

| No | R³ |
|---|---|
| 96 | 2-HO-Ph |
| 97 | 4-MsNH-Ph |
| 98 | 4-H₂NOC-Ph |

TABLE 53

[Structure: Ph-NH-C(Me)(Me)-triazole(N-Me)-R³]

| No | R³ |
|---|---|
| 99 | 4-MsNH-Ph |
| 100 | 2-pyridyl |
| 101 | 4-pyridyl |
| 102 | 2,6-dimethyl-4-pyridyl |
| 103 | pyrazin-2-yl |

TABLE 54

| No | Structure |
|---|---|
| 104 | [Fused triazolo-azocane with thien-2-yl-cyclobutyl substituent and phenyl group] |
| 105 | [Fused triazolo-azocane with thien-2-yl-(3-fluorocyclobutyl) substituent] |

TABLE 54-continued

| No | Structure |
|----|-----------|
| 106 | 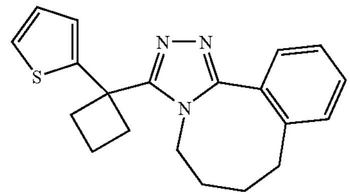 |
| 107 | 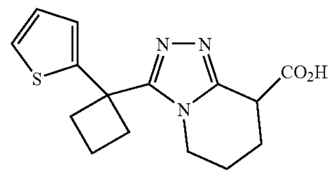 |
| 108 | 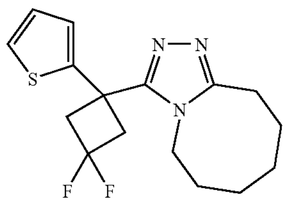 |
| 109 | 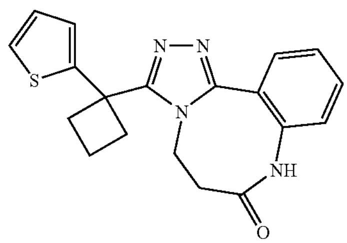 |
| 110 | 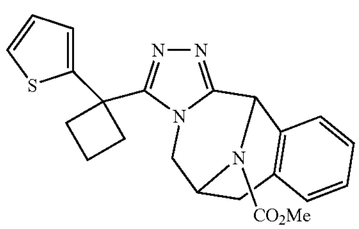 |
| 111 | 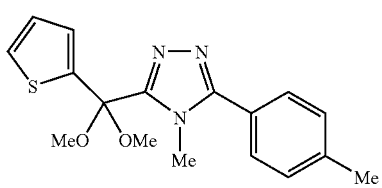 |
| 112 | 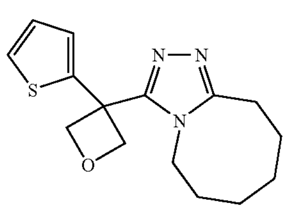 |

INDUSTRIAL APPLICABILITY

Since the compound of the present invention has an excellent 11β-HSD1 inhibitory action, the compound is useful as a preventive/therapeutic agent for diseases in which 11β-HSD1 participates, such as hyperglycemia, insulin resistance, obesity, hyperlipemia, hypertension, osteoporosis, glaucoma, and decrease in cognitive function, in particular, diabetes, insulin resistance.

The invention claimed is:

1. A compound represented by the formula (I) or a salt thereof:

[Chem 14]

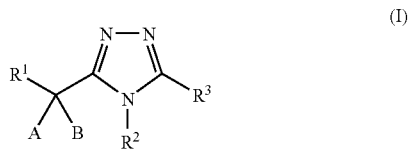

(I)

wherein the symbols have the following meanings:

$R^1$: —N($R^0$)S(O)$_2$-lower alkyl, —N($R^0$)-optionally substituted lower alkyl, —X—$R^4$, or each optionally substituted cycloalkyl or heterocyclic group;

$R^4$: each optionally substituted aryl, cycloalkyl or heterocyclic group;

X: —O—, —N($R^5$)—, —C(O)—, —S—, —S(O)—, —S(O)$_2$—, —C(O)N($R^0$)—, —N($R^0$)C(O)—, —N($R^0$)C(O)N($R^0$)—, —N($R^6$)S(O)$_2$—, —S(O)$_2$N($R^6$)—, —C(O)-lower alkylene, lower alkylene-C(O)—, —N($R^5$)-lower alkylene, lower alkylene-N($R^5$)—, or each optionally substituted lower alkylene, lower alkenylene or lower alkynylene;

$R^5$: —H, lower alkyl, lower alkylene-CO$_2$$R^0$, lower alkylene-O$R^0$, —C(O)$R^0$ or —C(O)-aryl, —S(O)$_2$$R^0$, —S(O)$_2$-aryl or aryl;

$R^6$: —H, lower alkyl, —C(O)$R^0$ or —C(O)-aryl;

$R^0$: the same or different from each other, —H or lower alkyl;

$R^2$: —$R^7$;

$R^3$: —$R^7$, —O$R^7$, —NH$R^7$, —N($R^7$)S(O)$_2$-lower alkyl, —N($R^7$)$_2$ or —S-lower alkylene-(optionally substituted aryl);

or $R^2$ and $R^3$ are combined together with the nitrogen atom and the carbon atom to which they are attached to form a nitrogen-containing heterocycle;

provided that a ring formed by condensing the triazole ring with the nitrogen-containing heterocycle, which is formed by combining $R^2$ and $R^3$ together with the nitrogen atom and the carbon atom to which they are attached, is not pyrazolo[5,1-c][1,2,4]triazole nor [1,2,4]triazolo[3,4-b][1,3,4]thiadiazine;

$R^7$: the same or different from each other, each optionally substituted lower alkyl, lower alkenyl, lower alkynyl, cycloalkyl, aryl or heterocyclic group;

A and B: the same or different from each other, halogen, —$R^7$, —OH, —O$R^7$, —NH$_2$, —NH$R^7$, —N($R^7$)$_2$, —S$R^7$, —S(O)$R^7$ or —S(O)$_2$$R^7$; or A and B may be combined together with the carbon atom to which they are attached to form each optionally substituted cycloalkyl ring or non-aromatic heterocycle;

provided that:
1-(1-{5-[(4-chlorobenzyl)sulfanyl]-4-methyl-4H-1,2,4-triazol-3-yl}-1-methylethyl)-1H-1,2,4-triazole,
1-{1-methyl-1-[5-(4-methylphenyl)-4-phenyl-4H-1,2,4-triazol-3-yl]ethyl}-1H-1,2,3-benzotriazole,
N-[2-(4-chlorophenyl)ethyl]N-methyl-1-(5-methyl-4-phenyl-4H-1,2,4-triazol-3-yl)cyclohex-2-en-1-amine, 3-(2,4-dichlorophenyl)-4-methyl-5-[1-(2-thienyl)cyclopropyl]-4H-1,2,4-triazole, 3-chloro-4-{4-methyl-5-[1-(2-thienyl)cyclopropyl]-4H-1,2,4-triazol-3-yl}benzamide, and N-(3-chloro-4-{4-methyl-5-[1-(2-thienyl)cyclopropyl]-4H-1,2,4-triazol-3-yl}phenyl)acetamide are excluded.

2. The compound according to claim 1, which is represented by the formula (I-a):

[Chem 15]

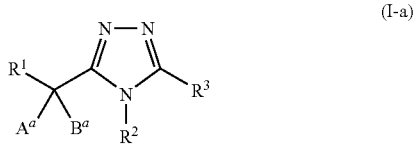

wherein $R^1$, $R^2$, and $R^3$ have the meanings as described in claim 1 and the other symbols have the following meanings:

$A^a$ and $B^a$: the same or different from each other, halogen, —$R^7$, —OH, —$OR^7$, —$NH_2$, —$NHR^7$, —$N(R^7)_2$, —$SR^7$, —$S(O)R^7$ or —$S(O)_2R^7$, wherein $R^7$ has the meaning as described in claim 1; or (i) in the case that $R^1$ is other than an aromatic heterocyclic group or (ii) in the case that $R^2$ and $R^3$ are combined together with the nitrogen atom and the carbon atom to which they are attached to form a nitrogen-containing heterocycle, $A^a$ and $B^a$ may be combined together with the carbon atom to which they are attached to form each optionally substituted cycloalkyl ring or non-aromatic heterocycle.

3. The compound according to claim 2, wherein $R^2$ is lower alkyl or cycloalkyl.

4. The compound according to claim 3, wherein $R^3$ is optionally substituted phenyl.

5. The compound according to claim 3, wherein $A^a$ and $B^a$ are the same or different from each other and each is optionally substituted lower alkyl.

6. The compound according to claim 5, wherein $R^1$ is an optionally substituted aromatic heterocyclic group, —N(lower alkyl)$_2$, —NH-(optionally substituted phenyl), —N(lower alkyl)-(optionally substituted phenyl), —N(—C(CO)-lower alkyl)-(optionally substituted phenyl), —NH—S(O)$_2$-(optionally substituted phenyl) or —N(lower alkyl)—S(O)$_2$-(optionally substituted phenyl).

7. The compound according to claim 4, wherein $A^a$ and $B^a$ are combined together with the carbon atom to which they are attached to form optionally substituted cycloalkyl ring.

8. The compound according to claim 7, wherein $R^1$ is —C(O)NH-(optionally substituted phenyl) or —C(O)N(lower alkyl)-(optionally substituted phenyl).

9. The compound according to claim 2, wherein $R^2$ and $R^3$ are combined together with the nitrogen atom and carbon atom to which they are attached to form an optionally substituted nitrogen-containing heterocycle.

10. The compound according to claim 9, wherein $R^2$ and $R^3$ are combined to form $C_{6-10}$ alkylene and it forms an optionally substituted 8-membered to 12-membered ring together with the nitrogen atom and carbon atom to which they are attached.

11. The compound according to claim 10, wherein $A^a$ and $B^a$ are combined together with the carbon atom to which they are attached to form optionally substituted cycloalkyl ring.

12. The compound according to claim 11, wherein $R^1$ is an optionally substituted aromatic heterocyclic group.

13. The compound according to claim 1 selected from the group consisting of:

3-[1-(5-chloro-2-thienyl)cyclopenty]-5,6,7,8,9,10-hexahydro[1,2,4]triazolo[4,3-a]azocine, N-methyl-N-{1-methyl-1-[4-methyl-5-(2-methylphenyl)-4H-1,2,4-triazol-3-yl]ethyl}benzenesulfonamide, N-methyl-N-{1-methyl-1-[4-methyl-5-(2-methylphenyl)-4H-1,2,4-triazol-3-yl]ethyl}aniline, N-{1-methyl-1-[4-methyl-5-(2-methylphenyl)-4H-1,2,4-triazol-3-yl]ethyl}-N-phenylacetamide, 3-(2-chlorophenyl)-4-methyl-5-[1-methyl-1-(2-thienyl)ethyl]-4H-1,2,4-triazole, cis-3-(5,6,7,8,9,10-hexahydro[1,2,4]triazolo[4,3-a]azocin-3-yl)-3-(2-thienyl)cyclobutanol, 2-{1-[5-(2-chlorophenyl)-4-methyl-4H-1,2,4-triazol-3-yl]-1-methylethyl}pyridine, N-(4-chlorophenyl)-1-[5-(2-chlorophenyl)-4-methyl-4H-1,2,4-triazol-3-yl]cyclobutanecarboxamide, 2-[5-(2-chlorophenyl)-4-methyl-4H-1,2,4-triazol-3-yl]-N-isopropyl-N-methyl-2-propanamine, 2-{1-[5-(2-bromophenyl)-4-methyl-4H-1,2,4-triazol-3-yl]-1-methylethyl}pyridine, 2-chloro-6-{1-[5-(2-chlorophenyl)-4-methyl-4H-1,2,4-triazol-3-yl]-1-methylethyl}pyridine, and 2-{1-[5-(2-bromophenyl)-4-methyl4H-1,2,4-triazol-3-yl]-1-methylethyl}-6-chloropyridine;

or a pharmaceutically acceptable salt thereof.

14. A pharmaceutical composition comprising the compound according to claim 1 or a pharmaceutically acceptable salt thereof and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,776,897 B2 | Page 1 of 1 |
| APPLICATION NO. | : 11/663089 | |
| DATED | : August 17, 2010 | |
| INVENTOR(S) | : Murakami et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 255 days.

Signed and Sealed this
Fifteenth Day of February, 2011

David J. Kappos
*Director of the United States Patent and Trademark Office*